United States Patent [19]
Zapol et al.

[11] Patent Number: 5,485,827
[45] Date of Patent: Jan. 23, 1996

[54] METHODS AND DEVICES FOR TREATING PLUMONARY VASOCONSTRICTION AND ASTHMA

[75] Inventors: Warren M. Zapol, Concord, Mass.; Claes Frostell, Danderyd, Sweden

[73] Assignee: The General Hospital Corporation, Boston, Mass.

[21] Appl. No.: 384,792

[22] Filed: Feb. 10, 1995

Related U.S. Application Data

[63] Continuation of Ser. No. 767,234, Sep. 27, 1991, abandoned, which is a continuation-in-part of Ser. No. 622,865, Dec. 5, 1990, abandoned.

[51] Int. Cl.$^6$ .................................................. A61M 11/00
[52] U.S. Cl. .............................. 128/200.14; 128/200.23; 128/203.15
[58] Field of Search ...................... 128/200.14, 200.23, 128/203.12, 203.15

[56] References Cited

U.S. PATENT DOCUMENTS

| | | | |
|---|---|---|---|
| 3,785,377 | 1/1974 | Jorgensen | 128/188 |
| 4,010,897 | 3/1977 | Treharne et al. | 239/8 |
| 4,287,040 | 9/1981 | Alamaro | 204/179 |
| 4,297,123 | 10/1981 | Wyse et al. | 71/58 |
| 4,336,798 | 6/1982 | Beran | A61M/128 |
| 4,534,343 | 8/1985 | Nowacki et al. | 128/200.23 |
| 4,592,348 | 6/1986 | Waters et al. | 128/200.23 |
| 4,667,668 | 5/1987 | Wetterlin | 128/203.15 |
| 4,852,561 | 8/1989 | Sperry | 128/200.23 |
| 4,877,589 | 10/1989 | O'Hare | 422/186.24 |
| 4,915,915 | 4/1990 | Treharne | 422/186.24 |
| 4,954,526 | 9/1990 | Keefer | 514/645 |
| 5,007,419 | 4/1991 | Weinstein et al. | 128/200.23 |
| 5,155,137 | 10/1992 | Keeer et al. | 514/611 |
| 5,208,233 | 5/1993 | Keefer et al. | 514/231.8 |
| 5,427,797 | 6/1995 | Frostell et al. | 424/434 |

FOREIGN PATENT DOCUMENTS 2144997  3/1985  United Kingdom .

OTHER PUBLICATIONS

Altabef et al., Intravenous Nitroglycerin for Uterine Relaxation of an Inverted Uterus, Am. J. Obstet. Gynecol. 166:1237–8, 1992.

Contractor et al., Development and Evaluation of an Inhalation Aerosol of Nitroglycerin, J. Pharm. Sci. 63:907–911, 1974.

Dupuy et al., Bronchodilator Action of Inhaled Nitric Oxide in Guinea Pigs, J. Clin. Invest. 90:421–428, 1992.

Kreye et al., Comparison of Sodium Nitroprusside and Isoprenaline Aerosols, Naunyn–Schmiedeberg's Arch. Pharmacol. 306:203–207, 1979.

PCT Search Report from corresponding PCT application No. PCT/US93/06091, mailed 15 Nov. 1993.

Supplementary European Search Report for corresponding EP application No. 92902708.4, mailed 19 Oct. 1993.

Blomqvist et al., Inhaled Nitric Oxide (NO): A Selective Pulumonary Vasodilator Reversing Human Hypoxic Pulmonary Vasoconstriction (HPV), Circulation 84:361, 1991.

Desai et al., Involvement of Nitric Oxide in the Reflex Relaxation of the Stomach to Accomodate Food or Fluid, Nature 351:477, 1991.

Donahoe et al., Production of $O_3$, NO, and $N_2O$ in a Pulsed Discharge at 1 Atm, Ind. Eng. Chem. 16:208–215, 1977.

Fractacci et al., Inhaled Nitric Oxide, Anesthesiology 75:990–999, 1991.

Pepke–Zaba et al., Inhaled Nitric Oxide as a Cause of Selective Pulmonary Vasodilation in Pulomonary Hypertension, The Lancet 338:1173–1174, 1991.

(List continued on next page.)

Primary Examiner—Aaron J. Lewis
Attorney, Agent, or Firm—Fish & Richardson

[57] ABSTRACT

A method for treating or preventing bronchoconstriction or reversible pulmonary vasoconstriction in a mammal, which method includes causing the mammal to inhale a therapeutically-effective concentration of gaseous nitric oxide or a therapeutically-effective amount of a nitric oxide-releasing compound, and an inhaler device containing nitric oxide gas and/or a nitric oxide-releasing compound.

39 Claims, 15 Drawing Sheets

OTHER PUBLICATIONS

Rimar et al., Prolonged Duration of Inhaled Nitric Oxide Induced Vasodilation in Perfused Rabbit Lungs, Circulation 84:362, 1991.
Roberts, Jr., et al., Inhaled Nitric Oxide (NO): A Selective Pulmonary Vasodilator for the Treatment of Persistent Pulmonary Hypertension of the Newborn (PPHN), Circulation 84:1279, 1991.
Cremona et al., Lung 169:185–202, 1991.
Dinh Xuan et al., Eur. Respir. J. 3:633–638, 1990.
Dinh Xuan et al., Respiratory Medicine 84:189–197, 1990.
Dinh Xuan et al., J. International Medical Research 17:305–315, 1989.
Foubert et al., Lancet 339:1616, 1992.
PCT Search Report issued in application PCT/US91/09111 dated Apr. 15, 1992.
Peckham, J. Ped., 6:1005–1010, 1978.
Zapol et al., Mercel Dekker, 241–273, 1985.
Fox et al., Pediatrics, 59:205–211, 1977.
Dworetz et al., Pediatrics, 84:1–6, 1989.
Fishman,McGraw–Hill, 2:999–1048, 1988.
Redermacher et al., Anesthesiology, 68:152–157, 1988.
Vlahakes et al., Circulation 63:87–95, 1981.
Ignarro et al., Proc. Natl. Acad. Sci. USA 84:9265–9269, 1987.
Palmer et al., Nature 327:524–526, 1987.
Ignarro et al., Circ. Res. 65:1–21, 1989.
Higenbottam et al., Am. Rev. Resp. Dis. Suppl. 137:107, 1988.
Meyer et al., Eur. Respir. J. 2:494–496, 1989.
Zapol et al., New England Journal of Medicine, 296:476–480, 1977.
Hounam and Morgan, "Particle Depositions" Respiratory Defense Mechanisms, Part 1:125–156, 1977.
Archer et al., J. Appl. Physiol, 68:735–747, 1990.
Furchgott et al., FASEB J. 3:2007–2018, 1989.
Archer et al., Biochem. Biophys. Res. Comm. 164:1198–1205, 1989.
Brashers et al., J. Clin. Invest. 82:1495–1502, 1988.
Ignarro et al., J. Pharmacol. Exp. Ther. 218:739–749, 1981.
Kadowitz et al., J. Clin Invest. 67:893–902, 1981.
Naeije et al., Chest 82:404–410, 1982.
Flavahan et al., J. Appl. Physiol. 58:834–838, 1985.
Hugod Int. Arch. Occup. Environ. Health 42:159–167, 1979.
Nakajima et al., Nitrogen Oxid. 121–141.
Packer, Chest 95:1173–1175, 1989.
Myers et al., Nature 345:161–163, 1990.
Norman and Keith, Nature 205:915–916, 1965.
Stavert and Lahnert, Inhalation Toxicology 2:53–67, 1990.
Von Nieding and Wagner, Staub–Reinhal. Luft 35:175–178, 1975.
Morel et al., Anesthesiology 66:597–604, 1987.
Morel, Circ. Res. 62:905–915, 1988.
Borland and Higenbottam Eur. Resp. J. 2:65–63, 1989.
"Asthma", Ch. 14–II, Scientific American Medicine, vol. 2, Scientific American, Inc., 1988, pp. 1–18.
Ignarro, FASEB J 3:31–36, 1989.
Frostell et al., Circulation 83:2038–2046, 1991.
Dalbly et al., Pharmaceut. Res. 5:36–39, 1988.
Buga et al., Bur. J. Pharmacol. 161:61–72, 1989.
Ishii et al., Am. J. Physiol. 261:H598–H603, 1991.
Stuart-Smith et al., J. Appl. Physiol. 69:678–685, 1990.
Suzuki et al., Clinical and Experimental Pharmacol. and Physiol. 13:39–46, 1986.
Arnold et al., Science 198:943–936, 1977.
Maron et al., Respiration 43:39–44, 1984.
Heaslip et al., J. Pharmacol. and Experimental Therapeutics 243:1018–1026, 1987.
Moncada et al., Pharmacol. Rev. 43:109–142, 1991.
Mahon, In Principles of Medical Pharmacology, Fifth Edition, 1989 B:C:Deckerinc pp. 392–397.
Gilman et al., Am. Rev. Respir. Dis. 124:549–553, 1981.
Flenley, Respiration 55:4–9, 1989.
Edwards et al., Biochem. Pharmacol. 30:2531–2538, 1981.
Garg et al., Biochem. Biophys. Res. Comm. 171:474–479, 1990.
Schmidt et al., Eur. J. Pharmacol. 122:75–79, 1986.
McNamara et al., Can. J. Physiol. Pharmacol. 58:1446–1456, 1980.
Ignarro, Annu. Rev. Pharmacol. Toxicol. 30, 535–560, 1990.
Allen and Hanbury, Product information Bulletin on Ventolin, 1990.
Allen and Hanbury, Product Information on Buclovent 1990.
Kolata, The New York Times, Jul. 2, 1991 p. C1.
Meier, The New York Times, Aug. 10, 1991, p. 48.
Boje et al., J. Pharmacol. and Experimental Therapeutics, 453:20–26, 1990.
Southern et al., FEBS 276:42–44, 1990.Garg et al., J. Clin. Invest. 83:1774–1777, 1989.
Brune et al., J. Biol. Chem. 264:8455–8458, 1989.
Curran et al. FASEB J. 5:2085, 1991.
Blomqvist et al.
Physician's Desk Reference, pp. 969–971, 2322–2323, 668–670.

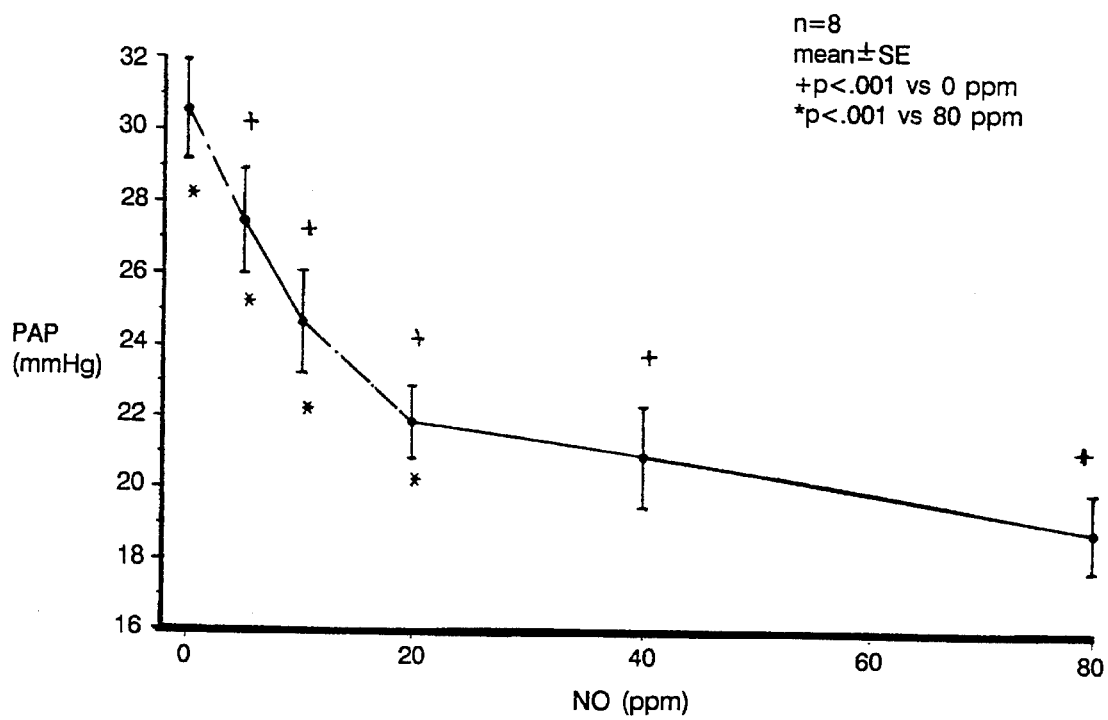
FIG. 1
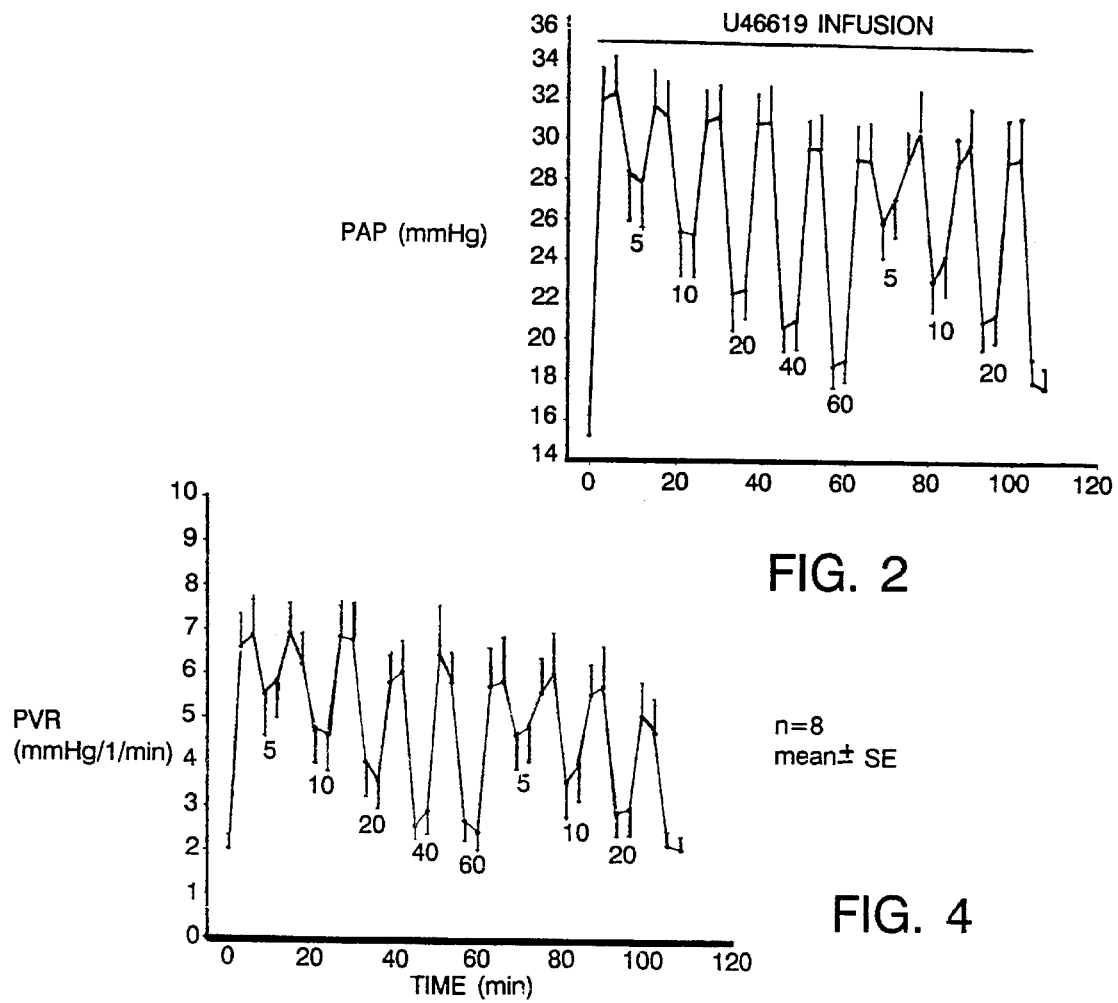
FIG. 2
FIG. 4

METHODS AND DEVICES FOR TREATING PLUMONARY VASOCONSTRICTION AND ASTHMA

This invention was made in the course of work supported by the U.S. Government, which has certain rights in the invention. This is a continuation of application Ser. No. 07/767,234, filed Sep. 27, 1991, now abandoned, which is a continuation-in-part of U.S. Ser. No. 07/622,865, filed Dec. 5, 1990 now abandoned.

BACKGROUND OF THE INVENTION

This invention relates to the treatment of pulmonary vasoconstriction and to the treatment of asthma.

Asthma is a chronic disease characterized by intermittent, reversible, widespread constriction of the airways of the lungs in response to any of a variety of stimuli which do not affect the normal lung. Estimates of the prevalence of this disease in the U.S. population range from three to six percent.

> In attempting to unravel the pathogenesis of asthma, the cellular and biochemical basis (sic) for three important features of the disease have been sought: chronic airway inflammation, reversible airflow obstruction, and bronchial hyperreactivity. Theories have pointed variously to abnormalities in autonomic nervous system control of airway function, in bronchial smooth muscle contractile properties, or in the integrity of the epithelial cell lining as features that distinguish asthmatic from normal airways . . . Evidence suggests that the normal epithelial lining functions as more than a simple barrier: epithelial cells may produce a relaxing factor that actively maintains airway patency by causing relaxation of smooth muscle. Epithelial desquamation could contribute to bronchial hyperreactivity because a lesser amount of relaxing factor would be produced.

("Asthma", Ch 14-II in *Scientific American Medicine*, Vol. 2; Scientific American, Inc.; 1988, p. 2, 4)

Drugs used to treat asthma fall generally into two categories: those which act mainly as inhibitors of inflammation, such as corticosteroids and cromolyn sodium, and those which act primarily as relaxants of the tracheobronchial smooth muscle, such as theophylline and its derivatives, beta-adrenergic agonists, and anticholinergics. Some of these bronchodilators may be administered orally, while others are generally given by intravenous or subcutaneous injection or by inhalation of the drug in an appropriate form, such as aerosolized powder (i.e., delivered in the form of a finely divided solid, suspended in a gas such as air), or aerosolized droplets (delivered in the form of a fine mist). Asthma patients typically self-administer bronchodilator drugs by means of a portable metered-dose inhaler, employed as needed to quell or prevent intermittent asthma attacks.

Conceptually analogous to the narrowing of the airways of the lung which occurs in an asthma attack, vasoconstriction is a reversible narrowing of blood vessels attributable to contraction of the smooth muscle of the blood vessels. Such vasoconstriction can lead to abnormally high blood pressure (hypertension) in the affected portion of the circulatory system.

The mammalian circulatory system consists of two separate systems, the systemic circuit and the pulmonary circuit, which are pumped in tandem by the left and right sides of the heart, respectively. The pulmonary circulation transports the blood through the lungs, where it picks up oxygen and releases carbon dioxide by equilibrating with the concentrations of oxygen and carbon dioxide gas in the alveoli. The oxygen-rich blood then returns to the left side of the heart, from whence it is distributed to all parts of the body via the systemic circulation.

The systemic circulatory system of an adult human typically has a mean systemic arterial pressure ("SAP") of 80–100 mm Hg, whereas a typical mean pulmonary arterial pressure ("PAP") is approximately 12–15 mm Hg. Normal pulmonary capillary pressure is about 7–10 mm Hg. Considering the interstitial fluid colloid osmotic pressure (14 mm Hg) and the plasma colloid oncotic pressure (28 mm Hg), as well as the interstitial free fluid pressure (1–8 mm Hg), the normal lung has a +1 mm Hg net mean filtration pressure (Guyton, *Textbook of Medical Physiology*, 6th Ed.; W. B. Saunders Co., Philadelphia, Pa. (1981), p. 295). This nearly balanced pressure gradient keeps the alveoli of a healthy lung free of fluid which otherwise might seep into the lung from the circulatory system.

An elevation of the PAP over normal levels is termed "pulmonary hypertension." In humans, pulmonary hypertension is said to exist when the PAP increases by at least 5 to 10 mm Hg over normal levels; PAP readings as high as 50 to 100 mm Hg over normal levels have been reported. When the PAP markedly increases, plasma can escape from the capillaries into the lung interstitium and alveoli: fluid buildup in the lung (pulmonary edema) can result, with an associated decrease in lung function that can in some cases be fatal.

Pulmonary hypertension may either be acute or chronic. Acute pulmonary hypertension is often a potentially reversible phenomenon generally attributable to constriction of the smooth muscle of the pulmonary blood vessels, which may be triggered by such conditions as hypoxia (as in high-altitude sickness), acidosis, inflammation, or pulmonary embolism. Chronic pulmonary hypertension is characterized by major structural changes in the pulmonary vasculature which result in a decreased cross-sectional area of the pulmonary blood vessels; this may be caused by, for example, chronic hypoxia, thromboembolism, or unknown causes (idiopathic or primary pulmonary hypertension).

Pulmonary hypertension has been implicated in several life-threatening clinical conditions, such as adult respiratory distress syndrome ("ARDS") and persistent pulmonary hypertension of the newborn ("PPHN"). Zapol et al., *Acute Respiratory Failure*, p. 241–273, Marcel Dekker, New York (1985); Peckham, *J. Ped.* 93:1005 (1978). PPHN, a disorder that primarily affects full-term infants, is characterized by elevated pulmonary vascular resistance, pulmonary arterial hypertension, and right-to-left shunting of blood through the patent ductus arteriosus and foramen ovale of the newborn's heart. Mortality rates range from 12–50%. Fox, *Pediatrics* 59:205 (1977); Dworetz, *Pediatrics* 84:1 (1989). Pulmonary hypertension may also result in a potentially fatal heart condition known as "cor pulmonale", or pulmonary heart disease. Fishman, "Pulmonary Diseases and Disorders" 2nd Ed., McGraw-Hill, New York (1988).

Attempts have been made to treat pulmonary hypertension by administering drugs with known systemic vasodilatory effects, such as nitroprusside, hydralazine, and calcium channel blockers. Although these drugs may be successful in lowering the pulmonary blood pressure, they typically exert an indiscriminate effect, decreasing not only pulmonary but also systemic blood pressure. A large decrease in the systemic vascular resistance may result in dangerous pooling of the blood in the venous circulation, peripheral hypotension (shock), right ventricular ischemia, and consequent heart failure. Zapol (1985); Radermacher, *Anaesthesiology* 68:152 (1988); Vlahakes, *Circulation* 63:87 (1981). For example, when intravenous nitroprusside was administered to 15 patients for treatment of acute pulmonary hypertension due to ARDS, mean PAP decreased from 29.6 to 24.2 mm Hg and pulmonary vascular resistance (PVR) decreased by a mean of 32%, but mean systemic arterial pressure was reduced from 89.6 mm Hg to the unacceptably low level of 70 mm Hg (Zapol et al., 1985). Intravenous nitroprusside was not recommended for clinical treatment of pulmonary hypertension, since it "markedly impairs pulmonary gas exchange by increasing $Q_{VA}/Q_T$" (the mixing of venous and arterial blood via an abnormal shunt). Radermacher (1988).

Physiological relaxation of blood vessels has been reported to result from the release of a very labile non-prostanoid endothelium-derived relaxing factor (EDRF) by endothelial cells lining the blood vessels. EDRF stimulates the enzyme guanylate cyclase within the vascular smooth muscle, with the resulting increase in cyclic GMP causing relaxation of this muscle, and thereby reversing vasoconstriction. Ignarro et al., *Proc. Natl. Acad. Sci. USA* 84:9265 (1987) and Palmer et al., *Nature* 327:524 (1987) identified the vascular smooth muscle relaxation factor released by the endothelium of arteries and veins as nitric oxide ("NO"). NO is also believed to be produced by breakdown of organic nitrates such as nitroprusside and glyceryl trinitrate. Ignarro, *Circ. Res.* 65:1 (1989); Furchgott, *FASEB J.* 3:2007 (1989). Higenbottam et al., *Ann. Rev. Resp. Dis. Suppl.* 137:107 (1988), measured the vasodilatory effects of inhaled NO in seven patients with a chronic condition termed primary pulmonary hypertension. The average PAP of these patients when breathing 40 ppm NO was 56.7 mm Hg, compared to 59.6 mm Hg when breathing air without added NO, a difference of 2.9 mm Hg, or about 6% of the difference ("ΔPAP") between the pre-treatment PAP and what would be normal PAP. Higenbottam et al. reported an average 9% reduction in PVR in these patients during inhalation of NO. No corresponding decrease in SAP was observed.

When exposed to oxygen, NO gas is unstable and undergoes spontaneous oxidation to $NO_2$ and higher oxides of nitrogen. These higher nitrogen oxides are toxic to the lung, and can in high concentrations themselves produce pulmonary edema. NO is "the most rapidly binding ligand to haemoglobin so far discovered." Meyer, *Eur. Resp. J.* 2:494 (1988). In a dilute aqueous solution exposed to oxygen, dissolved NO has a half life of less than 10 seconds due to rapid oxidation to inorganic nitrite and nitrate. Ignarro, *FASEB J.* 3:31 (1989). The Occupational Safety and Health Administration (OSHA) has set the time-weighted average inhalation limit for NO at 25 ppm for 10 hours. "NIOSH Recommendations for Occupational Safety and Health Standards," *Morbidity and Mortality Weekly Report*, Vol. 37, No. S-7, p. 21 (1988).

SUMMARY OF THE INVENTION

The invention features methods for the prevention and treatment of asthma attacks or other forms of bronchoconstriction, of acute respiratory failure, or of reversible pulmonary vasoconstriction (i.e., acute pulmonary vasoconstriction or chronic pulmonary vasoconstriction which has a reversible component), in mammals (especially humans), whereby an affected mammal is identified (by, for example, traditional diagnostic procedures, or by the diagnostic method of the invention) and caused to inhale a therapeutically-effective concentration of gaseous nitric oxide or a therapeutically-effective amount of a nitric oxide-releasing compound. A bronchdilator treatment is herein said to be "therapeutically effective" in a given patient if it reduces the patient's airway resistance by 20% or more, as measured by standard methods of pulmonary mechanics. A pulmonary vasodilatory treatment is herein said to be "therapeutically effective" in a given patient if it can induce any one or more of the following: (1) prevention of the onset of pulmonary vasoconstriction following an injury (such as aspiration or trauma) that could be expected to result in pulmonary vasoconstriction; (2) a 20% or more decrease in the patient's ΔPVR (the difference between the patient's elevated PVR and "normal" PVR, with normal PVR assumed to be below 1 mmHg.min/liter for an adult human, unless found to be otherwise for a given patient); (3) a 20% or greater decrease in the patient's ΔPAP; (4) in adults with acute or chronic respiratory failure (e.g., due to asthma or pneumonia), an improvement in arterial oxygen tensions by at least 10 mm Hg; or (5) in an infant, improved transpulmonary $O_2$ transport, as measured by a 10% or greater increase of upper body (pre-ductal) arterial $O_2$ saturation. PVR is computed by subtracting the pulmonary capillary wedge pressure (PCWP) (or left atrial pressure when available) from the mean pulmonary artery pressure (PAP), and dividing by the cardiac output (CO). PVR levels as high as 6–20 mmHg-.min/liter have been observed in cases of severe ARDS (Zapol et al., *N. Engl. J. Med.* 296: 476–480, 1977).

The methods herein disclosed are useful for preventing (if given prior to the onset of symptoms) or reversing acute pulmonary vasoconstriction, such as may result from pneumonia, traumatic injury, aspiration or inhalation injury, fat embolism in the lung, acidosis, inflammation of the lung, adult respiratory distress syndrome, acute pulmonary edema, acute mountain sickness, asthma, post cardiac surgery acute pulmonary hypertension, persistent pulmonary hypertension of the newborn, perinatal aspiration syndrome, hyaline membrane disease, acute pulmonary thromboembolism, heparin-protamine reactions, sepsis, asthma, status asthmaticus, or hypoxia (including that which may occur during one-lung anesthesia), as well as those cases of chronic pulmonary vasoconstriction which have a reversible component, such as may result from chronic pulmonary hypertension, bronchopulmonary dysplasia, chronic pulmonary thromboembolism, idiopathic or primary pulmonary hypertension, or chronic hypoxia. Nitric oxide gas is preferably administered to a mammal with pulmonary vasoconstriction or asthma in accordance with one or more of the following:

(a) administration for at least three minutes (more preferably at least six minutes);

(b) administration in the absence of tobacco smoke;

(c) the inhaled concentration of nitric oxide is at least 1 ppm, more preferably at least 20 ppm, and most preferably at least 80 ppm, with the concentration not exceeding 180 ppm of nitric oxide (such concentration being monitored by a technique such as chemiluminescence);

(d) the nitric oxide is inhaled as a mixture including nitric oxide, oxygen ($O_2$), and nitrogen ($N_2$) gases, most preferably having an $F_IO_2$ (i.e., proportion of $_2$ gas, by volume) of 0.21–0.99, the proportion of $O_2$ in air being 0.21; and (e) the concentration of $NO_2$ is monitored and kept within safe limits (e.g., less than 1 ppm). Inhalation of gaseous nitric oxide represents a major advance in asthma therapy, since the gas has no particles or droplets to disperse and transport to the respiratory tract. Gases have long free-diffusion pathways, bypass obstructions (such as constricted airways) readily, and dissolve directly in tissue without causing impaction bronchospasm. The beneficial effect of NO gas on bronchial smooth muscle tone is observed immediately following inhalation, making NO a useful first defense against bronchospasm that can be followed, if desired, by inhalation of longer-acting agents.

Inhaled nitric oxide also provides a convenient means for diagnosing the reversibility of chronic pulmonary vasoconstriction in a mammal (in particular, a human): the affected mammal is caused to inhale gaseous nitric oxide, and any changes in PAP and cardiac output before and during NO inhalation are noted. If the PAP decreases upon inhalation of NO while the cardiac output remains constant or increases, or if the $\Delta$PVR decreases by a significant amount (e.g., at least 20%, or preferably at least 30%), then the mammal's chronic pulmonary vasoconstriction would have been shown to have a reversible component potentially treatable with gaseous NO or with NO-releasing compounds (or with other types of vasodilators) administered systemically or by inhalation therapy.

Alternatively, a mammal (in particular, a human) with or at risk of developing bronchoconstriction (e.g., asthma) or reversible pulmonary vasoconstriction may be treated with a therapeutically-effective amount of a nitric oxide-releasing compound. Known nitric oxide-releasing compounds (also referred to as nitric oxide-donor or nitric oxide-generating compounds) useful in the methods and devices of the invention can be divided into three categories: (a) nitroso or nitrosyl compounds (e.g., S-nitroso-N-acetylpenicillamine, S-nitroso-L-cysteine, and nitrosoguanidine) characterized by an—NO moiety that is spontaneously released or otherwise transferred from the compound under physiological conditions such as obtain in the lung; (b) compounds in which NO is a ligand on a transition metal complex, and as such is readily released or transferred from the compound under physiological conditions (e.g., nitroprusside, NO-ferredoxin, or an NO-heme complex); and (c) nitrogen-containing compounds which are metabolized by enzymes endogenous to the respiratory and/or vascular system to produce the NO radical (e.g., arginine, glyceryl trinitrate, isoamyl nitrite, inorganic nitrite, azide, and hydroxylamine). Such types of nitric oxide-releasing compounds and methods for their synthesis are well known in the art (see, for example, the following publications, each of which is incorporated by reference herein: Edwards et al., Biochemical Pharmacology 30:2531–2538, 1981; Schmidt and Kukovetz, Eur. J. Pharmacol. 122:75–79, 1986; Curran et al., FASEB J. 5:2085–2092, 1991; Southern et al., FEBS Lett. 276:42–44, 1990; Garg et al., J. Clin. Invest. 83:1774–1777, 1989; Garg et al., Biochem. Biophys. Res. Commun. 171:474–479, 1990; Boje et al., J. Pharmacol. Exp. ther. 253:20–26, 1990; Bruene et al., J. Biol. Chem. 264:8455–8458, 1989; and McNamara et al., Can. J. Physiol. Pharmacol. 58:1446–1456, 1980). A compound known or believed to be such an NO-releasing compound can be directly tested for its efficacy in the method of the invention by the use of animal models in one of the in vivo assays described below. Alternatively, such a compound may first be screened for its ability to stimulate guanylate cyclase, the enzyme to which NO binds and thereby exerts its biological activity, in an in vitro assay such as is described by Ishii et al., Am. J. Physiol. 261:H598-H603, 1991. The stability of the compound during storage can be ascertained, for example, by subjecting the stored compound to serial measurements of UV light absorption at a wavelength characteristic of the NO-containing compound (typically 595 nm).

The nitric oxide-releasing compound selected for use in the method of the invention may be administered as a powder (i.e., a finely divided solid, either provided pure or as a mixture with a biologically-compatible carrier powder, or with one or more additional therapeutic compounds) or as a liquid (i.e., dissolved or suspended in a biologically-compatible liquid carrier, optionally mixed with one or more additional therapeutic compounds), and can conveniently be inhaled in aerosolized form (preferably including particles or droplets having a diameter of less than 10 μm). Carrier liquids and powders that are suitable for inhalation are commonly used in traditional asthma inhalation therapeutics, and thus are well known to those who develop such therapeutics. The optimal dosage range can be determined by routine procedures by a pharmacologist of ordinary skill in the art. For example, a useful dosage level for SNAP would be from 1 to 500 μmoles (preferably 1–200 μmoles) per inhaled dose, with the number of inhalations necessary varying with the needs of the patient.

Also within the invention is an inhaler device (preferably sufficiently lightweight to be considered portable, i.e. less than 5 kg, and more preferably less than 1 kg) suitable for the treatment or prevention of bronchoconstriction or pulmonary vasoconstriction, which device may be of a design similar to those inhalers currently available for the treatment of asthma attacks, and which contains either or both of (a) pressurized nitric oxide gas, and (b) a nitric oxide-releasing compound. Such a device would typically include a vessel containing pressurized gas containing at least 1 ppm (preferably at least 5 ppm, more preferably at least 40 ppm, and most preferably at least 100 ppm) nitric oxide; a housing defining a lumen and optionally a chamber containing an inhalable pharmaceutically-active agent, which chamber is in communication with the lumen; and a mechanism, such as a release valve operable by depressing the valve, for controllably releasing the gas into lumen or the chamber (thereby suspending the pharmaceutically-active agent in the released gas); the lumen being configured to route the released gas (and suspended agent, if any) into the respiratory system of a patient. The lumen may include a tube, mask, or rebreathing chamber such as those typically found on presently available inhaler devices. The device may also have a mechanism for optionally releasing the gas into the lumen in a manner that bypasses the compound in the chamber, thereby permitting the patient to first be treated with the nitric oxide-containing gas alone, followed if necessary by a dose of the pharmaceutically-active agent suspended in nitric oxide-containing gas. The pharmaceutically-active agent may, for example, be a bronchodilator compound in liquid or solid form. Such a compound could be any compound currently known or subsequently discovered to be effective in counteracting bronchconstriction. Types of drugs known to be useful in the inhalation treatment of asthma include cromolyn sodium; anticholinergic agents (such as atropine and ipratropium bromide); $\beta_2$ agonists (such as adrenaline, isoproterenol, ephedrine, salbutamol, terbutaline, orciprenaline, fenoterol, and isoetharine), methylxanthines (such as theophylline); calcium-channel blockers (such as verapamil); and glucocorticoids (such as prednisone, prednisolone, dexamethasone, beclomethasone dipropionate, and beclomethasone valerate), as described in Ch. 39 of *Principles of Medical Pharmacology, Fifth Edition*, Kalant and Roschlau, Ed. (B. C. Decker Inc., Philadelphia, 1989), herein incorporated by reference. The use and dosage of these and other effective bronchodilator drugs in inhalation therapy are well known to practitioners who routinely treat asthmatic patients.

In addition to or instead of the above-described bronchodilator drugs, the inhaler device of the invention may also contain an NO-releasing compound (such as SNAP, S-nitrosocysteine, nitroprusside, nitrosoguanidine, glyceryl trinitrate, isoamyl nitrite, inorganic nitrite, azide, or hydroxylamine), which would provide a long-lasting bronchodilating effect to complement the immediate effects obtained by inhaling NO gas. NO-releasing compounds could be tested for their usefulness in treating asthma attacks and/or reversible pulmonary vasoconstriction by in vitro and in vivo assays well known to practitioners who routinely develop therapies for these conditions. Criteria for selecting a therapeutically-useful NO-donor compound will include its stability in storage prior to inhalation and its ability to decompose to release NO at a therapeutically beneficial rate upon deposition in the appropriate part of the respiratory tract. For example, S-nitroso-N-acetylpenicillamine ("SNAP") has been shown to be stable in its solid form, but under physiological conditions (such as in the film of physiological fluid on the surface of the bronchiolar or alveolar lumen), the compound readily decomposes to release NO (Ignarro, *Circ. Res.*, 1989). The nitric-oxide-releasing compound could be provided in powder form, or it could be dissolved or suspended in a biologically-compatible liquid carrier. The device of the invention could be a portable inhaler similar to those typically used by persons with asthma, but which contains a pressurized mixture of nitrogen gas (or another inert gas) and nitric oxide gas (instead of or in addition to an inert, liquified propellant such as a fluorocarbon, e.g., freon). Alternatively, the pharmaceutically-active agent included in the device of the invention may be an antimicrobial agent, or a surfactant suitable for the treatment of hyaline membrane disease.

In another preferred embodiment, the device of the invention would include

- a vessel containing a nitric oxide-donor compound (e.g., in liquid or solid form) suspended in a liquified propellant;
- a housing defining (a) a port to which the vessel is mounted and (b) a lumen in communication with the port; and
- a mechanism for controllably releasing the propellant from the vessel into the lumen, thereby releasing the compound from the vessel into the lumen; such lumen being configured to route the compound into the respiratory system of a person.

Alternatively, the device could include

- a vessel containing a compressed or liquified propellant gas (optionally including at least 1 ppm nitric oxide gas);
- a housing defining (a) a chamber containing a nitric oxide-donor compound and (b) a lumen in communication with the chamber; and
- a mechanism for controllably releasing the gas from the vessel into the chamber (for example, in preset doses), thereby suspending the compound in the gas; the lumen being configured to route the compound into the respiratory system of a person. The device would preferably be a metered-dose inhaler similar to one of the many designs currently available, which would automatically dispense, in a puff intended for inhalation in a single or multiple breaths, a set amount of the bronchodilator substance (including the NO gas and/or the NO-releasing compound) when activated by the patient in need of treatment. A single device may optionally be designed to deliver, at the discretion of the patient, NO gas (diluted in an inert gas such as $N_2$), with or without the solid or liquid bronchodilator substance. Such a "two-stage" design would permit the patient to reserve use of the longer-acting solid or liquid bronchodilator substance until his or her airways had been opened by the puff of gaseous NO in $N_2$, thus cutting down on the dosage of the solid or liquid pharmaceutical necessary for lasting benefit. The optimal level of NO and/or NO-releasing compound to be dispensed can be determined by a pharmacologist using methods such as those set forth herein. It is expected that a useful inhaled dose of NO gas for the treatment of asthma would be at least 10 ppm for ½ min., and preferably from 100 to 300 ppm for one min, which could be achieved, for example, by packaging the compressed NO to be released from the nozzle of the inhaler (or into a rebreathing tube or mask) at at least 1,000 ppm in a mixture with $N_2$. Self-administered treatment of pulmonary vasoconstriction might require a concentration of 1,000 to 30,000 ppm NO in $N_2$ at the nozzle, to deliver 5 ml into a 500 ml tidal volume, in order to result in an effective level of 10 to 300 ppm NO in the lungs of the patient.

NO gas could also be used to bronchodilate and thereby improve the distribution of other agents administered by inhalation. Examples of such agents frequently administered by inhalation include antibiotics and other antimicrobials (e.g., pentamidine for treatment of pneumocytis pneumonia), and surfactant agents such as are given to infants with hyaline membrane disease.

The invention described herein provides a simple, safe, rapid, and efficacious treatment or preventative therapy for asthma attacks, for acute respiratory failure (e.g., ARDS or pneumonia), and for vasoconstrictive pulmonary hypertension. In one embodiment of the invention, a portable inhaler equipped with a cartridge of compressed NO or an aerosol container of an NO-releasing compound in powder or liquid form could be used to administer inhalation therapy for asthma or for pulmonary vasoconstriction either in a hospital setting or in an emergency field situation. Such an inhaler can be carried, for example, by a person at risk of developing hypoxia, such as a mountain climber, or by ski patrol personnel who can administer the inhalation therapy on an emergency basis to skiers stricken with hypoxic pulmonary edema. Similar inhalers containing bronchodilating agents are routinely carried by asthmatic individuals. In another embodiment of the invention, a cartridge of compressed NO or an aerosol container of an NO-releasing compound could be connected to a ventilation circuit and used to treat and stabilize newborn infants with PPHN during transport from the hospital where delivery occurred to one with an intensive care unit, or used to treat pneumonia and ARDS by mask therapy or mechanical ventilator in a hospital or emergency room.

When an NO-releasing compound is inhaled in solid or liquid form, the particles or droplets are deposited throughout the respiratory system, with larger particles or droplets tending to be deposited near the point of entry (i.e., in the mouth or nose) and smaller particles or droplets being carried progressively further into the respiratory system before being deposited in the trachea, bronchi, and finally the alveoli. (See, e.g., Hounam & Morgan, "Particle Deposition", Ch. 5 in *Respiratory Defense Mechanisms, Part 1*, Marcel Dekker, Inc., New York; ed. Brain et al., 1977; p.

125.) A particle/droplet diameter of 10 μm or less is recommended for use in the method of the invention. Where pulmonary vasoconstriction is the target condition, particle/droplet size should in general be of a size distribution appropriate for deposition in the alveoli (i.e., averaging less than 5 μm, with an ideal size around 1–3 μm), while treatment of an asthma attack, which affects mainly the bronchi, would preferably be accomplished using an inhaled particle/droplet size of approximately 2–8 μm. Determination of the preferred carrier (if any), propellant (which may include NO diluted in an inert gas such as $N_2$) design of the inhaler, and formulation of the NO-releasing compound in its carrier are well within the abilities of those of ordinary skill in the art of devising routine asthma inhalation therapies. The portable inhaler could contain a canister of compressed NO, preferably in an inert carrier gas such as $N_2$, or any alternative means of providing NO gas. Alternatively, or in addition, the inhaler could contain an NO-releasing compound either mixed in dry form with a propellant or held in a chamber separate from the propellant, or mixed with a liquid carrier capable of being nebulized to an appropriate droplet size, or in any other configuration known to those skilled in portable inhaler technology. A few of the several types of inhaler designs that have been developed to date are discussed in, for example, U.S. Patent Nos. 4,667,668; 4,592,348; 4,534,343; and 4,852,561, each of which patents is herein incorporated by reference. Other inhaler designs are described in the *Physicians' Desk Reference, 45th Edition*, Edward R. Barnhart, Publisher (1991). Each of these and other aerosol-type inhalers can be adapted to accommodate the delivery of NO gas and/or NO-releasing compounds. Also useful for delivering an NO-releasing compound formulated in dry powder form is a non-aerosol-type inhaler device such as that developed by Allen & Hanburys, Research Triangle Park, North Carolina.

Since NO gas which enters the bloodstream is rapidly inactivated by combination with hemoglobin, the bronchodilatory effects of inhaled NO are limited to the ventilated bronchi and the vasodilatory effects of inhaled NO are limited to those blood vessels near the site of NO passage into the blood stream: i.e., pulmonary microvessels. Therefore, an important advantage of both the bronchodilating and the pulmonary vasodilating methods of the invention is that one can selectively prevent or treat bronchospasm and/or pulmonary hypertension without producing a concomitant lowering of the systemic blood pressure to potentially dangerous levels. The invention allows for effective reversal of pulmonary hypertension without the risk of underperfusion of vital organs, venous pooling, ischemia, and heart failure that may accompany systemic vasodilation. Such isolated pulmonary vasodilation is also important in treating PPHN in newborn infants, as systemic vasodilation aggravates the undesired mixing of oxygenated and de-oxygenated blood through the ductus arteriosus or the foramen ovale of newborns. Furthermore, by concomitantly bronchodilating and increasing blood flow to ventilated alveoli, the methods of the invention improve oxygen transport in patients with asthma or acute repiratory failure, providing an added benefit not seen with typical bronchodilatory therapies.

The invention also advantageously provides a simple, rapid, non-invasive method of diagnosing those forms of chronic pulmonary hypertension which will be responsive to NO inhalation therapy. These patients may benefit from long-term inhalation therapy by the method of the invention, or from chronic systemic treatment with NO-producing vasodilatory drugs, such as nitroprusside and glyceryl trinitrate, with calcium channel blockers, or with other types of vasodilators.

Other features and advantages of the invention will be apparent from the following detailed description, experimental information, and claims.

DETAILED DESCRIPTION

The drawings are first described.

Drawings

FIG. 1 is a graph of the NO dose response curve for lambs with U46619-induced pulmonary vasoconstriction.

FIG. 2 is a graph showing the effects of inhaling various concentrations of NO mixed with $O_2$, alternating with periods of breathing 60–70% $O_2$ without added NO, on the PAP of lambs receiving continuous infusions of U46619.

FIG. 4 is a graph showing the effects of inhaling various concentrations of NO mixed with $O_2$, alternating with periods of breathing 60–70% $O_2$ without added NO, on the pulmonary vascular resistance (PVR) of lambs receiving continuous infusions of U46619.

No Inhalation Therapy for Pulmonary Vasoconstriction

Figure 3:
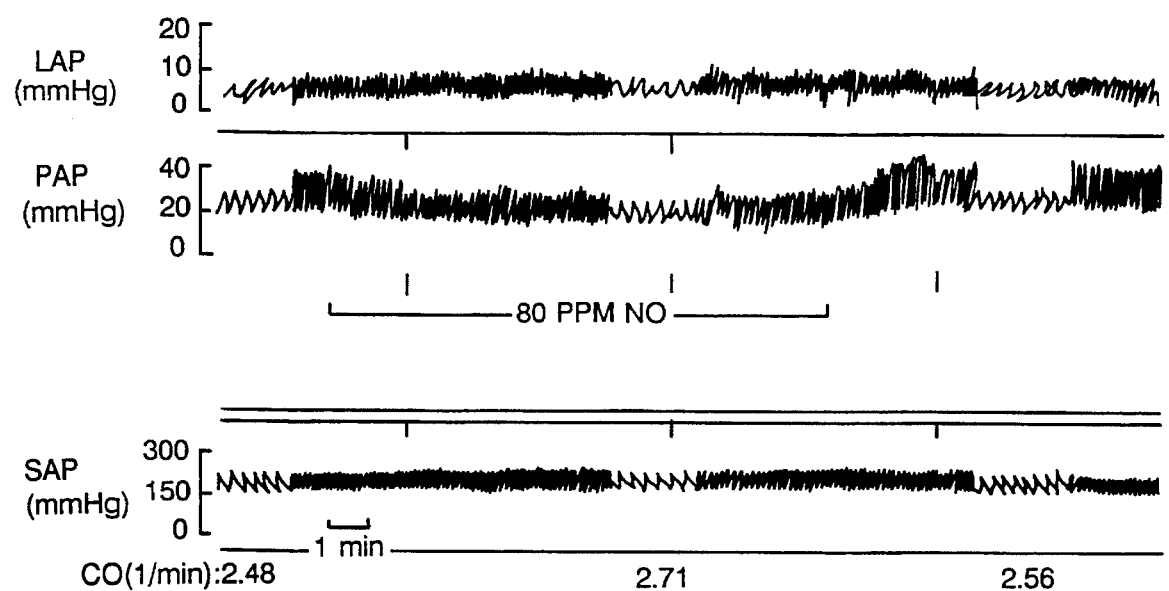
FIG. 3 is a strip chart recording illustrating the effect of causing a lamb with U46619-induced pulmonary vasoconstriction to inhale 80 ppm NO for 6 minutes.

The invention provides for the first time a simple, rapid, selective, and efficacious method of treating or preventing both acute and certain forms of chronic pulmonary hypertension, without concomitantly lowering the systemic blood pressure of the patient. Pulmonary hypertension is a widespread clinical manifestation, afflicting diverse groups of patients. Use of inhaled NO is currently envisioned for, but not limited to, patients afflicted with or at risk of developing the following: ARDS, pneumonia, asthma, acute pulmonary edema, acute or chronic hypoxia, alveolar hypoventilation states, high altitude pulmonary edema ("mountain sickness"), PPHN, hyaline membrane disease, acidosis, idiopathic pulmonary hypertension, sepsis, pulmonary thromboembolism, cor pulmonale secondary to pulmonary hypertension, perinatal aspiration syndrome, and acute pulmonary vasoconstriction in response to protamine reversal of heparin anticoagulation ("heparin-protamine reaction").

Method for Administration

Compressed NO gas may be obtained from a commercial supplier such as Air Products and Chemicals, Inc. (Allentown, Pa.) or Airco (Murray Hill, N.J.), typically as a mixture of 200–800 ppm NO in pure $N_2$ gas. It is vital that the NO be obtained and stored as a mixture free of any contaminating $O_2$ or higher oxides of nitrogen, as such higher oxides of nitrogen (which can form by reaction of $O_2$ with NO) are potentially harmful to lung tissues. If desired, purity of the NO may be demonstrated with chemiluminescence analysis, using known methods, prior to administration to the patient. The NO-$N_2$ mixture may be blended with air or $O_2$ through, for example, calibrated rotameters which have previously been validated with a spirometer. The final concentration of NO in the breathing mixture may be verified with a chemical or chemiluminescence technique well known to those in the field (e.g., Fontijin et al., *Anal. Chem.* 42:575–579, 1970). Any impurities such as $NO_2$ can be scrubbed by exposure to NaOH solutions, baralyme, or sodalime. As an additional control, the $F_iO_2$ of the final gas mixture may also be assessed. If desired, the ventilator may have a gas scavenger added to the expiratory outlet to ensure that significant amounts of NO will not escape into the adjacent environment.

In a hospital or emergency field situation, administration of NO gas could be accomplished, for example, by attaching a tank of compressed NO gas in $N_2$, and a second tank of oxygen or an oxygen/$N_2$ mixture, to an inhaler designed to mix two sources; by controlling the flow of gas from each source, the concentration of NO inhaled by the patient can be maintained at an optimal level.

NO may be administered to mammals suspected of having acute pulmonary vasoconstriction, at a concentration of from 1 ppm to 40 ppm in air, pure oxygen, or another suitable gas or gas mixture, for as long as needed. The concentration can be increased to 80 to 180 ppm for short periods of time: e.g., 5 min at 180 ppm NO, when an immediate dramatic effect is desired.

Assessment of Pulmonary Vascular Pressure and Flow

Pulmonary artery pressure is most accurately monitored with a flow-directed pulmonary artery (PA) catheter, placed percutaneously via a vein of a patient under local anaesthesia; PA flow is usually measured using thermaldilution via such a PA catheter. Alternative methods exist for indirect, non-invasive monitoring: e.g., cardiac ultrasound, monitoring of systolic time intervals, and range-gated doppler techniques. These alternative methods of monitoring may be superior whenever catheterization is impracticable, such as in emergency situations, in patients who are not good candidates for catheterization, or in on-going treatments or established protocols.

Pharmacological Effect of Nitric Oxide

It is likely that inhaled NO acts by diffusing into the vascular space adjacent to the alveoli and causing relaxation of pulmonary vascular smooth muscle, thus permitting an increase in pulmonary blood flow and gas exchange. Preliminary evidence obtained in five humans with severe acute respiratory failure demonstrates that NO (approximately 20 ppm) inhaled during mechanical ventilation for periods up to one month reduces both pulmonary arterial pressure and $Q_{VA}/Q_T$ (the right-to-left shunt: a measure of pulmonary oxygen transport inefficiency), thereby producing a marked increase of the patients' blood oxygen levels. This suggests that NO vasodilation occurs only in ventilated alveoli and not in non-ventilated or collapsed alveoli, in marked contrast to results observed following intravenously administered vasodilators such as nitroprusside. By localizing delivery of NO in a gaseous form directly to the lungs, the dissolved NO can immediately exert its pharmacological effect on target vascular smooth muscle, prior to inactivation of the NO by binding to hemoglobin. At the same time, the rapid binding of NO to hemoglobin ensures that any vasodilatory action of inhaled NO is solely a local or selective effect in the blood vessels of the lung, with no concomitant vasodilation downstream in the systemic circulation.

Diagnosis and Treatment of Chronic Pulmonary Hypertension

Chronic pulmonary hypertension is characterized by the obstruction or structural narrowing of blood vessels in the lungs. To the extent that the chronic condition of a particular patient is caused or aggravated by spastic constriction of pulmonary vascular smooth muscle or bronchoconstriction, it may be at least partially ameliorated by inhalation of NO: such cases susceptible to treatment with NO, and potentially with systemic vasodilators, are readily identified by their response to a brief NO inhalation test (e.g., six minutes inhaling 80 ppm NO alternating with six minutes inhaling air without added NO, repeated for two to four cycles), while measuring PAP, PCWP, and cardiac output. Responsive cases (e.g., those in which the PVR is reduced by 20% or more) can then be treated either with portable NO inhalation therapy, with inhalation of NO-releasing compounds in solid or liquid form, or with NO-releasing systemic vasodilatory drugs such as glyceryl trinitrate or other non-specific systemic dilators (e.g., calcium channel blockers).

NO-Releasing Compound Inhalation Therapy for Pulmonary Vasoconstriction

The finding that inhalation of gaseous NO can effectively reverse certain forms of pulmonary vasoconstriction suggests yet another mode of inhalation therapy for pulmonary vasoconstriction, wherein an NO-releasing compound, rather than gaseous NO, is inhaled. This method will provide a longer-lasting beneficial effect than briefly inhaling gaseous NO, as the deposited NO-releasing compound would slowly release NO over a relatively long period of time. Formulation and dosage of a selected NO-releasing compound can be determined without undue experimentation by one of ordinary skill in the art. As one example, a typical single inhaled dose of an NO-releasing compound such as S-nitroso-N-acetylpenicillamine (SNAP) or S-nitrosocysteine in dry powder form could range from 60 to 650 µg of the active compound (NO) per kg bodyweight, for approximately an hour of dilation. In sheep with experimentally-elevated PA pressure, inhalation of SNAP at 1.3 mg/kg produced a prolonged reduction in PA pressure.

Inhalation Therapy for Asthma

Like pulmonary vasoconstriction, spastic constriction of the airways such as occurs in asthma attacks can be reversed by inhalation of either gaseous NO or an NO-releasing compound in solid or liquid form. Gaseous NO would have the advantage of rapid diffusion without particles, and would also vasodilate the bronchodilated region, thereby improving arterial oxygen tensions. Administration would be as described above, and would typically be initiated upon the onset of an attack or when an attack is thought to be imminent. If chronic bronchodilation of a given patient is needed, the patient's entire ambient atmosphere could be charged with NO gas at a low dose (at a high gas turnover rate), such as with a mask or tent.

Inhalation Devices

Figure 17:
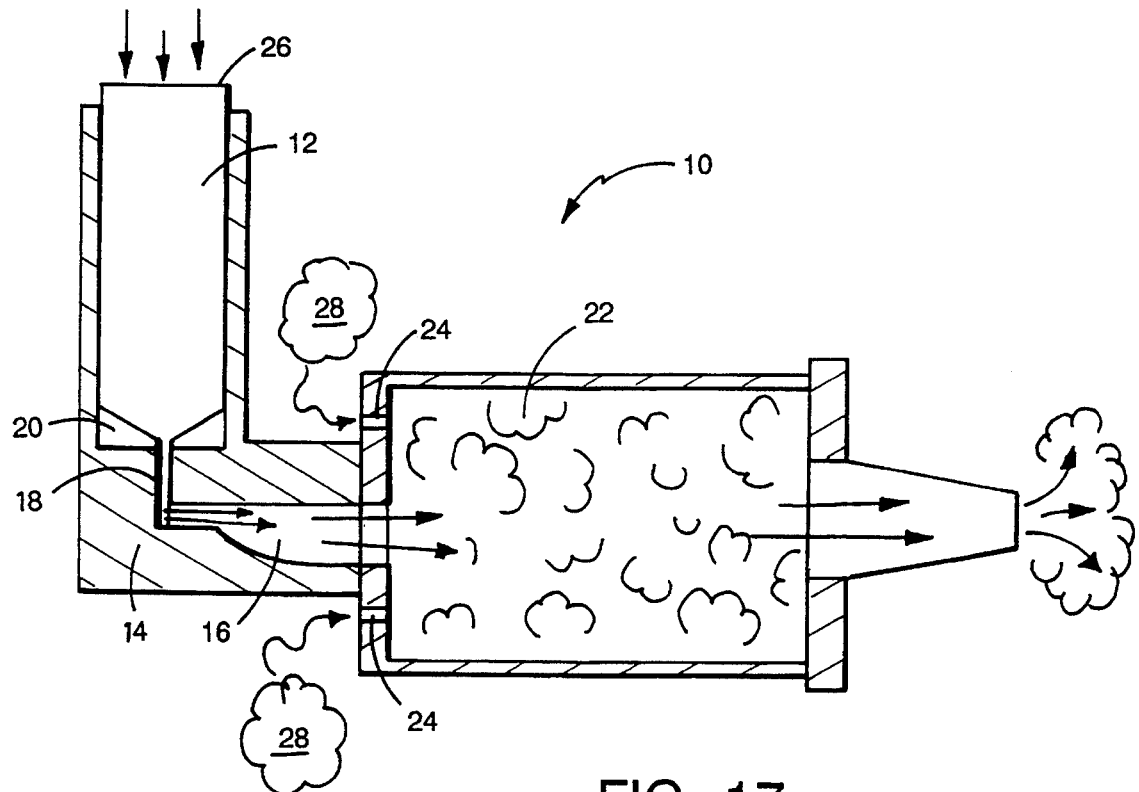
FIG. 17 is a cross-sectional view of one embodiment of the inhaler device of the invention.

The inhalation therapy of the invention is preferably administered by the use of one of the inhalation devices of the invention. One of such devices 10 is illustrated in cross-section in FIG. 17, which shows a housing 14 defining a chamber 20 in communication with a lumen 16; a vessel 12 containing pressurized gas having at least 1 ppm nitric oxide dissolved in a liquified propellant or compressed inert gas, and/or which contains a suspension of a solid or liquid nitric oxide-donor therapeutic agent, which vessel 12 is slidably mounted in the chamber 20; a pressure-activated valve mechanism 18 for controllably releasing the pressurized contents of the vessel 12 into the lumen 16; and, constituting one end of the lumen 16, a rebreathing chamber 22 having one-way valves 24 through which air 28 can enter the rebreathing chamber 22, but through which the therapeutic gas cannot escape. A patient utilizes the device by pushing the upper end 26 of the vessel 12 which protrudes from the housing 14, thereby sliding the vessel 12 down into the chamber 20 and depressing the valve mechanism 18. This causes the pressurized contents of the vessel 12 to be released into the lumen 16 and the rebreathing chamber 22. The patient then inhales a portion of the contents of the rebreathing chamber 22, drawing air 28 through the one-way valve 24 into the rebreathing chamber 22 to replace the portion of the contents inhaled by the patient. A single dose of the therapeutic agent released from the vessel 12 into the rebreathing chamber 22 may take several breaths to be sufficiently inhaled by the patient. The total weight of this device would be less than 200 grams, so that it is readily portable.

Figure 18:
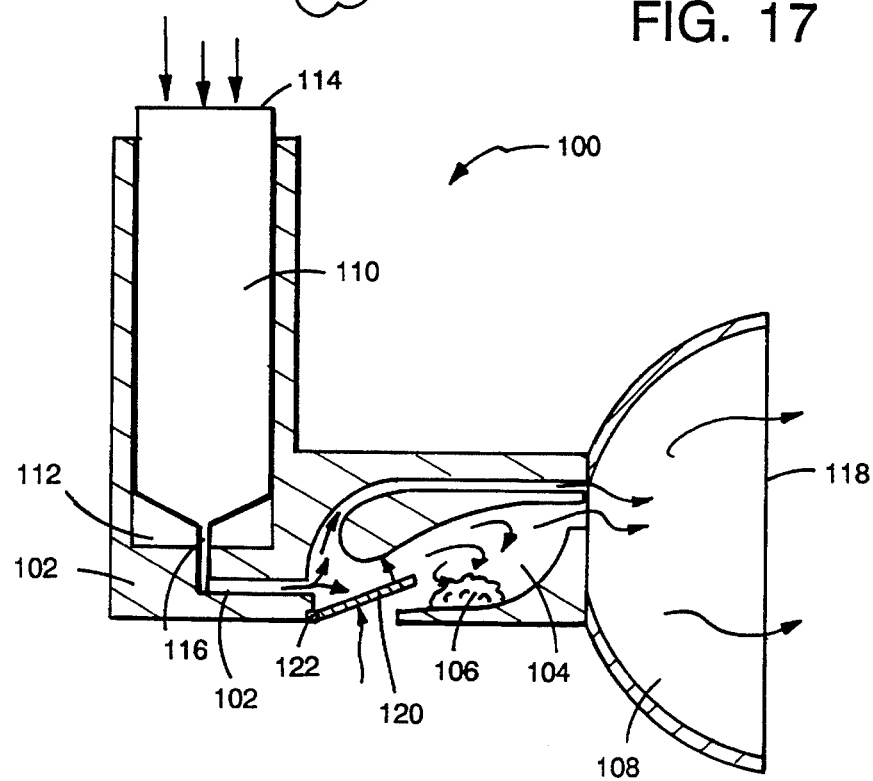
FIG. 18 is a cross-sectional view of a second embodiment of the inhaler device of the invention.

In another preferred embodiment 100, illustrated in FIG. 18, the housing 102 defines (a) a first chamber 104 containing an inhalable pharmaceutically-active compound 106 and (b) a lumen 108 in communication with the first chamber 104. A vessel 110 containing pressurized gas or liquified propellant comprising at least 1 ppm nitric oxide is slidably mounted in a second chamber 112 of the housing 102, such that pressure applied to the top of the vessel 114 causes a pressure-release valve located at the bottom of the vessel 116 to be depressed against the wall of the housing 102, thereby opening the valve and releasing a portion of the pressurized contents of the vessel 110 into the first chamber 104. The pressurized gases so released mix with and suspend as an aerosolized mist the compound 106 in the first chamber 104. This mist is then inhaled by the patient through the open mouthpiece end 118 of the lumen 108. At the option of the patient, tab 120 on spring-loaded hinge 122 may be manually depressed by the patient prior to and during the opening of the pressure release valve 116; this acts to temporarily close off the first chamber 104 from the path of the released pressurized gases, which then escape directly into the lumen 108, bypassing the first chamber 104 in which is located the therapeutic agent 106. By first inhaling the nitric oxide-containing gas without the therapeutic compound 106 suspended therein, the patient's airways are sufficiently opened to maximize the potential benefits of subsequently inhaling the more slowly-acting solid or liquid therapeutic compound 106, so the patient then releases tab 120, again pushes down on the top of the vessel 114 to open valve 116, and inhales from the open end mouthpiece 118 of lumen 108 the therapeutic compound 106 suspended in the pressurized gases so released.

Experimental Information

The applicants submit the following experimental animal and human data and approved protocol for human studies as examples in support of the application.

1. PULMONARY VASODILATION

A. Administration of gaseous nitric oxide to lambs i. Methods

Surgical preparation of the animal model:

Eight Suffolk lambs weighing 25–35 kg underwent a sterile thoracotomy in order to place a left atrial line, tracheostomy and femoral artery line under general endotracheal anesthesia with halothane/oxygen three days before study. After three days of recovery the lambs underwent sterile placement of a 7 French thermal dilution pulmonary artery monitoring catheter under local anesthesia.

Study conditions:

Awake unanesthetized lambs were studied in order to avoid general anesthesia which can blunt hypoxic vasoconstriction. Lambs were placed in a Babraham cage and allowed to drink and eat ad lib. Two studies were performed 2 days apart on each of six lambs. After the study the lambs were sacrificed with an overdose of barbiturate and their lungs were fixed, stained and examined by light microscopy for pathological changes.

Administration of NO to lambs with pulmonary vasoconstriction induced with U46619:

On the first study day lambs breathing 60–70% oxygen were given an infusion of a potent pulmonary vasoconstrictor, the stable endoperoxide analog (5Z, 9α, 13E, 15S)-11, 9-(Epoxymethano)prosta-5,13-dien-1-oic acid (U46619, The Upjohn Company, Kalamazoo, Mich.) of thromboxane at a rate of 0.4–0.8 µg/kg/min. The tracheostomy was connected to a non-rebreathing circuit consisting of a 5 liter reservoir bag and one way valves to isolate inspired from expired gas. Expired gas was scavenged and discarded. The inspired gas was a precise mixture of oxygen and nitrogen immediately diluted with NO to produce the correct inspired concentration. Using volumetrically calibrated flowmeters, varying quantities of NO were mixed with $N_2$ to obtain the desired inspired NO concentration at an inspired oxygen concentration ($F_iO_2$) of 0.6–0.7. The reservoir bag was emptied after each level of NO inhalation. The residence half time of NO in the gas reservoir was 15 seconds or less to minimize conversion to $NO_2$. NO was obtained from Air Products and Chemicals, Inc., Allentown, Pa. as a mixture of 235 ppm NO in pure $N_2$. Chemiluminescence analysis demonstrated less than 12 ppm $NO_2$ in this mixture. Fontijin, *Anal. Chem.* 27:1903 (1981).

A pulmonary vasodilator dose response curve plotting changes in PAP as a function of inhaled NO concentration during U46619 infusion was produced for eight lambs breathing a series of increasing $NO/O_2$ mixtures of 5, 10, 20, 40, and 80 ppm NO for six minutes (FIG. 1). Each level of NO exposure was followed by six minutes of breathing the oxygen mixture without NO (FIG. 2). A second exposure to NO was examined for similar periods. Subsequently, a control period breathing the oxygen mixture was studied six minutes after ceasing U46619 infusion. At each three and six minute time period after administering or discontinuing NO during the study, we measured mean and phasic pulmonary artery pressure (PAP), left atrial pressure (LAP), systemic arterial pressure (SAP) and central venous pressure (CVP). All pressures were recorded on a Hewlett Packard multi-channel strip chart recorder with transducers zeroed to atmospheric pressure at the mid point of the thorax (e.g., see FIG. 3). Cardiac output (CO) was measured by thermal dilution as the average of two determinations injecting 5 ml of 0° C. Ringers lactate. Pulmonary vascular resistance (PVR) and systemic vascular resistance (SVR) were computed by standard formulae; PVR measured at each inhaled NO concentration is shown in FIG. 4. Appropriate statistical analyses were performed, and all data were expressed as mean ±standard error.

Administration of NO to lambs with pulmonary vasoconstriction induced by hypoxia:

Five awake lambs were studied during a period of breathing a hypoxic gas mixture to induce acute hypoxic pulmonary hypertension. Three lambs were excluded due to sepsis and heart failure. Hemodynamic monitoring techniques similar to those described above were used. We employed a non-rebreathing circuit containing a 25 liter reservoir bag and the $F_iO_2$ was reduced to 0.06–0.08 to produce a mean PAP near 25 mm Hg at a $P_aO_2$ near 30 mm Hg. Either 40 or 80 ppm NO was then added to the inspired gas mixture. Total gas flows were maintained at 35 l/min to prevent rebreathing due to hyperventilation. The inspired $F_iO_2$ was monitored with an electrode (model 5590, Hudson Co., Temecala, Calif.) and pure $CO_2$ was added to the inspired gas to maintain the end tidal $CO_2$ concentration at 4.5–6%. Measurements of central hemodynamics and gas exchange were obtained at baseline, during hypoxia, and at 3 and 6 minutes of NO breathing during hypoxia. Comparisons were performed using paired t-tests.

ii. Results

Two control lambs with no drug infusion breathed 80 ppm NO at an $F_iO_2$ of 0.6–0.7. There was no change of mean PAP, SAP, CO or SVR in these lambs.

In eight lambs regression analyses of NO concentration during U46619 infusion vs. SVR, CO or mean SAP showed no significant change. However, all dose levels of NO inhalation produced a prompt reduction of the pulmonary vasoconstriction and pulmonary hypertension caused by U46619 infusion (FIGS. 1, 2). The onset of pulmonary vasodilation occurred within seconds after beginning NO inhalation. The vasodilator effect was nearly maximal within three minutes (FIG. 3). Ceasing to inhale NO caused a return to the prior level of vasoconstriction within three to six minutes. The inhaled NO pulmonary vasodilator response curve of eight lambs is shown in FIG. 1. 5 ppm NO (an inhaled lung dose of 0.89 µg/kg/min) significantly reduced the PA pressure, and an almost complete vasodilator response occurred by inhaling 40 or 80 ppm. After considering the minor reduction over time of baseline PAP during U46619 infusion, comparison of the vasodilator response of the second exposure to breathing 5, 10 and 20 ppm NO demonstrated no significant reduction from the prior series of exposures (FIG. 2). An additional study of four lambs inhaling 80 ppm NO for one hour during U46619 infusion demonstrated pulmonary vasodilation to a normal PAP, with pulmonary hypertension recurring after NO inhalation.

All five lambs in which acute hypoxic pulmonary hypertension had been induced demonstrated a marked increase of cardiac output. In each instance when 40 or 80 ppm of NO was added to the inspired hypoxic gas mixture, pulmonary artery pressure returned to control levels despite the maintenance of elevated cardiac output; mean PVR dropped 33% (Table 1). The $P_aO_2$ and $P_vO_2$ during hypoxia with and without NO were similar.

TABLE 1

ALTERATIONS OF HEMODYNAMICS AND GAS EXCHANGE

Figure 5A:
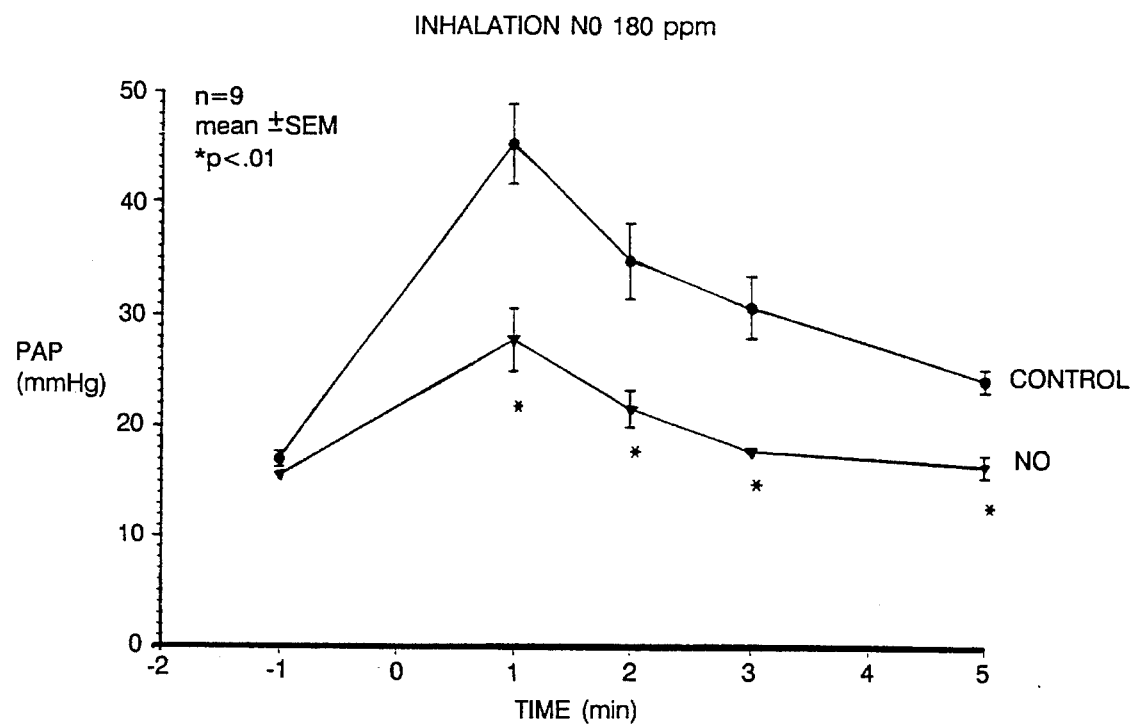
FIGS. 5a and 5b is a pair of graphs comparing the effect of 180 ppm inhaled NO with untreated controls breathing air on the PAP and PVR of sheep in which a heparin-protamine reaction has induced an elevated PAP and PVR.
Figure 5B:
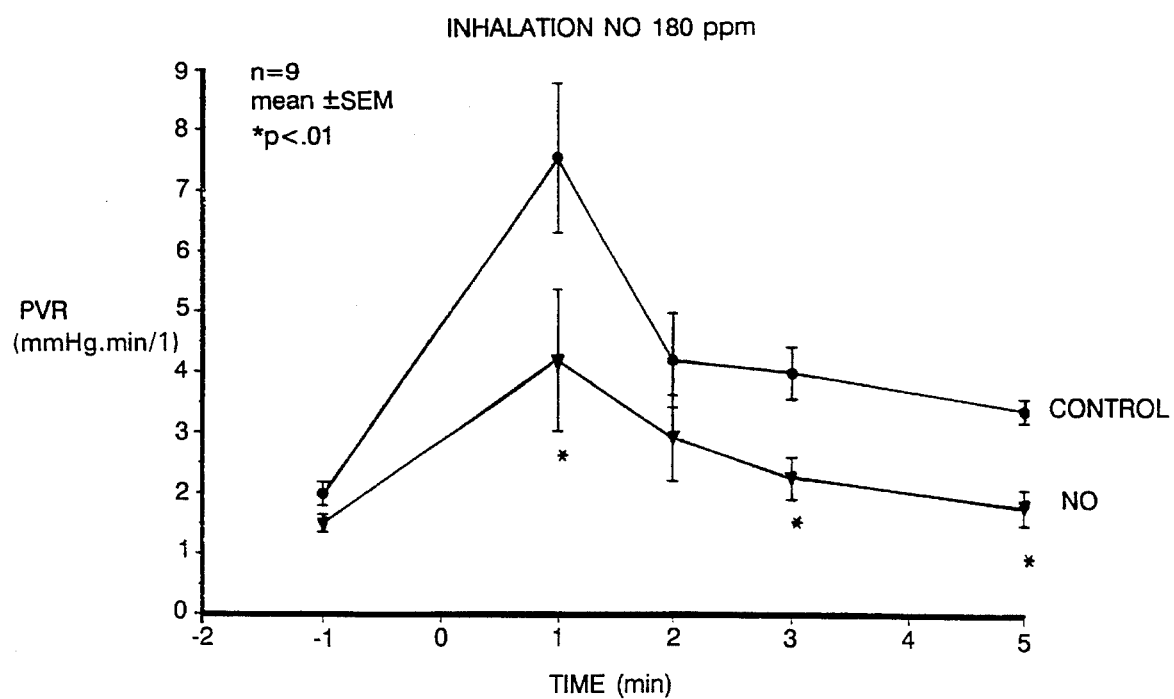

|  | CONTROL | HYPOXIA | HYPOXIA + 40–80 PPM NO |
|---|---|---|---|
| $F_iO_2$ | 0.21 | 0.06 – 0.08 | 0.06 – 0.08 |
| $P_aO_2$ (mm Hg) | 70.8 ± 4.4 | 28.2 ± 1.4* | 31.1 ± 1.7* |
| $P_vO_2$ (mm Hg) | 36.8 ± 2.5 | 16.6 ± 1.8* | 19.8 ± 3.2 |
| $P_aCO_2$ (mm Hg) | 33.9 ± 1.4 | 38.6 ± 2.6 | 40.0 ± 2.7 |
| pHa | 7.47 ± 0.01 | 7.42 ± 0.03 | 7.40 ± 0.03 |
| PAP (mm Hg) | 16.7 ± 0.6 | 28.3 ± 2.2* | 18.7 ± 1.1# |
| LAP (mm Hg) | 5.2 ± 0.8 | 6.4 ± 0.5 | 4.2 ± 1.0 |
| CO (l/min) | 4.55 ± 0.13 | 7.08 ± 0.22* | 7.56 ± 0.79* |
| PVR (mm Hg/l/min) | 2.51 ± 0.11 | 3.07 ± 0.25 | 2.01 ± 0.35# |
| SAP (mm Hg) | 103 ± 6 | 113 ± 7 | 106 ± 5# |
| CVP (mm Hg) | 3.0 ± 1.3 | 3.5 ± 0.8 | 2.8 ± 1.6 |
| SVR (mm Hg/l/min) | 21.7 ± 1.4 | 16.2 ± 0.9* | 13.7 ± 1.0* | n = 5, mean ± S.E.
*p < .01 value differs from control
p < .01 NO + hypoxia value differs from hypoxia iii. Further Experiments FIG. 5 illustrates the ability of 180 ppm inhaled NO to prevent the elevated PAP and PVR caused by the heparin-protamine reaction in nine awake sheep as compared to control air-breathing sheep. The heparin-protamine reaction was induced in these nine sheep by first administering heparin (200 U/kg; Elkins-Sinn, Cherry Hill, N.J.) followed five minutes later (at time zero) by protamine (2 mg/kg; Elkins-Sinn). Each of these sheep also served as a control. Six additional sheep were given an intravenous infusion of sodium nitroprusside (40 µg/kg/min body weight; Elkins-Sinn) while breathing air (data not shown). The 180 ppm NO inhaled dose proved capable of lowering the heparin-protamine-induced PAP in this sheep model to a degree comparable to 40 μg/kg/min SNP infusion, and without the latter drug's propensity to cause marked systemic hypotension.

Lungs from three lambs which had breathed 80 ppm NO for 180 min were studied by light microscopy for evidence of morphological changes caused by breathing NO. No significant differences between these lungs and control lungs were observed.

B. Protocol for Administration of Gaseous NO to Infants with Persistent Pulmonary Hypertension of the Newborn The following is a description of an approved experimental protocol for the administration of NO to newborns at Massachusetts General Hospital. Selection of participants:

Ten patients with persistent pulmonary hypertension of the newborn (PPHN) will be enrolled in the study.

a. Inclusion criteria
  infants under 1 week of age
  infants with arterial blood sampling sites in the pre- and post-ductal distribution
  infants requiring mechanical ventilatory support
  respiratory failure as defined by criteria of Short, Clin. Perinatol. 14:737–748, 1987
  infants may be receiving infusions of systemic vasodilators and/or buffers (bicarbonate)

b. Exclusion criteria
  prematurity as defined by a gestational age <37 weeks by examination, maternal-fetal ultrasound and dates
  birth weight <2500 g
  pulmonary hypoplasia as suggested by a history of oligohydramnios, congenital diaphragmatic hernia, congenital scoliosis, or features consistent with asphyxiating thoracic dystrophy
  unevacuated pneumothorax despite chest tube
  pneumopericardium or pneumomediastinum with hypotension
  fixed anatomic cardiac and vascular lesions (excluding isolated patent ductus arteriosus and patent foramen ovale)
  active pulmonary hemorrhage or platelet count <50,000/mm$^3$
  cranial ultrasound within 24 hours of study entry providing evidence of intracranial hemorrhage
  hyperviscosity as defined by a venous hematocrit ≧70% within 24 hours of birth
  sepsis, as defined by positive blood cultures for pathogenic organisms
  those who do not have informed consent from a parent or legal guardian Study Procedure:

Selected patients will be maintained in a supine position and will receive 3 μg/kg fentanyl for sedation, and 0.1 mg/kg pancuronium bromide for muscle relaxation (unless so treated within the previous hour). The infant will be transported to the catheterization suite accompanied by an attending pediatric anesthesiologist, where a flow directed pulmonary artery catheter will be placed percutaneously via a femoral vein under local anesthesia. The catheter will directly measure pulmonary artery pressure in order to accurately assess the degree of pulmonary hypertension and vasodilatory response to NO inhalation. Upon return to the Neonatal ICU, the $F_iO_2$ will be adjusted to 0.90. The patient will be allowed to equilibrate during this control phase for 20 minutes after all necessary nursing and medical interventions have ceased. If improvement, as defined below, has not occurred, an arterial blood sample will be obtained from a post-ductal site. NO in nitrogen will then be introduced into the breathing circuit by continuous flow. A one way valve will prevent back flow of oxygen into the NO tank. The same $F_iO_2$ (0.90) and flow rate will be maintained. The initial concentration of inspired NO will be 20 ppm. Improvement will be defined as a $P_aO_2$>100 mm Hg and a A-aDO$_2$ of <570 mm Hg (post-ductal sample). If no change is noted the concentration of inhaled NO will be increased to 40 ppm at a constant $F_iO_2$ and flow rate. A post-ductal arterial blood gas will again be measured. If the same criteria are again not met, the NO concentration will be increased to 80 ppm and a third arterial blood gas sampled. The breathing period for each concentration of NO will last 10 minutes.

Following termination of the treatment period, blood will again be obtained for arterial blood gas analysis. Samples will also be taken before and after NO exposure for analysis of methemoglobin and hemoglobin levels and reticulocyte count. A blood smear will be examined for evidence of Heinz bodies. These will be repeated 24 hours after treatment to assess any changes associated with NO breathing. The total volume of blood sampled will be less than 5 ml.

Statistical Methodology:

Data will be assessed with an analysis of variance with repeated measures of unequal group sizes. Winer, "Single factor experiments having repeated measures on the same elements", in *Statistical Principles in Experimental Design.*, 2d Ed., New York, McGraw-Hill, (1971), pp. 261–308. Post hoc testing will be with a Mann-Whitney U. Significance will be judged at the 5% level.

C. Results of Administering NO to Infants with Persistent Pulmonary Hypertension of the Newborn (PPHN)

First subject.

Through compassionate use, nitric oxide was administered to an infant suffering from persistent pulmonary hypertension and congenital heart disease. As a result of prolonged ventilation, absence of a preductal arterial blood sampling site, and the existence of the atrial-ventricular (AV) canal, the patient was not included in the PPHN study mentioned above.

The patient was a 3225 gm, full term male who had been treated with extracorporeal membrane oxygenation (ECMO) because of the severity of his congenital heart disease and profound hypoxemia. He had been taken off ECMO and was being maintained intubated and ventilated in the newborn intensive care unit. He subsequently became progressively hypoxemic, as reflected in his post-ductal pulse oximetry (POX) values. By the time he was taken to the catheterization laboratory to confirm the existence of the A-V canal and to determine if some emergent cardiac surgery was needed, he was receiving maximal medical and ventilatory life support and remained dangerously hypoxemic. Under these circumstances, we were granted consent to treat the patient with nitric oxide.

Upon arrival to the catheterization laboratory, the patient was extremely cyanotic. He was treated with fentanyl, oxygen, hyperventilation and intravenous fluid boluses to stabilize him prior to administering NO. As shown in Table 2, the catheterization revealed severe pulmonary hypertension and an A-V canal. The shunting did not appear to correct with treatment with oxygen or hyperventilation.

TABLE 2

HEMODYNAMICS AND BLOOD GAS VALUES FOR NO INHALATION TREATMENT OF INFANT WITH PPHN

|  | ARRIVAL | $F_iO_2$ 1.0 | $F_iO_2$ 0.9 | NO 20 ppm | NO 40 ppm | NO 80 ppm | OFF #1 | NO 80 ppm | OFF #2 |
|---|---|---|---|---|---|---|---|---|---|
| $O_2$ SAT (%) | | | | | | | | | |
| RA | 23 | 61 | 67 | 67 | 72 | 74 | 14 | — | — |
| PA | 28 | 69 | 72 | 70 | 74 | 75 | 17 | — | — |
| POSTDUCTAL | | | | | | | | | |
| ART | 63 | 74 | 84 | 85 | 74 | 88 | 28 | 85 | 19 |
| POX | — | 89 | 91 | 91 | 93 | 94 | 21 | 90 | 24 |
| POSTDUCTAL ARTERIAL $PO_2$ (mmHg): ART | 30 | 43 | 48 | 46 | 50 | 51 | 21 | 48 | 16 |
| MEAN PRESSURE (mmHg) | | | | | | | | | |
| RA | 6 | 4 | 4 | 5 | 4 | 5 | — | — | — |
| PA | 57 | 52 | 47 | 50 | 52 | 53 | — | — | — |
| ART | 52 | 50 | 45 | 45 | 43 | 47 | — | — | — |

POX = pulse oximeter

We utilized a regulator to step-down the pressure of the NO into a blender, which allowed us to adjust the relative amounts of the 800 ppm $NO/N_2$ and 100% $N_2$ supplies. Treating the patient with pure oxygen, we increased the flow of $N_2$ through a flow regulator into the inspiratory circuit of the breathing circuit of the breathing cicuit until the $F_iO_2$ was 0.9. The effects are shown in Table 2. This provided a 1:10 dilution of the nitrogen gas. We then used the blender to adjust the relative amounts of $N_2$ and $NO/NO_2$ to provide 0 to 80 ppm of NO.

The data in Table 2 demonstrate that exposure to NO had no adverse effect on systemic blood pressure ("Mean Pressure-Art"), while inducing a modest increase in arterial saturation, pulse oximetry values, and arterial partial pressure of oxygen. This may reflect a stabilizing effect of the gas during this period. After the nitric oxide was discontinued and the central catheters were removed, the arterial saturation and oxygen gas tension precipitously dropped. The RA and PA values could not be determined, as the catheters had been removed. As other attempts to resuscitate the patient were failing, the nitric oxide was restarted in an attempt to improve the baby's condition. It succeeded in improving the oxygen saturation and blood gas tension. In a subsequent attempt to wean the patient off nitric oxide, again the patient's oxygenation level deteriorated to dangerously low levels. The patient was maintained on nitric oxide and returned to the newborn intensive care unit.

While in the intensive care unit, prostaglandin E1 was infused into the patient in an attempt to dilate the pulmonary vasculature. Despite a standard dosage of prostaglandin, nitric oxide could not be discontinued without the return of dangerously low oxygen saturations. The patient remained on nitric oxide until he could be placed on ECMO. This trial demonstrated the utility of nitric oxide in improving gas exchange in this patient with pulmonary hypertension and congenital heart disease.

Subsequent subjects.

Two more infants with PPHN have been treated by NO inhalation. Both had an excellent response to breathing NO at 20–80 ppm, showing increases in preductal oxygenation, and both survived longterm. One of the infants showed such rapid improvement with NO inhalation alone that ECMO was altogether avoided.

D. Results of Administering NO to Adults with Adult Respiratory Distress Syndrome First subject.

The patient, a 42-year old woman, had suffered for three weeks from adult respiratory distress syndrome (ARDS) due to aspiration pneumonia. There was diffuse pulmonary edema and a large $Q_{VA}/Q_T$ (30%). After 21 days of veno-venous extracorporeal membrane oxygenator support (3 liters/min blood flow), the mean PAP was 55 mm Hg.

The short term effects of inhaled nitric oxide were compared with those of i.v. prostacyclin ($PGI_2$; 5 ng/kg/min). Mean pulmonary arterial pressure (PAP), right ventricular ejection fraction (RVEF) and gas exchange variables were evaluated. RVEF was assessed by thermodilution, and gas exchange alterations were analyzed using the multiple inert gas elimination technique (MIGET). MIGET and RVEF data were obtained on two different occasions. Ventilator settings were tidal volume 6 ml/kg, respiratory rate 14/min, $F_iO_2$ 0.4–0.48 and 5 cm $H_2O$ of PEEP (positive end expiratory pressure).

TABLE 3

HEMODYNAMIC RESULTS OF TREATMENT OF ADULT WITH PULMONARY HYPERTENSION

|  | PG12 | Control | NO 18 ppm | NO 36 ppm | Control |
|---|---|---|---|---|---|
| #1 | | | | | |
| PAP (mm Hg) | 46 | 54 | 42 | 37 | 49 |
| PCWP (mm Hg) | 12 | 15 | 15 | 15 | 14 |
| MAP (mm Hg) | 81 | 86 | 78 | 75 | 80 |
| $PaO_2$ (torr) | 74 | 104 | 146 | 127 | 100 |
| $Q_A/Q_r$ % | 57 | 38 | 26 | 33 | 30 |
| low $V_D/Q$ % | 0 | 2 | 1 | 0 | 0 |
| $V_D/V_T$ % | 51 | 47 | 43 | 40 | 41 |
| #2 | | | | | |
| PAP (mm Hg) | 42 | 52 | 38 | 36 | 50 |
| PCWP (mm Ng) | 14 | 14 | 14 | 12 | 14 |
| MAP (mm Hg) | 86 | 91 | 88 | 86 | 88 |
| $PaO_2$ (torr) | 81 | 84 | 127 | 113 | 90 |

TABLE 3-continued

HEMODYNAMIC RESULTS OF TREATMENT OF
ADULT WITH PULMONARY HYPERTENSION

|  | PG12 | Control | NO 18 ppm | NO 36 ppm | Control |
|---|---|---|---|---|---|
| RVEF % | 42 | 27 | 36 | 39 | 28 |

Figure 6:
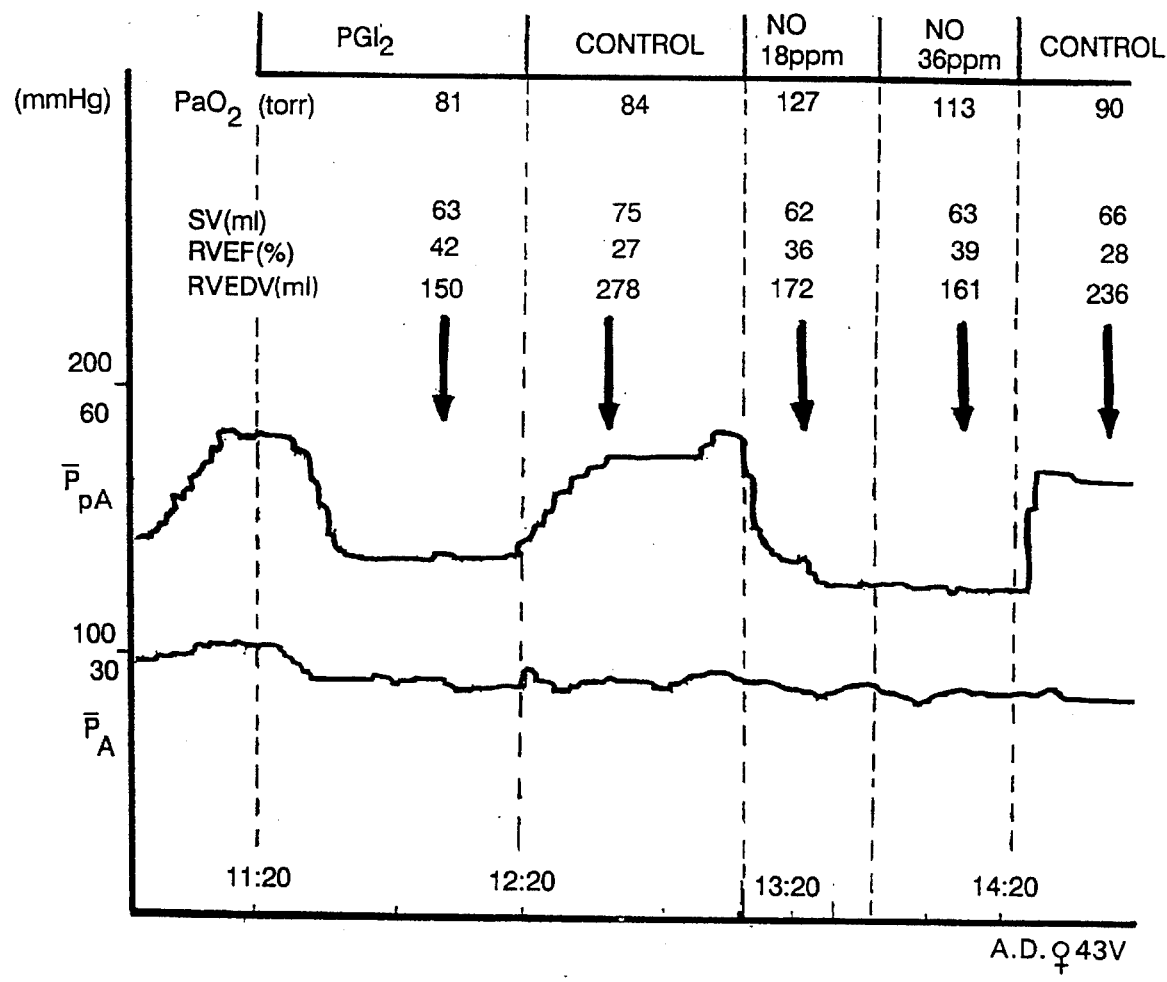
FIG. 6 is a strip chart recording comparing treatment with $PGI_2$ and with NO inhalation in an adult human with severe ARDS.

As illustrated in FIG. 6 and in Table 3, inhaled NO lowered PAP and improved RVEF as did i.v. $PGI_2$, but, in contrast to $PGI_2$, NO increased $PaO_2$ and decreased right-to-left shunt and $V_D/V_T$. Inhalation of 18 ppm NO in oxygen caused a reduction of mean PAP to 38–42 mm Hg (a decrease of 12–14 mm Hg) and reduced the PVR by 44%, the wedge pressure remaining constant near 15 mm Hg and the cardiac output near 7 liters/min and unchanged. There was a small additional vasodilation (2–5 mm Hg) caused by increasing the NO concentration to 36 ppm. Vasodilation with NO was sustained for about 1½ hours, when administration was electively ceased. During NO inhalation, the $Q_{VA}/Q_T$, measured with sulphur hexafluoride, decreased from 38% to 26% (18 ppm NO) and 33% (36 ppm NO). There was no change of systemic arterial pressure with inhaled NO: unlike the systemic vasodilator $PGI_2$, which increased $Q_{VA}/Q_T$ to 57%, inhaled NO predominantly vasodilates the vasculature of ventilated lung regions. This trial is a clear demonstration of the selective ability of low levels (18–36 ppm) of inhaled NO to act as a potent pulmonary vasodilator in a patient with severe acute lung injury (ARDS), without increasing the shunt.

Subsequent subjects.

Nine additional patients have been treated for ARDS by NO inhalation, for periods up to 28 days. Seven survived in spite of their severe respiratory distress symptoms, displaying marked reductions of $Q_{VA}/Q_T$ during NO breathing, as well as a reduced PAP. No important increase of methemoglobin levels was observed. These results indicated that NO inhalation for up to several weeks is a promising therapy for acute respiratory failure.

E. Results of Administering NO to Humans with
Normal (Non-Constricted) and Hypoxic
(Constricted) Lungs The effects of breathing 40 ppm NO were studied in five awake, healthy human volunteer subjects inhaling various gas mixtures for 10 min periods, with measurements starting at 6 min. Table 4 shows that in subjects breathing air with a normal (21% v/v) $O_2$ concentration, and whose lungs therefore were not vasoconstricted, NO has no pulmonary or systemic vasodilatory effect.

TABLE 4

EFFECTS OF 40 PPM NO ON THE
NON-CONSTRICTED HUMAN LUNG

|  | Air (21% $O_2$) | Air (21% $O_2$) + 40 ppm NO | Air (21% $O_2$) |
|---|---|---|---|
| PAP mmHg | 13.7 ± 1.7 | 14.0 ± 1.8 | 15.4 ± 2.8 |
| PCWP mmHg | 9.1 ± 1.7 | 10.1 ± 2.5 | 9.9 ± 2.2 |
| CO l/min | 6.40 ± 0.92 | 6.40 ± 0.88 | 6.95 ± 1.18 |
| PVR mmHg · min/l | 0.72 | 0.61 | 0.79 |
| MAP mmHg | 87.4 ± 6.0 | 88.0 ± 3.7 | 90.2 ± 5.4 |
| CVP mmHG | 5.7 ± 1.4 | 6.3 ± 1.7 | 6.1 ± 1.6 |
| $PaO_2$ mmHg | 99.6 ± 7.5 | 94.7 ± 16.3 | 95.3 ± 14.5 |
| $PaCO_2$ mmHg | 38 ± 6 | 38 ± 5 | 39 ± 4 |
| $SaO_2$ % | 97.6 ± 0.4 | 96.0 ± 1.0 | 97.1 ± 1.2 |

Values given as X ± S.D. n = 5

In contrast, the same subjects breathing a relatively low level of oxygen (12% v/v) exhibited hypoxia-induced pulmonary vasoconstriction with elevated PAP and PVR, an effect that could be reversed completely by adding 40 ppm NO to the inhaled gas mixture (Table 5).

TABLE 5

EFFECTS OF 40 PPM NO ON THE HYPOXIC,
VASCONSTRICTED HUMAN LUNG

|  | Air (21% $O_2$) | 12% $O_2$ | 12% $O_2$ + 40 ppm NO | 12% $O_2$ | Air (21% $O_2$) |
|---|---|---|---|---|---|
| PAP mmHg | 14.3 ± 2.3 | 19.1 ± 2.6# | 13.7 ± 1.7* | 15.7 ± 2.2 | 14.5 ± 1.5 |
| PCWP mmHg | 8.8 ± 1.9 | 8.5 ± 1.3 | 8.5 ± 2.2 | 9.2 ± 1.6 | 9.7 ± 1.9 |
| CO l/min | 6.65 ± 0.95 | 8.66 ± 1.87 | 8.37 ± 1.68 | 8.5 ± 1.9 | 7.06 ± 1.84 |
| PVR mmHg · min/l | 0.83 | 1.22 | 0.62 | 0.76 | 0.68 |
| MAP mmHg | 88.8 ± 6.9 | 89.4 ± 8.4 | 86.0 ± 5.7 | 84.4 ± 7.6 | 88.4 ± 6.3 |
| CVP mmHg | 5.9 ± 3.0 | 5.6 ± 2.2 | 5.2 ± 2.6 | 5.0 ± 1.9 | 6.2 ± 1.6 |
| $PaO_2$ mmHg | 99 ± 14 | 47 ± 5 | 45 ± 5 | 45 ± 8 | 93 ± 16 |
| $PaCO_2$ mmHg | 40 ± 4 | 35 ± 3 | 34 ± 5 | 33 ± 6 | 39 ± 6 |
| $SaO_2$ % | 97.5 ± 1.0 | 85.4 ± 3.4 | 83.9 ± 5.7 | 82.6 ± 11 | 96.8 ± 1.3 | n = 5, X ± S.D.
p < 0.01 value differs from value in first column
*p < 0.01 value differs from the previous situation

2. AIRWAY SMOOTH MUSCLE DILATION

A. Methods

Animal preparation

Male Hartley strain guinea pigs (300–440 g body wt) were anesthetized with α-chloralose (50 mg/kg) and urethane (500 mg/kg) (Drazen et al., J. Appl. Physiol.

48:613–618, 1980). A tracheostomy was performed, and the animals were intubated with a tubing adaptor (ID 1.65 mm) and ventilated with a small animal ventilator (Harvard Apparatus, a division of Ealing Scientific, Natick, Mass.) at 8 ml/kg and 60 breaths/min. A jugular vein was cannulated for intravenous administration of drugs. The chest was opened by bilateral excision of a portion of the ribs anteriorly so that the lungs were exposed to atmospheric pressure (Shore and Drazen, J. Appl. Physiol. 67:2504–2511, 1989). A positive end expiratory pressure of 3–4 $cmH_2O$ was provided.

Material

Guinea pigs were then placed inside a plethysmograph (Amdur and Mead, Am. J. Physiol. 192:363–368, 1958), that was connected to a large reservoir containing copper mesh to maintain the plethysmograph isothermal. Plethysmograph pressure was measured with a differential pressure transducer (Celesco, Canoga Park, Calif.); the opposite side of this transducer was connected to a similar reservoir. Pressure at the airway opening was measured from a side tap in the tracheal canula. Transpulmonary pressure was measured with a differential pressure transducer (Celesco) as the difference between airway opening pressure and the pressure inside the plethysmograph. Flow was obtained by electrical differentiation of the volume (plethysmograph pressure) signal. Tidal volume was measured by recording the pressure changes in the body plethysmograph. Volume, flow, and transpulmonary pressure signals were recorded on a strip chart (General Scanning, Watertown, Mass.). Pulmonary resistance and dynamic compliance were calculated by a computer program according to the method of von Neergard and Wirz (Z. Klin. Med. 105:35–50, 1927; Z. Klin. Med. 105:52–82, 1927).

Figure 7:
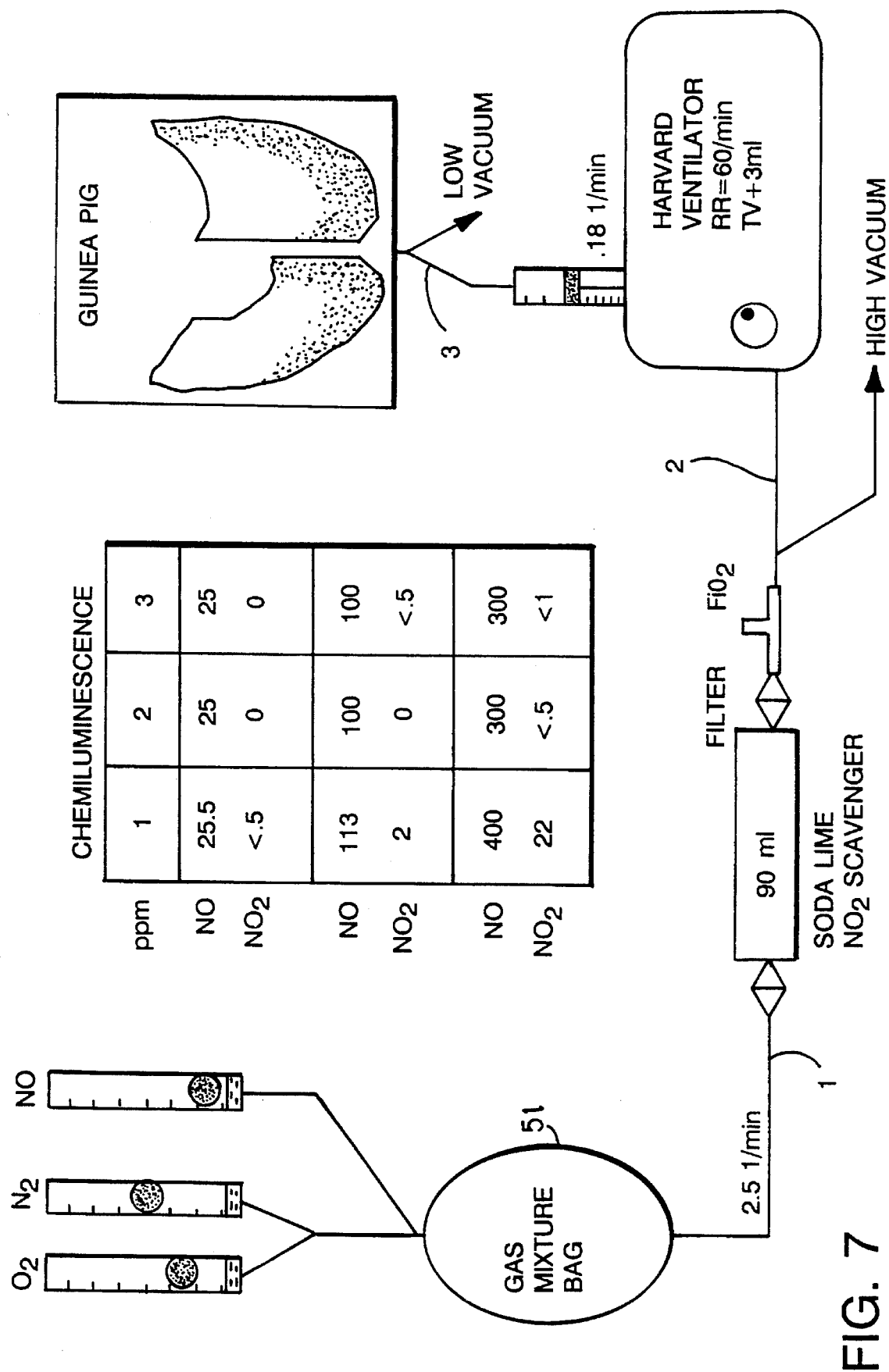
FIG. 7 is a representation of the apparatus and conditions used to deliver NO gas to the lungs of guinea pigs in the course of experiments on bronchodilation, and a summary of the chemiluminescence data collected at each of three sites in the apparatus.

The apparatus and conditions used are diagrammed in FIG. 7. The inspired gas was a precise mixture of nitrogen and oxygen blended via a Y piece tube and immediately diluted with nitric oxide (NO) to produce the correct inspired concentration in a 5 liter gas mixture bag. With volumetrically calibrated flowmeters, varying quantities of NO mixed with $N_2$ were substituted for pure $N_2$ to obtain the desired NO concentration at an inspired oxygen concentration ($FIO_2$) of 0.30–0.32. The total inflow gas rate was maintained at 2.5 l/min. The gas mixture was then sent via a 3 cm ID tube filled with 90 ml of soda lime to scavenge nitrogen dioxide (Stavert and Lehnert, Inhal. Toxicol. 2:53–67, 1990), then through a filter before the ventilator. Just after the ventilator inflow tube, a vacuum was adjusted to maintain the gas mixture bag nearly empty and continuously drive fresh gas into the ventilator circuit. The expiratory gas from the ventilator was scavenged with a vacuum and set up to maintain a positive end expiratory pressure of 3–4 cm $H_2O$. NO was obtained from Air Products and Chemicals, Inc. (Allentown, Penn) as a mixture of 1,034 ppm NO in pure nitrogen. A chemiluminescence $NO/NO_x$ analysis (Fontijin et al., Anal. Chem. 42:575–579, 1970) was performed before and after the soda lime filled tube, and just before the inspiratory valve of the ventilator (see FIG. 7) to assess the nitrogen dioxide concentration and adjust the flowmeters to provide the different levels of NO concentration.

Protocol

Twenty-four guinea pigs were studied. Three series of studies were completed on three separate groups of animals.

Group A

Nine guinea pigs were included in 3 sets of measurements.

i. NO effects on normal bronchial tone.

Figure 8:
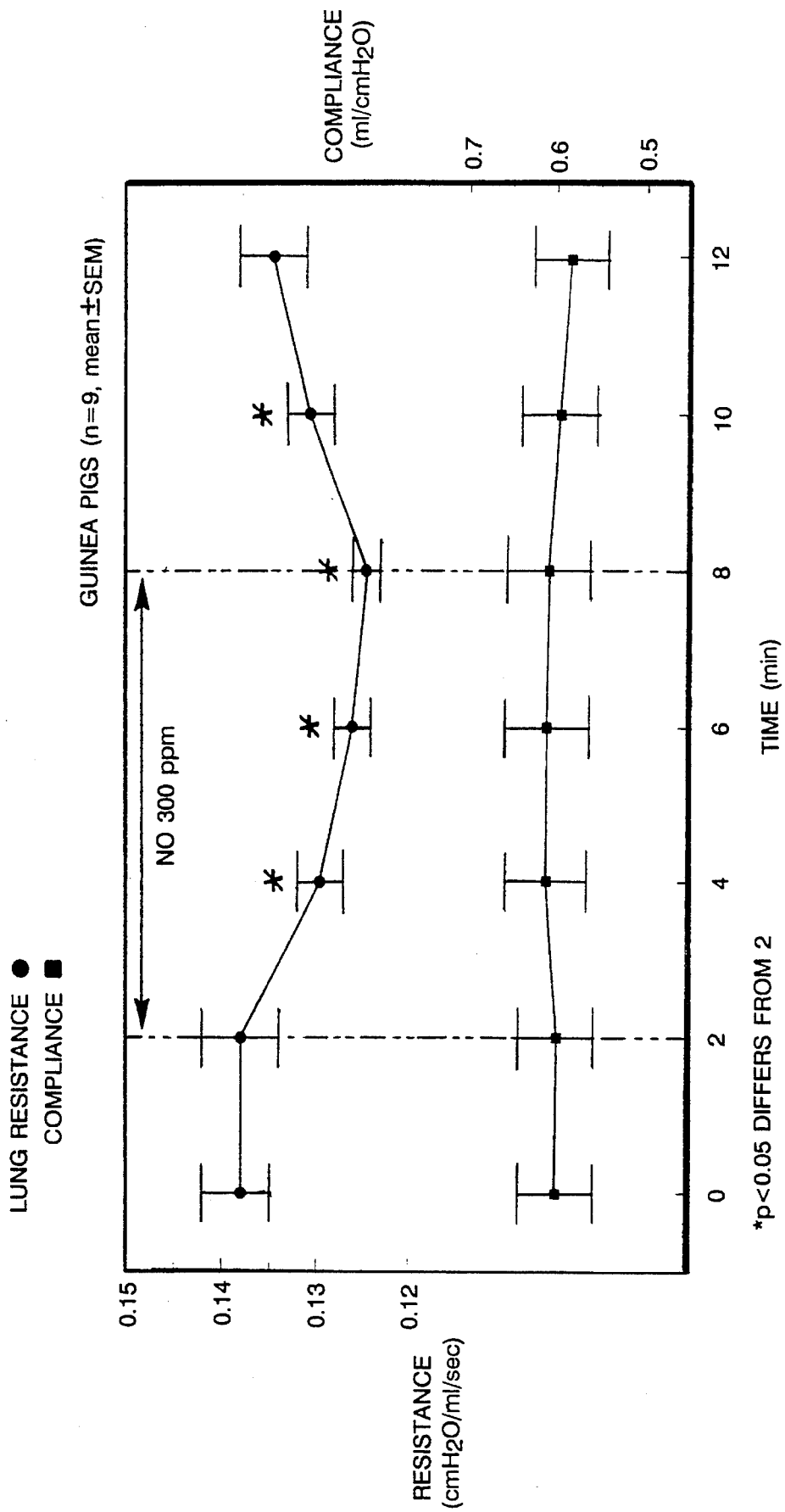
FIG. 8 is a graph illustrating the effects on nine normal (i.e., non-bronchconstricted) guinea pig lungs of inhaling 300 ppm NO gas.
Figure 9:
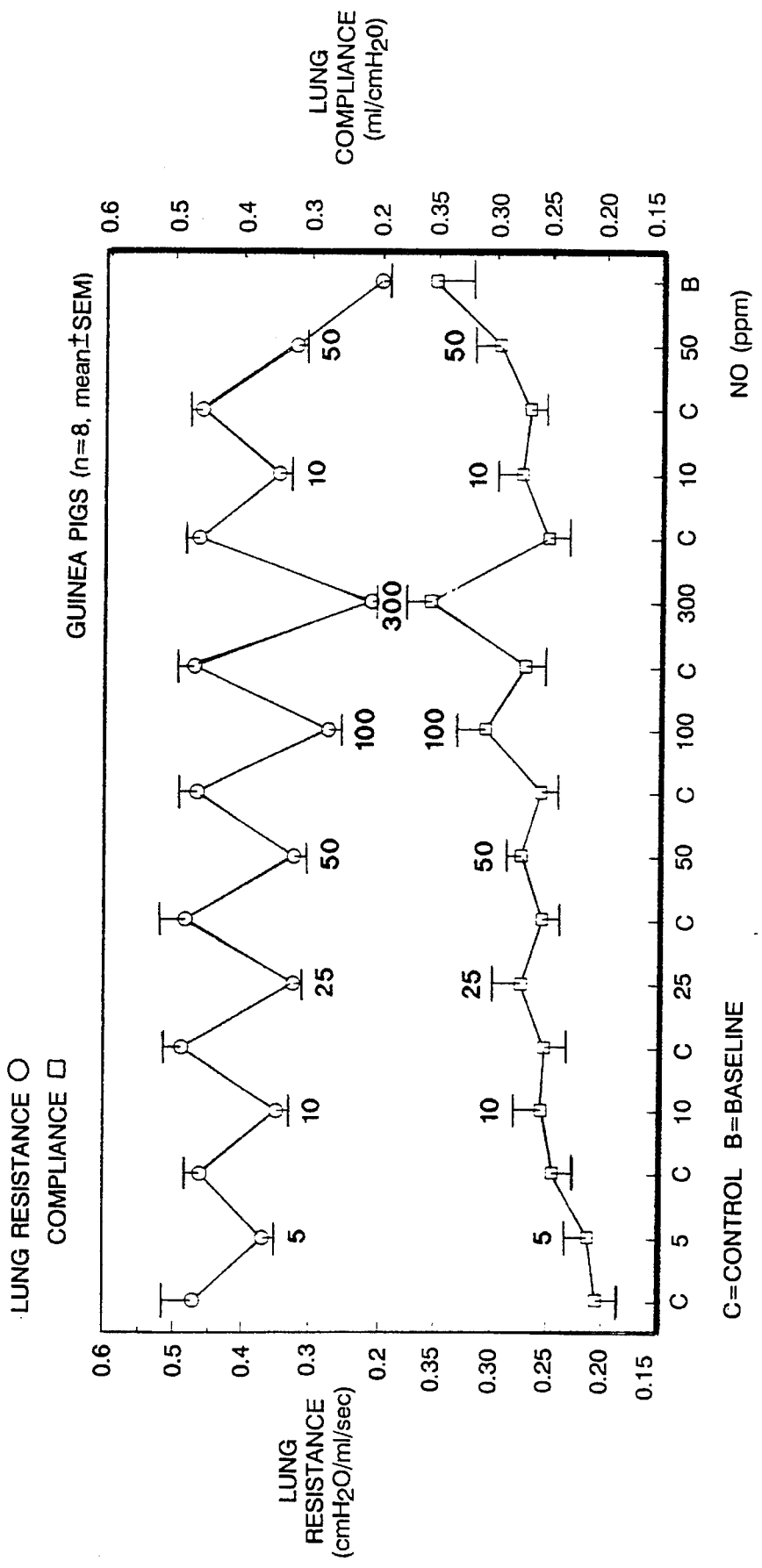
FIG. 9 is a graph illustrating the effects on lung resistance observed in nine experimentally bronchoconstricted guinea pigs during treatment with various concentrations of NO gas.

After baseline measurements of tidal volume, lung resistance and dynamic compliance, the effects on baseline bronchial tone of inhaling 300 ppm NO at $FIO_2$ 0.30–0.32 for 6 to 10 minutes were evaluated (FIG. 8).

ii. Dose-response study of intermittent NO inhalation during methacholine infusion.

After baseline measurements, the same guinea pigs were given an intravenous infusion of a potent bronchoconstrictor, methacholine, at a rate of 2.5–7.5 µg/kg/min in order to reach a medium level of bronchoconstriction (3 to 4 fold the baseline lung resistance). After a stable period, each animal was ventilated with a series of gas mixtures of 5, 10, 25, 50, 100 and 300 ppm NO for 10 minutes at constant $FIO_2$ (0.30–0.32). After each level of NO exposure, lungs were inflated to total capacity to minimize the effects of airway closure. A second exposure to 10 and 50 ppm NO for 10 minutes was performed, and each guinea pig was examined for the occurrence of acute tolerance. After the last level of NO ventilation, methacholine infusion was stopped and measurements done after a stable period of lung mechanics to obtain the reference point for the dose-response study. Only then were the lungs inflated to total lung capacity to reach a stable new baseline value (see FIGS. 9–12).

iii. Study of tolerance to 1 hour of NO inhalation during methacholine infusion.

Figure 13:
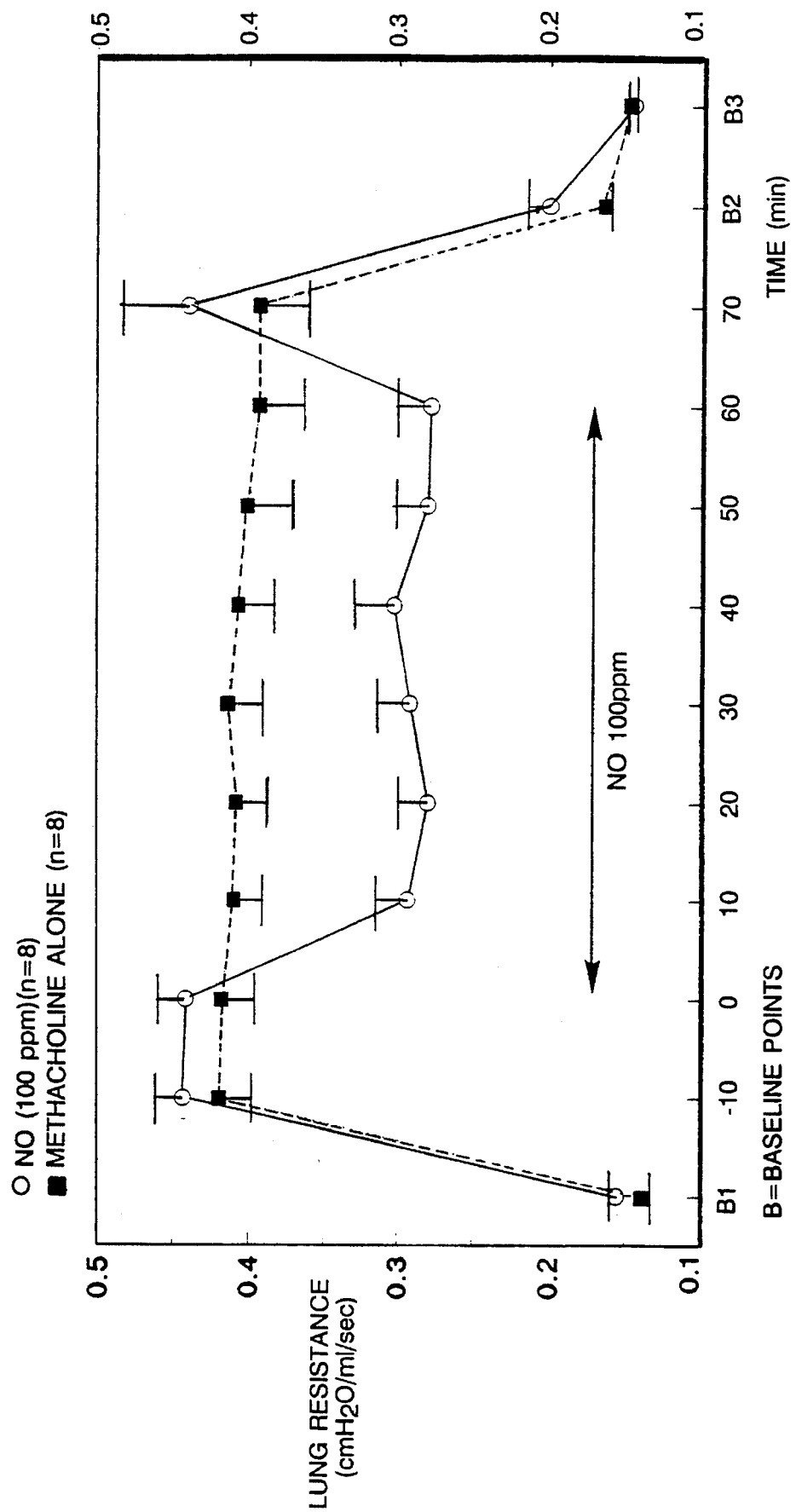
FIG. 13 is a graph illustrating the effects on eight experimentally-bronchoconstricted guinea pig lungs of longterm (one hour) inhalation of 100 ppm NO, or of methacholine alone.

Guinea pigs were given an infusion of methacholine to raise bronchial tone 3 to 4 fold, after which the animals were ventilated with a 100 ppm NO gas mixture for 1 hour at $FIO_2$ 0.30–0.32. Repeated airway measurements were obtained every 5 minutes and then 5 and 10 minutes after ceasing NO inhalation. Methacholine infusion was then discontinued and repeated measurements were obtained after a stable period of lung ventilation, and once again after lung inflation to total lung capacity. Methemoglobin levels were measured (Zwart et al., Clin Chem 27:1903–1907, 1981) at the time of the surgical procedure and again after the tolerance study (FIG. 13).

Group B.

Ten guinea pigs were included in 2 sets of experiments.

i. Study of tolerance of 80 minutes of methacholine infusion alone.

To evaluate the stability of this bronchoconstrictor model, guinea pigs were given an infusion of methacholine at a rate of 2.5–7.5 µg/kg/min to reach the same level of bronchoconstriction as in the 1 hour NO inhalation study (see FIG. 13). Animals were ventilated with an oxygen/nitrogen gas mixture at constant $FIO_2$ (0.30–0.32). Repeated measurements were obtained every 5 minutes. At 10 and 70 minutes, flowmeters were adjusted to simulate NO ventilation. Methacholine infusion was then discontinued. Repeated measurements were obtained after a stable period of lung mechanics, and once again after lung inflation to total lung capacity.

ii. Study of co-regulation of airway smooth muscle tone by cyclic-AMP- and cyclic-GMP-dependent mechanisms.

Figure 14:
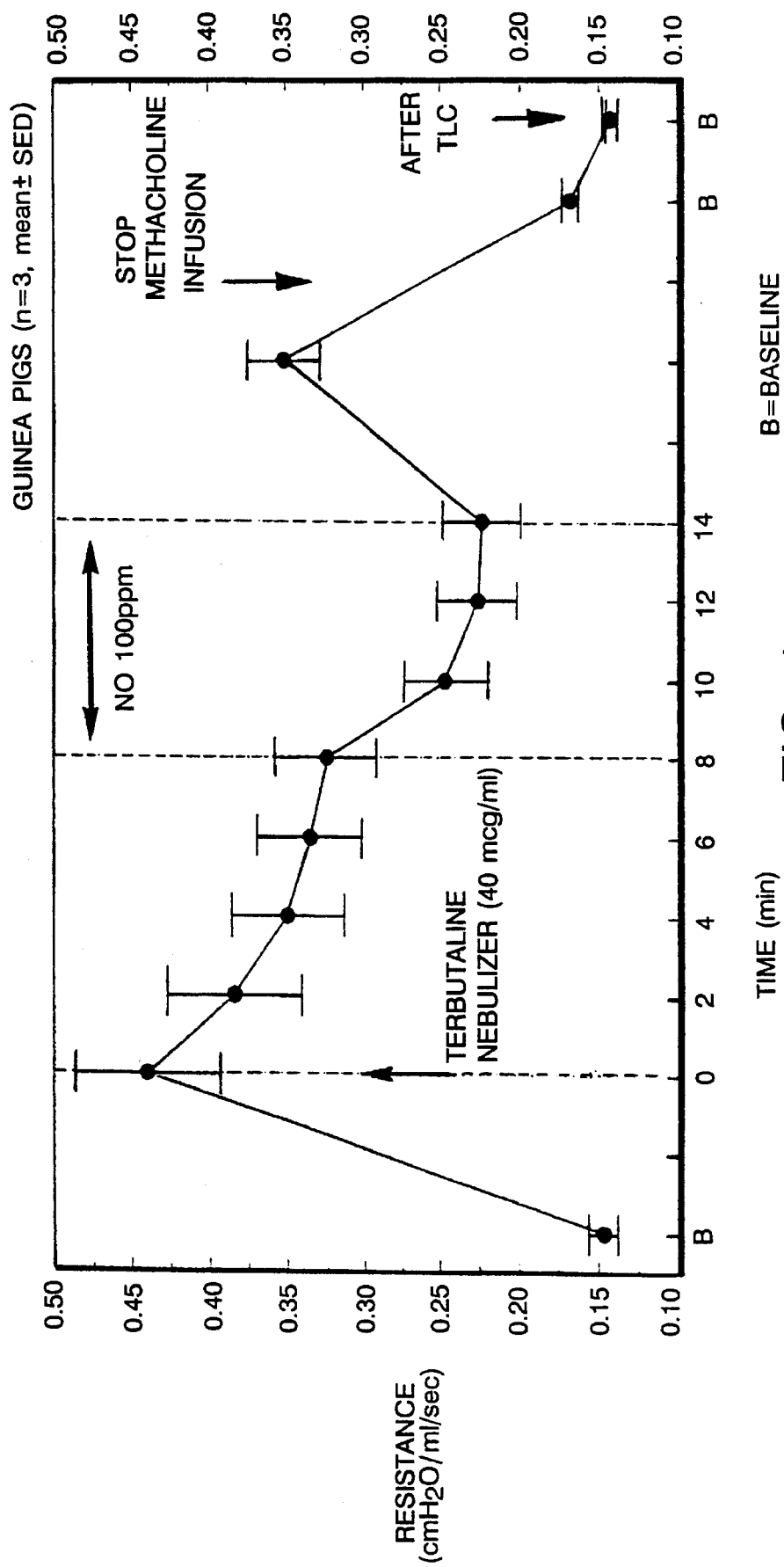
FIG. 14 is a graph illustrating the additive effects of inhaling both terbutaline and NO on lung resistance in three experimentally-bronchoconstricted guinea pigs.
Figure 15:
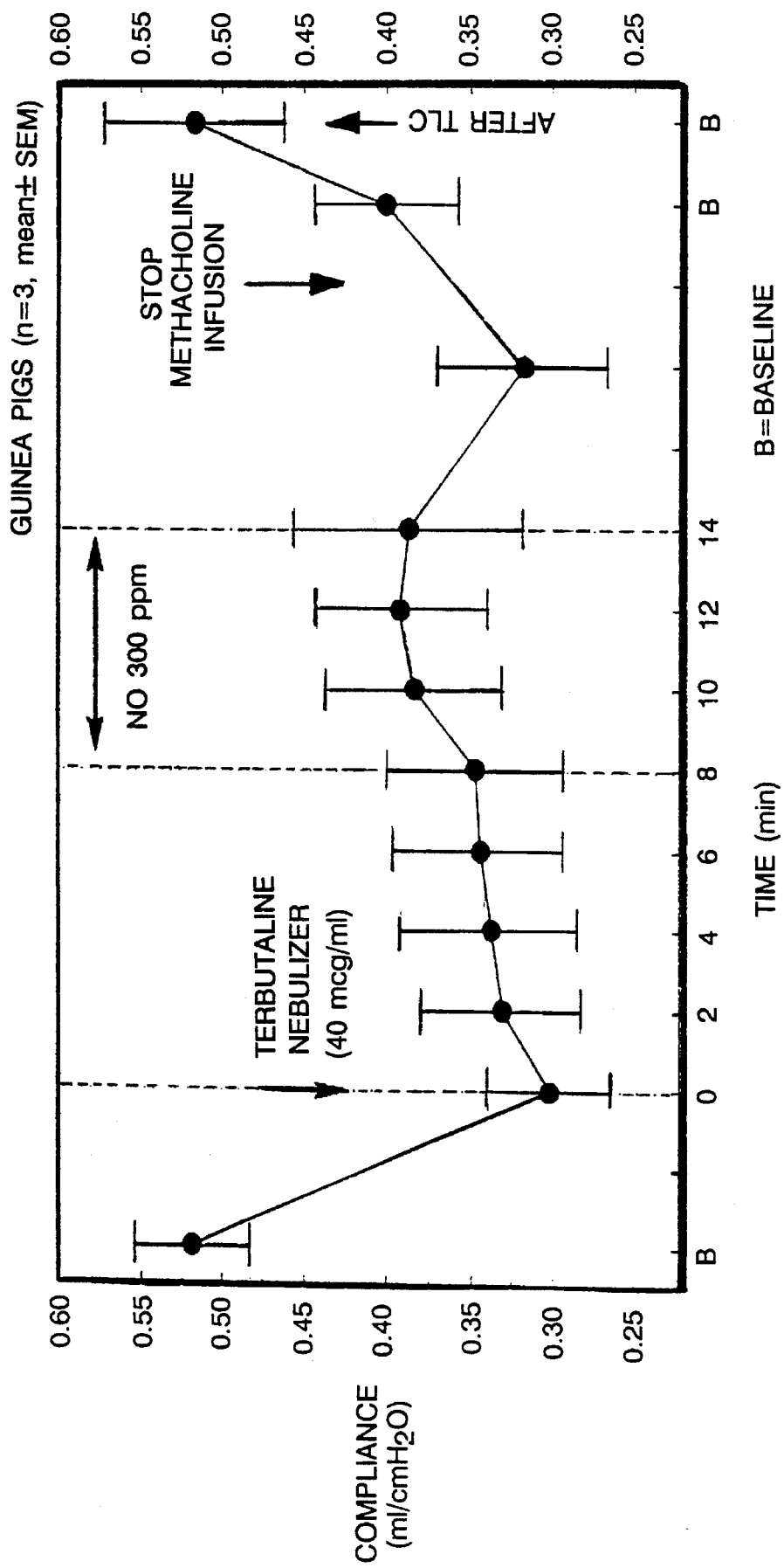
FIG. 15 is a graph illustrating the additive effects of inhaling both terbutaline and NO on lung compliance in three experimentally-bronchoconstricted guinea pigs.

After baseline measurements, 5 guinea pigs were given a methacholine infusion to raise their lung resistance to the medium level of bronchoconstriction. The guinea pigs received first a terbutaline aerosol followed 10 minutes later by a 100 ppm NO inhalation for 6 minutes, while maintaining a constant $FIO_2$ (0.30–0.32). The terbutaline aerosol was given as follows: 4 ml of a 40 µg/ml terbutaline solution was placed in the reservoir of a nebulizer (Respigard II) and driven by 4 l/min air. The nebulizer was connected via a stopcock to the Y piece of the ventilator circuit and to a tube immersed in 3–4 cm water. At the time of the nebulization, the ventilator was disconnected so that the nebulizer circuit was connected to the airway and 20 nebulized breaths of terbutaline at the same tidal volume were given. Then the ventilator was reconnected, and the nebulizer disconnected. At the end of the study, methacholine infusion was discontinued until stable lung mechanics had returned, and then the lungs were inflated to total lung capacity to reach a final baseline value. Repeated respiratory mechanics measurements were obtained and every 2 minutes during the NO and terbutaline periods (FIGS. 14 and 15).

Group C:

Study of S-nitroso-N-acetylpenicillamine (SNAP, during methacholine bronchoconstriction.

SNAP was prepared according to the method described in Field et al., J. Chem. Soc. Chem. Comm. (1978), 249–250, and was stored as crystals at 0° C. for up to 120 days without detectable degradation (as assayed by absorbance at 595 nm).

Figure 16:
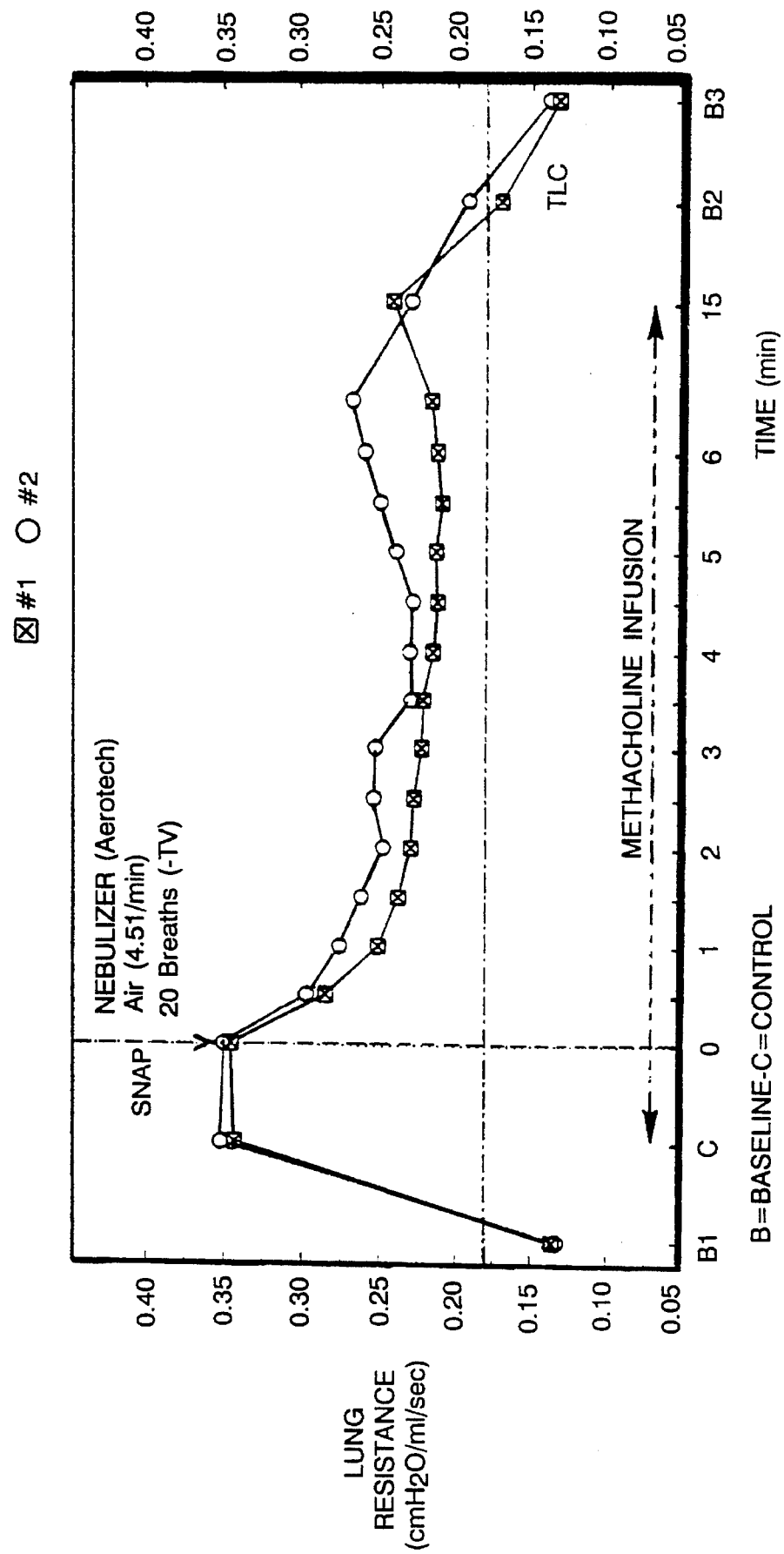
FIG. 16 is a graph illustrating the changes in lung resistance observed in five experimentally-bronchoconstricted guinea pigs inhaling nebulized S-nitroso-N-acetylpenicillamine (SNAP).

After obtaining baseline respiratory measurements, 5 guinea pigs were given a methacholine infusion to raise their lung resistance to a medium level of bronchoconstriction. After two minutes, each guinea pig received a SNAP aerosol. The SNAP aerosol was given as follows: 200 mM of SNAP dissolved in an ethanol/water mixture (4 ml) was placed in the reservoir of a nebulizer (Respigard II) and driven by 4 l/min air. The nebulizer was connected via a stopcock to the Y piece of the ventilator circuit and to a tube immersed in 4 cm water. At the time of nebulization, the ventilator was disconnected so the nebulizer circuit was connected to the airway and 20 nebulized breaths of SNAP at the same tidal volume were given. Then the ventilator was reconnected and the nebulizer disconnected. At the end of the study (15 minutes) the methacholine infusion was discontinued until stable lung mechanics had returned; then the lungs were inflated to total lung capacity to reach a final baseline value. Repeated respiratory mechanics measurements were obtained every two minutes (FIG. 16).

B. Results

Figure 10:
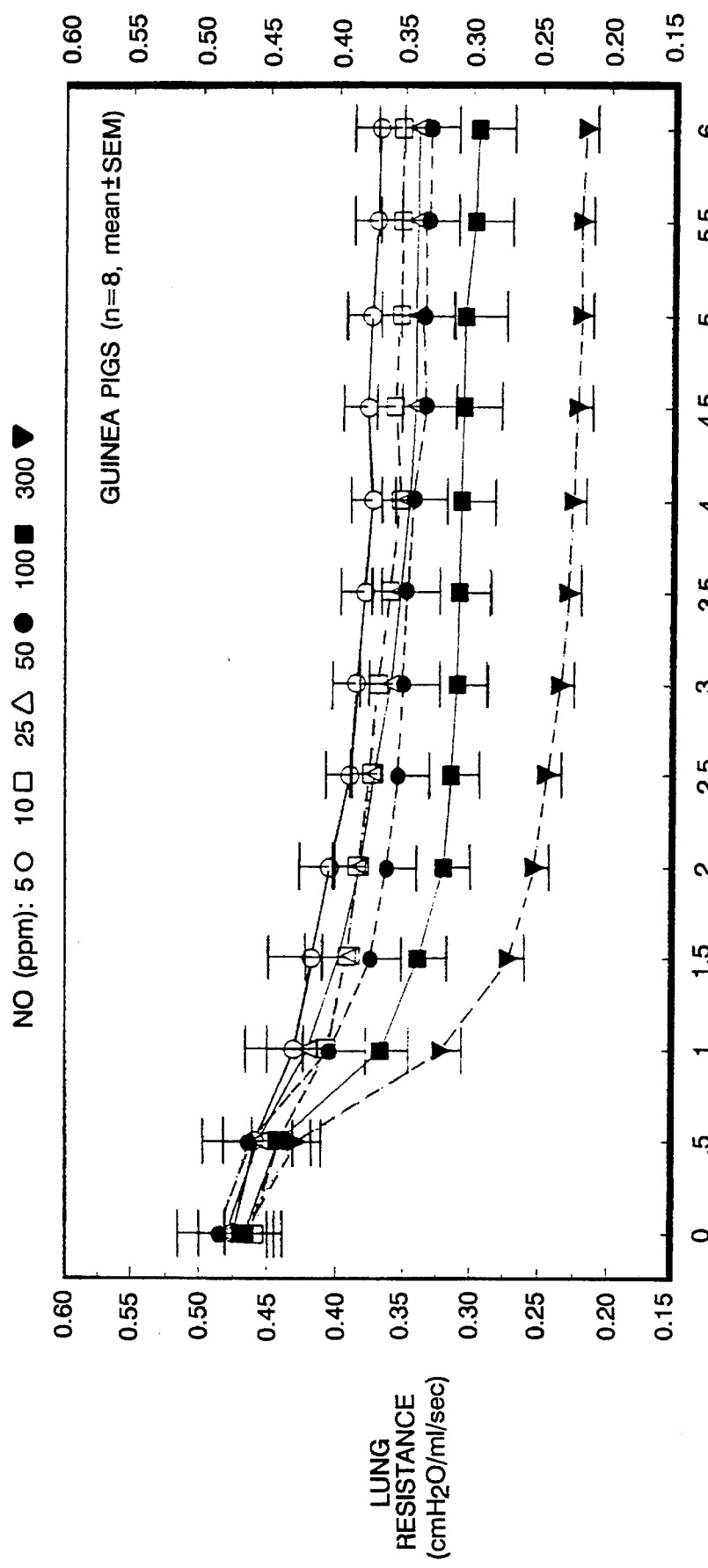
FIG. 10 is a graph comparing lung resistance upon treatment of eight experimentally bronchoconstricted guinea pigs with various concentrations of NO gas.
Figure 11:
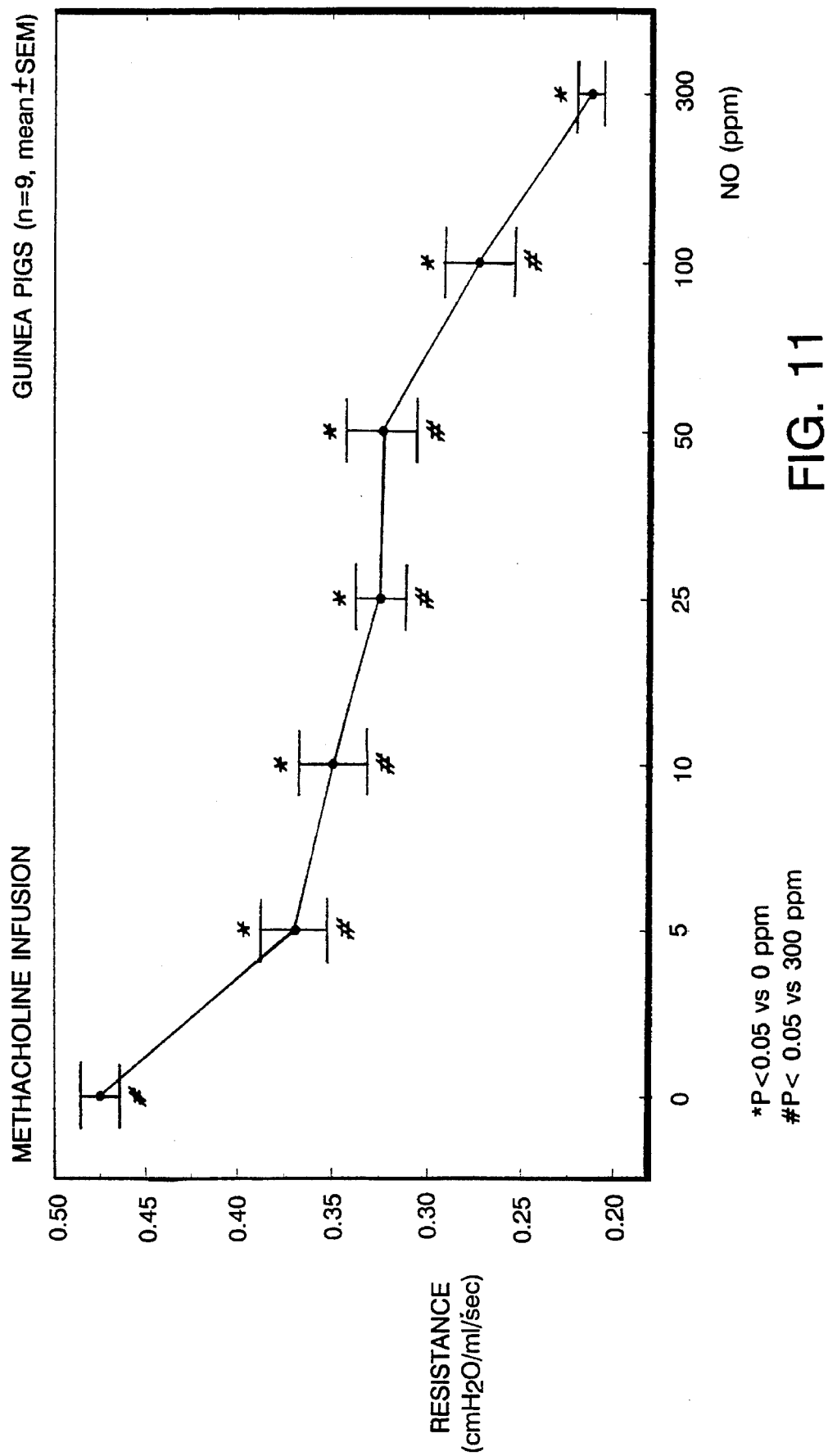
FIGS. 11 and 12 are graphs illustrating the dose-response curve observed when nine experimentally bronchoconstricted guinea pigs were treated with various concentrations of NO gas, with response measured as lung resistance (FIG. 11) or as a percentage of the maximal lung resistance observed (FIG. 12).
Figure 12:
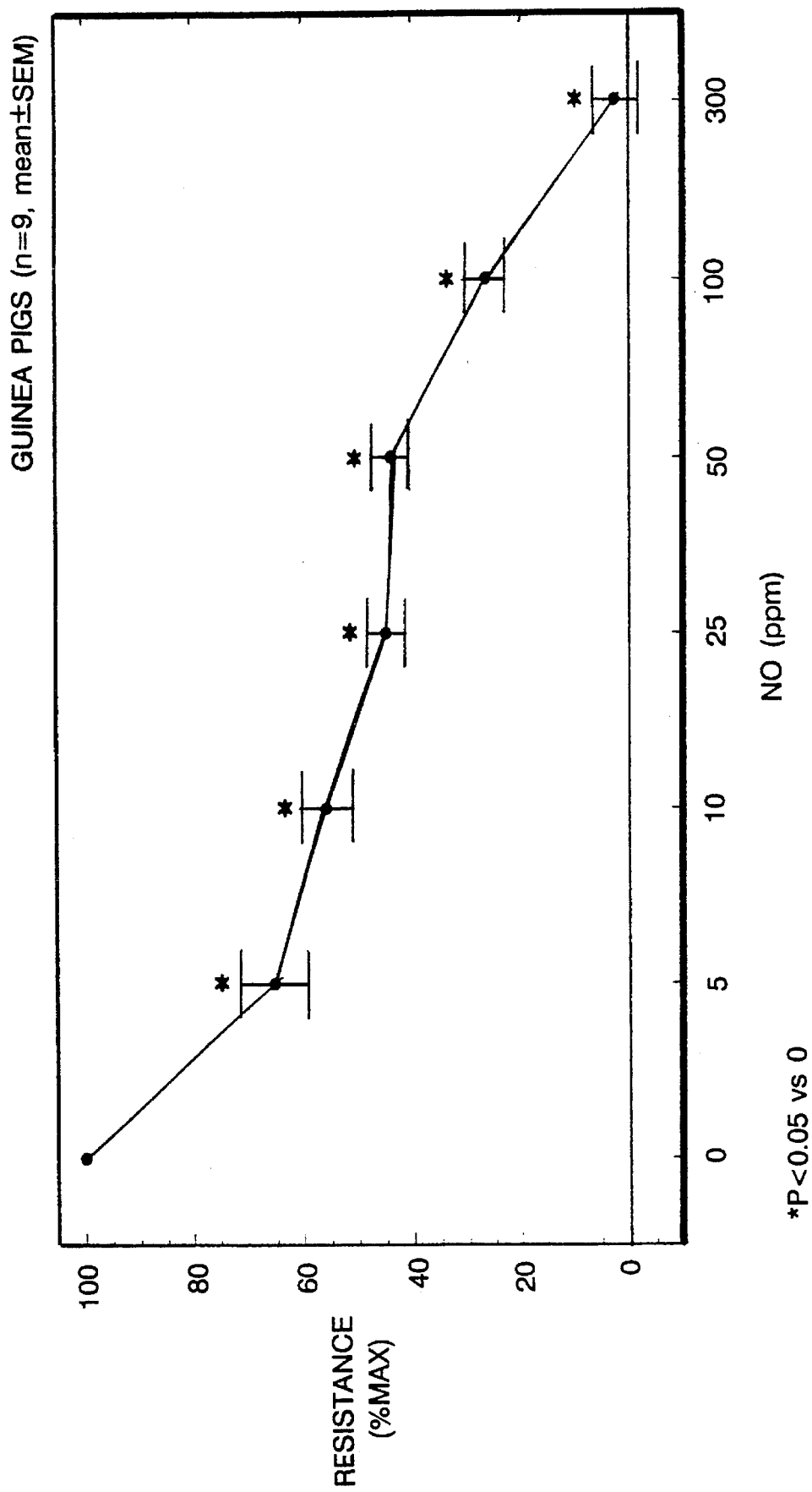

Inhalation of nitric oxide-containing gas mixtures produced a consistent, rapid and profound reduction of lung resistance and an increase of lung compliance (FIGS. 9–12). Onset of dilation was rapid, beginning within a few seconds after inhalation. Nitric oxide inhalation reversed the profound bronchoconstriction caused by methacholine infusion, but also decreased the baseline bronchomotor tone of the anesthetized guinea pig without a methacholine infusion (FIG. 8). Nitric oxide inhalation produced bronchodilation at very low doses (5 ppm), although a greater and more rapid reduction of airway resistance was obtained at 100 or 300 ppm NO (FIGS. 10, 11 and 12). Complete reversal of methacholine bronchoconstriction occurred at 300 ppm NO. There was no tolerance produced by NO breathing, since breathing 100 ppm NO effectively and stably reduced the airway resistance for one hour (FIG. 13). Methemoglobin levels remained below 5% after one hour of breathing 100 ppm NO. This model of producing airway constriction by methacholine infusion produced stably increasing levels of airway resistance for up to one hour (see FIG. 13), establishing the reliability and reproduceability of the above-described studies on the efficacy of NO as a bronchodilator.

During a methacholine infusion, the bronchodilating effects of No are additive with the effects of inhaling a commonly nebulized bronchodilator, the $\beta_2$ agonist, terbutaline (FIG. 14). We have observed this additive bronchodilating effect to occur whether NO gas is administered before (FIG. 14) or after (FIG. 15) terbutaline. SNAP, a nitric oxide donor molecule, was nebulized for 20 breaths into the airways of 5 methacholine-bronchoconstricted guinea pigs. In each animal a prompt and profound reduction of lung resistance was produced which lasted about 15 minutes (FIG. 16). Thus, inhalation of NO donor compounds can also produce bronchodilation.

Other embodiments of the invention are within the following claims.

What is claimed is:

1. A method for treating or preventing reversible pulmonary vasoconstriction in a mammal, which method comprises providing gaseous nitric oxide (NO) mixed, immediately prior to inhalation, with an oxygen-containing gas to form a gas mixture containing a therapeutically effective concentration of NO; and causing a mammal in need of such treatment or prevention to inhale a therapeutically effective amount of said NO-containing gas mixture.

2. The method of claim 1, wherein said pulmonary vasoconstriction is acute pulmonary vasoconstriction.

3. The method of claim 1 wherein said mammal has or is at risk of developing a clinical condition selected from the group consisting of pneumonia, traumatic injury, aspiration or inhalation injury, fat embolism in the lung, acidosis, inflammation of the lung, adult respiratory distress syndrome, acute mountain sickness, post cardiac surgery acute pulmonary hypertension, persistent pulmonary hypertension of the newborn, perinatal aspiration syndrome, hyaline membrane disease, acute pulmonary thromboembolism, acute pulmonary edema, heparin-protamine reactions, sepsis, hypoxia, asthma, and status asthmaticus.

4. The method of claim 1, wherein said pulmonary vasoconstriction is chronic pulmonary vasoconstriction which has a reversible component.

5. The method of claim 1, wherein said mammal has or is at risk of developing a clinical condition selected from the group consisting of chronic pulmonary hypertension, bronchopulmonary dysplasia, chronic pulmonary thromboembolism, idiopathic pulmonary hypertension, and chronic hypoxia.

6. The method of claim 1, wherein the concentration of NO in said NO-containing gas mixture is within a predetermined concentration range, and said NO-containing gas mixture is inhaled for at least three minutes.

7. The method of claim 1 wherein said concentration is at least 5 ppm.

8. The method of claim 7 wherein said concentration is 180 ppm or less.

9. The method of claim 1 wherein said concentration is at least 40 ppm.

10. The method of claim 1, wherein said concentration is at least 80 ppm.

11. The method of claim 1, wherein said NO-containing gas mixture comprises nitric oxide, oxygen, and nitrogen gases.

12. The method of claim 11, wherein said No-containing gas mixture comprises between 20–99% oxygen gas by volume.

13. The method of claim 1, wherein said mammal is a human.

14. The method of claim 1, wherein said NO-containing gas mixture is inhaled in the absence of tobacco smoke.

15. A method for diagnosing the reversibility of chronic pulmonary vasoconstriction in a mammal, which method comprises (a) measuring said mammal's PAP, (b) providing gaseous NO mixed, immediately prior to inhalation, with an oxygen-containing gas to form an NO-containing gas mixture; (c) causing said mammal to inhale said NO-containing gas mixture for a period of time, and (d) measuring said mammal's PAP during said period.

16. A method for treating or preventing bronchoconstriction in a mammal, which method comprises providing gaseous NO mixed, immediately prior to inhalation, with an oxygen-containing gas to form a gas mixture containing a therapeutically-effective concentration of NO, and causing a mammal in need of such treatment or prevention to inhale a therapeutically effective amount of said NO-containing gas mixture.

17. The method of claim 16, wherein said mammal is a human.

18. The method of claim 16, wherein said NO-containing gas mixture is inhaled in the absence of tobacco smoke.

19. The method of claim 16, comprising the additional step of, following said inhalation of said NO-containing gas mixture, causing said mammal to inhale a therapeutically-effective dose of a bronchodilator compound in liquid or solid form.

20. The method of claim 19, wherein said bronchodilator compound is inhaled with a gas mixture comprising nitric oxide.

21. The method of claim 19, wherein said bronchodilator compound is a nitric oxide-releasing compound.

22. The method of claim 21, wherein said bronchodilator compound is S-nitroso-N-acetylpenicillamine, S-nitrosocysteine, nitroprusside, nitrosoguanidine, glyceryl trinitrate, isoamyl nitrite, inorganic nitrite, azide, or hydroxylamine.

23. The method of claim 19, wherein said bronchodilator compound is an anticholinergic agent, a $\beta_2$ agonist, a methyl xanthine, a calcium-channel shocker, a glucocorticoid drug, or cromolyn sodium.

24. The method of claim 16, wherein said bronchoconstriction is associated with asthma.

25. A method of improving gas exchange in the lungs of a mammal, said method comprising providing gaseous NO mixed, immediately prior to inhalation, with an oxygen-containing gas to form a gas mixture containing a therapeutically-effective concentration of NO, and causing said mammal to inhale said NO containing gas mixture.

26. The method of claim 25, wherein said mammal is hypoxic.

27. The method of claim 26, wherein said mammal is a human suffering from a lung injury.

28. The method claim 25, wherein said inhalation is accomplished in the absence of tobacco smoke.

29. The method of claim 25, wherein said NO-containing gas mixture comprises at least 1 ppm NO in air, $O_2$, or an air/$O_2$ mixture.

30. An inhaler device comprising a housing defining (a) a chamber containing an inhalable pharmaceutically-active agent and (b) a lumen in communication with said chamber; and a vessel containing pressurized gas comprising at least 1 ppm nitric oxide, said vessel having a mechanism for controllably releasing said gas into said chamber, thereby suspending said agent in said released gas; said lumen being configured to route said released gas into the respiratory system of a patient.

31. The device of claim 30, wherein said pharmaceutically-active agent comprises a bronchodilator compound in liquid or solid form.

32. The device of claim 31, wherein said compound comprises an anticholinergic agent, a $\beta_2$ agonist, a methylxanthine, a calcium-channel blocker, a glucocorticoid drug, or cromolyn sodium.

33. The device of claim 30, wherein said pharmaceutically-active agent comprises a nitric oxide-releasing compound.

34. The device of claim 33, wherein said compound is selected from the group consisting of S-nitroso-N-acetylpenicillamine, S-nitrosocysteine, nitroprusside, nitrosoguanidine, glyceryl trinitrate, isoamyl nitrite, inorganic nitrite, azide, and hydroxylamine.

35. The device of claim 30, wherein said pharmaceutically-active agent comprises an antimicrobial agent.

36. The device of claim 35, wherein said antimicrobial agent comprises an antibiotic.

37. The device of claim 35, wherein said antimicrobial agent comprises pentamidine.

38. The device of claim 30, wherein said pharmaceutically-active agent comprises a surfactant suitable for the treatment of hyaline membrane disease.

39. The device of claim 30, wherein said vessel also has a mechanism for controllably releasing said gas into said lumen, in a manner that bypasses said chamber.

* * * * *

UNITED STATES PATENT AND TRADEMARK OFFICE
CERTIFICATE OF CORRECTION

PATENT NO. : 5,485,827

DATED : January 23, 1996

INVENTOR(S) : Warren M. Zapol, et al

It is certified that error appears in the above-indentified patent and that said Letters Patent is hereby corrected as shown below:

Cover page, [54] Title, "PLUMONARY" should be --PULMONARY--.

Cover page, [56] References Cited, U.S. PATENT DOCUMENTS, in the "5,155,137" reference, "Keeer" should be --Keefer--.

Cover page, [56] References Cited, OTHER PUBLICATIONS, in the "Blomqvist" reference, "Pulumonary" should be --Pulmonary--.

Cover page, [56] References Cited, OTHER PUBLICATIONS, "Fractacci" should be --Fratacci--.

Cover page, [56] References Cited, OTHER PUBLICATIONS, in the "Pepke-Zaba" reference, "Pulomonary" should be --Pulmonary--.

Cover page 2, [56] References Cited, OTHER PUBLICATIONS, second column, in the "Stavert" reference, "Lahnert" should be --Lehnert--.

UNITED STATES PATENT AND TRADEMARK OFFICE
CERTIFICATE OF CORRECTION

PATENT NO. : 5,485,827

DATED : January 23, 1996

INVENTOR(S) : Warren M. Zapol, et al

Page 2 of 4

It is certified that error appears in the above-indentified patent and that said Letters Patent is hereby corrected as shown below:

Cover page 2, [56] References Cited, OTHER PUBLICATIONS, second column, in the "Borland" reference, "2:65-63" should be --2:56-63--.

Cover page 2, [56] References Cited, OTHER PUBLICATIONS, second column, in the "Arnold" reference, "198:943-936" should be --198:934-936--.

Cover page 2, [56] References Cited, OTHER PUBLICATIONS, second column, after the "Southern" reference, a new entry should start with the "Garg" reference.

Cover page 2, [56] References Cited, OTHER PUBLICATIONS, second column, insert the following --Inhaled Nitric Oxide (NO): A Selective Pulmonary Vasodilation Reversing Human Hypoxic Pulmonary Vasoconstriction (HPV), Circulation 84:361, 1991--.

Cover page 2, [56] References Cited, OTHER PUBLICATIONS, second column, last reference, "Physican's" should be --Physician's--.

Col. 1, line 2, "PLUMONARY" should be --PULMONARY--.

Col. 4, line 2, "bronchdilator" should be --bronchodilator--.

Col. 4, line 61, "$_2$" should be --$O_2$--.

UNITED STATES PATENT AND TRADEMARK OFFICE
CERTIFICATE OF CORRECTION

PATENT NO. : 5,485,827
DATED : January 23, 1996
INVENTOR(S) : Warren M. Zapol, et al It is certified that error appears in the above-indentified patent and that said Letters Patent is hereby corrected as shown below:

Col. 6, line 55, "bronchconstriction" should be --bronchoconstriction--.

Col. 9, line 11, after "$N_2$)", insert --,--.

Col. 9, line 57, "repiratory" should be --respiratory--.

Col. 10, line 24, "is" should be --are--.

Col. 10, line 37, "non-bronchconstricted" should be --non-bronchoconstricted--.

Col. 10, line 54, "longterm" should be --long-term--.

Col. 19, line 30, "cicuit" should be --circuit--.

Col. 20, Table 3, under #1, line 5, "$Q_A/Q_r$%" should be --$Q_A/Q_T$%--.

Col. 25, line 11, after "(SNAP", delete the ",", and insert --)--.

UNITED STATES PATENT AND TRADEMARK OFFICE
CERTIFICATE OF CORRECTION

PATENT NO. : 5,485,827
DATED : January 23, 1996
INVENTOR(S) : Warren M. Zapol, et al It is certified that error appears in the above-indentified patent and that said Letters Patent is hereby corrected as shown below:

Col. 25, line 63, "No" should be --NO--.

Col. 26, line 57, "No-containing" should be --NO-containing--.

Col. 27, lines 33-34, "methyl xanthine" should be --methylxanthine--.

Col. 27, line 34, "shocker" should be --blocker--.

Signed and Sealed this

Sixth Day of August, 1996

Attest:

BRUCE LEHMAN

*Attesting Officer*     *Commissioner of Patents and Trademarks*

US005485827C1

(12) EX PARTE REEXAMINATION CERTIFICATE (7730th)
United States Patent
Zapol et al.

(10) Number: US 5,485,827 C1
(45) Certificate Issued: Sep. 14, 2010

(54) METHODS AND DEVICES FOR TREATING PULMONARY VASOCONSTRICTION AND ASTHMA

(76) Inventors: Warren M. Zapol, 182 Holden Wood Rd., Concord, MA (US) 01742; Claes Frostell, Vikavaegen 10, F-16140 Bromma (SE)

Reexamination Request:
No. 90/009,319, Nov. 4, 2008
No. 90/010,354, Dec. 11, 2008

Reexamination Certificate for:
Patent No.: 5,485,827
Issued: Jan. 23, 1996
Appl. No.: 08/384,792
Filed: Feb. 10, 1995

Certificate of Correction issued Aug. 6, 1996.

Related U.S. Application Data

(63) Continuation of application No. 07/767,234, filed on Sep. 27, 1991, now abandoned, which is a continuation-in-part of application No. 07/622,865, filed on Dec. 5, 1990, now abandoned.

(51) Int. Cl.
*A61M 11/00* (2006.01)

(52) U.S. Cl. .............................. 128/200.14; 128/200.23; 128/203.15

(58) Field of Classification Search .................. None
See application file for complete search history.

(56) References Cited

U.S. PATENT DOCUMENTS

| | | |
|---|---|---|
| 3,001,524 A | 9/1961 | Maison et al. |
| 3,762,427 A | 10/1973 | Mollering |
| 3,809,294 A | 5/1974 | Torgeson |
| 3,848,617 A | 11/1974 | Dray |
| 3,895,642 A | 7/1975 | Bird et al. |
| 3,910,222 A | 10/1975 | Metivier |
| 3,993,095 A | 11/1976 | Flynn |
| 4,148,313 A | 4/1979 | Bird et al. |
| 4,219,038 A | 8/1980 | Lubitzsch et al. |
| 4,279,250 A | 7/1981 | Valenta et al. |
| 4,340,045 A | 7/1982 | Manley |
| 4,542,740 A | 9/1985 | Kleinschmidt et al. |
| 4,889,116 A | 12/1989 | Taube |
| 4,905,685 A | 3/1990 | Olsson et al. |
| 5,427,089 A | 6/1995 | Kraemer |
| 5,427,797 A | 6/1995 | Frostell et al. |
| 5,485,827 A | 1/1996 | Zapol et al. |
| 5,558,083 A | 9/1996 | Bathe et al. |
| 5,651,358 A | 7/1997 | Briend et al. |
| 5,722,392 A | 3/1998 | Skimming et al. |
| 5,873,359 A | 2/1999 | Zapol et al. |
| 5,885,621 A | 3/1999 | Head et al. |
| 7,516,742 B2 | 4/2009 | Stenzler et al. |

FOREIGN PATENT DOCUMENTS

| | | |
|---|---|---|
| DE | 1933266 | 7/1969 |
| DE | 2461637 | 12/1974 |
| DE | 2553165 | 11/1975 |
| EP | 0073219 | 9/1982 |
| EP | 0089070 B1 | 9/1983 |
| EP | 0 287 068 | 4/1988 |
| EP | 0 560 928 | 9/1997 |
| GB | 2178958 A | 2/1987 |
| GB | 2 054 387 | 2/1991 |
| GB | 2 283 179 | 5/1995 |
| JP | 46-1447 | 9/1971 |
| JP | 47-11797 | 6/1972 |
| JP | 49-94189 | 9/1974 |
| JP | 50-49886 | 5/1975 |
| JP | 56-5667 | 1/1981 |
| JP | 56-54858 | 5/1981 |
| JP | 59-44271 | 3/1984 |
| JP | 62-56040 | 4/1987 |
| JP | 02-131775 | 5/1990 |
| JP | 2-291868 | 12/1990 |
| JP | 02-291869 | 12/1990 |
| JP | 06-23541 | 3/1994 |
| JP | 06-197969 | 7/1994 |
| JP | 07-37197 | 7/1995 |
| JP | 07-194705 | 8/1995 |
| JP | 07-299144 | 11/1995 |
| WO | WO 82/03014 | 9/1982 |
| WO | WO 82/03014 PUB 6 | 9/1982 |
| WO | WO 92/10288 | 6/1992 |

OTHER PUBLICATIONS

Buga, et al., "Endothelium–derived Nitric Oxide Relaxes Nonvascular Smooth Muscle", Eur. J. Pharmacology, 161:61–72, 1989.

Hirshleifer et al., "Nitrates in Treatment of Bronchial Asthma", Chest. 39:275–83, 1961.

How Things Work, The Universal Encyclopedia of Machines, vol. I (1975), pp. 440–441.

How Things Work, The Universal Encyclopedia of Machines, vol. II (1975), pp. 404–405.

"Patent for Linde Product INOtherapy/TM Declared Invalid in Europe," Press announcement in Linde, Nov. 17, 2004.

Szego, "Review of human phase III. Study of Nitromint spray" Ther. Hung., 37(3):165–167, 1989. Abstract.

Gruetter et al., "Relaxation of Bovine Coronary Artery and Activation of Coronary Arterial Guanylate Cyclase by Nitric Oxide, Nitroprusside and Carcinogenic Nitrosoamine" Journal of CyclicNucleotide Research 5(3):211–224, 1979.

Palevsky et al. "Prostacyclin and Acetylcholine as Screening Agents for Acute Pulmonary Vasodilator Responsiveness in Primary Pulmonary Hypertension" Circulation 82(6): 2018–2026, 1990.

(Continued)

*Primary Examiner*—Brenda Brumback

(57) ABSTRACT

A method for treating or preventing bronchoconstriction or reversible pulmonary vasoconstriction in a mammal, which method includes causing the mammal to inhale a therapeutically-effective concentration of gaseous nitric oxide or a therapeutically-effective amount of a nitric oxide-releasing compound, and an inhaler device containing nitric oxide gas and/or a nitric oxide-releasing compound.

OTHER PUBLICATIONS

[No Authors Listed] "Inhaled Nitric Oxide in Full–Term and Nearly Full–Term Infants with Hypoxic Respiratory Failure" *New England Journal of Medicine*, 336(9):597–604 (1997).

Adatia et al., "Diagnostic and Therapeutic Uses of Inhaled Nitric Oxide In Congenital Heart Disease", *Lung Biology in Health and Disease*, vol. 98, Chapter 18, pp. 365, 368, 375, 379, 383, and 386 (1997).

Abman et al., "Failure of Postnatal Adaptation of the Pulmonary Circulation after Chronic Intrauterine Pulmonary Hypertension in Fetal Lambs." *J. Clin. Invest.*, 83:1849–1858, Jun. 1989.

Abman et al., "Role of endothelium–derived relaxing factor during transition of pulmonary circulation at birth." *Am. J. Physiol.* 259(Heart Circ. Physiol 28): H1921–H1927, 1990.

Anderson et al., "Proceedings of the British Thoracic Society," *Thorax*, 44:314P–367P (1989).

Ardehali et al., "Inhaled Nitric Oxide for Pulmonary Hypertension after Heart Transplantation," *Transplantation*, 72:638–641 (2001).

Barnes and Lisbon, *Respiratory Care Practice*, Year Book Medical Publishers, Inc., Chicago, pp. 305 and 374 (1988).

Borland and Higenbottam, "A simultaneous single breath measurement of pulmonary diffusing capacity with nitric oxide and carbon monoxide." *Eur. Respir. J.*, 2:56–63, 1989.

Borland et al., "The Fate of Inhaled Nitric Oxide." *Clinical Science*, p. 37P, 1983.

Bush et al., "Does prostacyclin enhance the selective pulmonary vasodilator effect of oxygen in children with congenital heart disease?" *Circulation*, 74(1):135–144. 1986.

Bush et al., "Effect of infused adenosine on cardiac output and systemic resistance in normal subjects." *Br. J. Clin. Pharmac.*, 27:165–171, 1989.

Channick et al., "Inhaled Nitric Oxide Reverses Hypoxic Pulmonary Vasoconstriction in Dogs." *Chest*, 105(6):1842–1847, Jun. 1994.

Channick et al., "Pulsed Delivery of Inhaled Nitric Oxide to Patients With Primary Pulmonary Hypertension." *Chest*, 109(6):1545–1549, Jun. 1996.

Clark et al., "Low–Dose Nitric Oxide Therapy for Persistent Pulmonary Hypertension of the Newborn" *The New England Journal Of Medicine* 342(7): 469–474 (2000).

Date et al., "Inhaled Nitric Oxide Reduces Human Lung Allograft Dysfunction," *The Journal of Thoracic & Cardiovascular Surgery*, 111(5):913–919 (1996). [retrieved online Dec. 1, 2003] Retrieved from Internet at URL:http://gateway1.ovid.com/ovidweb.cgi.

Datex–Ohmeda, INOvent delivery system, Operation and Maintenance Manual, title pages, and pp. 4–3 and 6–16 (1999).

Davidson et al., "Influence of Aging on Pulmonary Hemodynamics in a Population Free in Coronary Artery Disease," *American Journal of Cardiology*, 65:1454–1458 (1990).

Dellinger et al., "Effects of inhaled nitric oxide in patients with acute respiratory distress syndrome: Results of a randomized phase II trial." *Crit. Care Med.*, 26(1):15–23, 1998.

Dellinger, R. Philip, "Pathophysiology, Monitoring, and Management of the Ventilator–Dependent Patient: Considerations for Drug Therapy, Emphasis on Stress Ulcer Prophylaxis." *Annals of Pharmacotherapy*, 24:S8–S11, Nov. 1990.

Dellinger, R. Philip, and Perillo, Joseph. "Mediator modulation therapy of severe sepsis and septic shock: Does it work?" *Crit. Care Med.*, 32(1):282–286 (2004).

Department of Health and Human Services, Public Health Services, Grant Application, "Heparin–protamine lung vasoconstriction at heart surgery", Warren M. Zapol, Oct. 19, 1989.

Department of Health and Human Services, Public Health Services, Investigational New Drug Application, (IND), Warren M. Zapol, M.D., Oct. 2, 1991.

Dinh Xuan et al., "Non–prostanoid Endothelium–derived Vasoactive Factors." *Journal of Intl. Med. Research*, 17:305–315, 1989.

Doyle et al., "Oxidation of Nitrogen Oxides by Bound Dioxygen in Hemoproteins" *Journal of Inorganic Biochemistry* 14:351–358 (1981).

Dupuy et al., "Bronchodilator Action of Inhaled Nitric Oxide in Guinea Pigs." *J. Clin. Invest.* 90:421–428, Aug. 1992.

Depuy et al., "Bronchial Effects of Nitric Oxide" *Lung Biology in Health and Disease* vol. 98, Chapter 15, pp. 285, 302 and 303 (1997).

Estagnasie et al., "Use of Inhaled Nitric Oxide to Reverse Flow through a Patent Foramen Ovale during Pulmonary Embolism," *Annals of Internal Medicine*, 120(9):757–759 (1994). [retrieved online on Dec. 1, 2003] Retrieved from Internet:URL:http://gateway1.ovid.com/ovidweb.cgi.

Eubanks and Bone, *Principles and Applications of Cardiorespiratory Care Equipment*, Mosby–Year Book, Inc., St. Louis, MO, p. 39 (1994).

Fellâhi et al., "Inhaled Nitric Oxide–induced Closure of a Patent Foramen Ovale in a Patient with Acute Respiratory Distress Syndrome and Life–threatening Hypoxemia," *Anesthesiology*, 83(3):635–638 (1995).

Fineman et al., "Selective pulmonary vasodilation with ATP–MgCl$_2$ during pulmonary hypertension in lambs." *J. Appl. Physiol.*, 69(5):1836–1842, 1990.

Fratacci et al., "Inhaled Nitric Oxide: A Selective Pulmonary Vasodilator of Heparin–Protamine Vasoconstriction in Sheep." *Anesthesiology*, 75:990–999, 1991.

Frostell et al., "Inhaled Nitric Oxide: A Selective Pulmonary Vasodilator Reversing Hypoxic Pulmonary Vasoconstriction." *Circulation*, 83:2038–2047 (1991).

Fullerton et al., "Effective Control of Pulmonary Vascular Resistance with Inhaled Nitric Oxide after Cardiac Operation," *The Journal of Thoracic & Cardiovascular Surgery*, 111(4):753–763 (1996). [retrieved online Dec. 1, 2003] Retrieved from the Internet at URL:http://gateway1.ovid.com/ovidweb.cgi.

Gerlach et al., "Low Levels of Inhaled Niric Oxide In Acute Lung Injury" *Lung Biology in Health and Disease*, vol. 98, Chapter 14, pp. 271–273, 282, and 283 (1997).

Gibson et al., "Further studies on the kinetics and equilibria of the reactions of nitric oxide with haemoproteins," *Proceedings of the Royal Society*, 163(991):197–205 (1965).

Goldman et al., "Nitric Oxide is Superior to Prostacyclin for Pulmonary Hypertension after Cardiac Operations," *Ann. Thorac. Surg.*, 60:300–306 (1995).

Gruetter et al., "Relationship between Cyclic Guanosine 3':5'–Monophosphate Formation and Relaxation of Coronary Arterial Smooth Muscle by Glyceryl Trinitrate, Nitroprusside, Nitrite and Nitric Oxide: Effects of Methylene Blue and Methemoglobin," *The Journal of Pharmacology and Experimental Therapeutics*, 219(1):181–186 (1981).

Guenard et al., "Determination of lung capillary blood volume and membrane diffusing capacity in man by the measurements of NO and CO transfer." *Respiration Physiology,* 70:113–120 (1987).

Gulati et al., "Nitric Oxide: Lifesaving Measure for Pulmonary Vasospasm After Modified Blalock–Taussig Shunt," *Ann. Thorac. Surg.,* 74:1700–1702 (2002).

Head et al., "Low concentrations of Nitric Oxide Increase Oxygen Affinity of Sickle Erythrocytes In Vitro and In Vivo," *J. Clin. Invest.* 100(5), 1193–1198 (1997).

Heinonen et al., "Administration of nitric oxide into open lung regions: delivery and monitoring," *British Journal of Anethesia,* 90(3):338–342, 2003.

Hess et al., "Use of Inhaled Nitric Oxide in Patients with Acute Respiratory Distress Syndrome," *Respiratory Care,* 41(5):424–446 (1996).

Higenbottam et al., "Inhaled 'Endothelium Derived–Relaxing Factor' (EDRF) in Primary Hypertension (PPH)," *Amer. Rev. of Respiratory Disease,* 1988 Annual Meeting Pamphlet, May 8–11, 1988.

Higenbottam, "Primary pulmonary hypertension." *British Medical Journal,* 293:1456–1457, Dec., 1986.

Higenbottam, "Survival in primary pulmonary hypertension (PPH); A comparison of vasodilator treatment and heart–lung transplantation, with the Mayo Clinic retrospective analysis of survival", *American Thoracic Society,* 1989 Abstract Form (Abstract).

Hugod, "Effect of Exposure to 43 ppm Nitric Oxide and 3.6 ppm Nitrogen Dioxide on Rabbit Lung: A Light and Electron Microscopic Study," *Int. Arch. Occup. Environ. Health,* 42:159–167 (1979).

Hugod, "Ultrastructural Changes of the Rabbit Lung after a 5 ppm Nitric Oxide Exposure" *Archives of Environmental Health,* pp. 12–17, Jan./Feb. 1979.

Ignarro et al., "Molecular Mechanisms of Vasodilatation" *Cardiovascular and Renal Function,* 12:259–288 (1984).

Imanaka et al., "Inaccuracies of Nitric Oxide Delivery Systems during Adult Mechanical Ventilation," *Anesthesiology,* 86:676–688 (1997).

Johnson, *The Handbook of Fluid Dynamics,* CRC Press LLC, Boca Raton, pp. 2–1–2–4, 1998.

Journois et al., "Inhaled nitric oxide as a therapy for pulmonary hypertension after operations for congenital heart defects," *J. Thorac. Cardiovasc. Surg.,* 107:1129–1135 (1994).

Katayama et al., "Minimizing the Inhaled Dose of NO With Breath–by–Breath Delivery of Spikes of Concentrated Gas." *Circulation,* 98:2429–2432, 1998.

Kim et al., "Inhaled Nitric Oxide for Perioperative Management of an Adult Patient with Atrial Septal Defect and Severe Pulmonary Hypertension," *Journal of Cardiothoracic and Vascular Anesthesia,* 16(6):746–748 (2002).

Kinsella and Abman, "Recent developments in the pathophysiology and treatment of persistent pulmonary hypertension of the newborn," *The Journal of Pediatrics,* 126:853–864 (1995).

Kinsella et al., "Inhalational Nitric Oxide Therapy for Persistent Pulmonary Hypertension of the Newborn (Commentaries)", *Pediatrics,* 91(5):997–998 (1993).

Kinsella et al., "Inhaled nitric oxide in premature neonates with severe hypoxaemic respiratory failure: a randomised controlled trial," *Lancet,* 354:1061–1065 (1999).

Koff et al., *Neonatal and pediatric respiratory care,* The C.V. Mosby Company, St. Louis, p. 231 (1988).

Krasuski et al., "Inhaled Nitric Oxide Selectively Dilates Pulmonary Vasculature in Adult Patients with Pulmonary Hypertension, Irrespective of Etiology," *J. Am. Coll. Cardiol.,* 36:2204–2211 (2000).

Lewis, *Hawley's Condensed Chemical Dictionary.,* John Wiley & Sons, Inc., New York, p. 754, 2001.

Lu et al., "Dose–Response Curves of Inhaled Nitric Oxide with and without Intravenous Almitrine in Nitric Oxide–responding Patients with Acute Respiratory Distress Syndrome." *Anesthesiology,* 83(5):929–943, Nov. 1995.

Lundin et al., "Inhalation of nitric oxide in acute lung injury: results of a European multicentre study," *Intensive Care Med.,* 25:911–919 (1999).

Macintosh et al., *Physics for the Anesthetist,* F.A. Davis Company, Philadelphia, pp. 270–283, 1963.

Maeda et al., "A Kinetic Study on Functional Impairment of Nitric Oxide–Exposed Rat Erythrocytes" *Environmental Health Perspectives,* 73:171–177 (1987).

Marshall et al., "A T–piece for use with a blower–humidifier." *Anesthesia,* 22:494–496, Jul. 1967.

Maxey et al., "Beneficial Effects of Inhaled Nitric Oxide in Adult Cardiac Surgical Patients," *Ann. Thorac. Surg.,* 73:529–533 (2002).

Mellion, et al., "Evidence for the Inhibitory Role of Guanosine 3',5'—Monophosphate in ADP–Induced Human Platelet Aggregation in the Presence of Nitric Oxide and Related Vasodilators," *Blood* 57(5):946–955 (1981).

Meyer and Piiper, "Nitric oxide (NO), a new test gas for study of alveolar–capillary diffusion," *Eur. Respir. J.,* 2(6):494–496 (1989).

Michael et al., "Inhaled Nitric Oxide Versus Conventional Therapy," *Am. J. Respir. Crit. Care Med.,* 157:1372–1380 (1998).

Miller et al., "Guidelines for the safe administration of inhaled nitric oxide." *Archives of Disease in Childhood,* 70:F47–F49, 1994.

Miller et al., "Pulmonary Vascular Smooth–Muscle Regulation: The Role of Inhaled Nitric Oxide Gas," *Respiratory Care,* 37(10):1175–1185 (1992).

Moinard and Guenard, "Determination of lung capillary blood volume and membrane diffusing capacity in patients with COLD using the NO–CO method," *Eur. Respir. J.,* 3:318–322 (1990).

Nakajima et al., "Biological Effects of Nitrogen Dioxide and Nitric Oxide," *Nitrogen Oxides and Their Effects on Health,* Chapter 8, pp. 121–141 (1980).

Oda et al., "Long–term Exposure to Nitric Oxide in Mice," *J. Jap. Soc. Air Pol.,* 11:150 (1976). (including English abstract).

Oda et al., "Nitrosyl–Hemoglobin Formation in the Blood of Animals Exposed to Nitric Oxide." *Archives of Environmental Health,* 30:453–456, Sep. 1975.

Pearl, "The pulmonary circulation," *Current Opinion in Anaesthesiology,* 5:848–854 (1992).

Pinelli et al., "Inhaled Nitric Oxide as an Adjunct to Pulmonary Thromboendarterectomy," *Ann. Thorac. Surg.,* 61:227–229 (1996).

Puybasset et al., "Inhaled Nitric Oxide Reverses the Increase in Pulmonary Vascular Resistance Induced by Permissive Hypercapnia in Patients with Acute Respiratory Distress Syndrome," *Anesthesiology,* 80:1254–1267 (1994).

Rabkin et al., "Nitric Oxide for the Treatment of Postpneumonectomy Pulmonary Edema," *Ann. Thorac. Surg.,* 72:272–274 (2001).

Radomski et al., "Endogenous Nitric Oxide Inhibits Human Platelet Adhesion to Vascular Endothelium" *The Lancet,* 2(8567): 1057–1058 (1987).

Razavi et al., "Effects of inhaled nitric oxide in a mouse model of sepsis–induced acute lung injury." *Crit. Care Med.,* 30(4):868–873, 2002.

Reiter et al., "Cell–free hemoglobin limits nitric oxide bioavailability in sickle–cell disease." *Nature Medicine,* 8(12):1383–1389, Dec. 2002.

Rich, "Primary Pulmonary Hypertension," *Principles of Internal Medicine 12th Edition,* Chapter 212:1087–1090 (McGraw–Hill, Inc. New York) (1991).

Roberts et al., "Inhaled nitric oxide (NO): A selective pulmonary vasodilator for the treatment of persistent pulmonary hypertension of the newborn (PPHN)", Abstract, 64th Scientific Sessions, American Heart Association, Nov. 11–14, 1991.

Roberts et al., "Inhaled Nitric Oxide and Persistent Pulmonary Hypertension of the Newborn," *N. Engl. J. Med.,* 336:605–610 (1997).

Roberts et al., "Inhaled Nitric Oxide and Persistent Pulmonary Hypertension of the Newborn," *The New England Journal of Medicine,* 336(9):605–610 (1997). [retrieved online Dec. 3, 2003] retrieved from Internet at URL:http://gateway1.ovid.com/ovidweb.cgi.

Roberts et al., "Inhaled nitric oxide in persistent pulmonary hypertension of the newborn," *Lancet,* 340:818–819 (1992).

Roberts et al., "Inhaled Nitric Oxide In Neonatal Pulmonary Hypertension and Severe Respiratory Distress Syndrome: Experimental and Clinical Studies" *Lung Biology in Health and Disease* vol. 98, Chapter 17, pp. 333, 349, 362 (1997).

Roberts et al., "Inhaled Nitric Oxide Reverses Pulmonary Vasoconstriction in the Hypoxic and Acidotic Newborn Lamb" *Circulation Research,* 72(2): 246–254 (1993).

Rocca et al., "Inhaled nitric oxide administration during one–lung ventilation in patients undergoing thoracic surgery," *J. Cardiothorac. Vasc. Anesth.,* 15(2):218–223 (2001), Pub Med Abstract.

Rossaint et al., "Efficacy of Inhaled Nitric Oxide in Patients With Severe ARDS." *Chest,* 107(4):1107–1115, Apr. 1995.

Rossaint et al., "Inhaled Nitric Oxide for the Adult Respiratory Distress Syndrome," *N. Engl. J. Med.,* 328:399–405 (1993).

Rossaint et al., "Inhaled nitric oxide improves arterial oxygenation in severe ARDS—a preliminary report", Manuscript for Nitric Oxide Meeting in London, Sep. 1991.

Rossaint et al., "Successful treatment of severe adult respiratory distress syndrome with inhalation of nitric oxide—first clinical experinces", Manuscript for Nitric Oxide Meeting in London, Sep. 1991.

Sancier et al., "Electron Spin Resonance of Nitric Oxide–Hemoglobin Complexes in Solution," *Science,* 137(3532):752–754 (1962).

Sax and Lewis, *Hawley's Condensed Chemical Dictionary,* Van Nostrand Reinhold, New York, pp. 754 and 790 (1987).

Siassi et al., "Persistent Pulmonary Vascular obstruction in newborn infants" *The Journal of Pediatrics* 78(4):610–615 (1971).

Skimming et al., "Calculating Vascular Resistances." *Clin. Cardiol.,* 20:805–808, 1997.

Skimming et al., "Nitric Oxide Administration Using Constant–Flow Ventilation," *Chest,* 108:1065–1072 (1995).

Skimming et al., "Nitric oxide inhalation in infants with respiratory distress syndrome," *J. Pediatr.,* 130:225–230 (1997).

Skimming et al., "Propagation of Nitric Oxide Pool During Controlled Mechanical Ventilation." *Journal of Clinical Monitoring and Computing,* 14:157–164, 1998.

Skimming, "Nitric Oxide Inhalation Therapy for Newborn Infants." *Curr. Probl. Pediatr.,* 27:253–264, 1998.

Stavert et al., "Nitric Oxide and Nitrogen Dioxide as Inducers of Acute Pulmonary Injury When Inhaled at Relatively High Concentrations for Brief Periods." *Inhalation Toxicology,* 2:53–67, 1990.

Sullivan et al., "Nitric oxide successfully used to treat acute chest syndrome of sickle cell disease in a young adolescent," *Crit. Care Med.,* 27–2563–2568 (1999).

Tevaearai et al., "Nitric oxide added to the sweep gas infusion reduces local clotting formation in adult blood oxygenators." *ASAIO J.,* 46(6):719–722, Nov.–Dec. 2000. (PubMed Abstract).

Tierce and Phil, "An Economic Assessment of Inomax (Nitric Oxide) for Inhalation in Neonatal Hypoxemic Respiratory Failure," Epinomics Research, Inc. (Feb. 4, 2001).

Troncy et al., "Should we treat acute respiratory distress syndrome with inhaled nitric oxide?" *The Lancet,* 350(9071):111–112 (1997).

U.S. Department of Health and Human Services, "NIOSH Recommendations for Occupational Safety and Health Standards 1988," *Morbidity and Mortality Weekly Report,* 37(S–7) (Aug. 25, 1988).

Von Nieding and Wagner, "Vergleich der Wirkung von Stickstoffdioxid und Stickstoffmonoxid auf die Lungenfunktion des menschen", Staub–reinhal. Luft 35: 175–178, 1975. (including English translation).

Webert et al., "Effects of inhaled nitric oxide in a rat model of *Pseudomonas aeruginosa* pneumonia," *Crit. Care Med.,* 28:2397–2405 (2000).

Weiner et al., "Preliminary Assessment of Inhaled Nitric Oxide for Acute Vaso–occlusive Crisis in Pediatric Patients with Sickle Cell Disease." *JAMA,* 289(9):1136–1142, Mar. 5, 2003.

Wessel et al., "Delivery and monitoring of inhaled nitric oxide in patients with pulmonary hypertension," *Critical Care Medicine,* 22:930–938 (1994).

Westphal K., "Inhalation of nitric oxide in severe lung failure." *Anesthesiol Reanim.,* 23(6):144–148, 1998. (PubMed Abstract).

Xuan, et al., "Primary pulmonary hypertension: diagnosis, medical and surgical treatment" *Respiratory Medicine* 84:189–197, (1990).

Yoshida et al., "Metabolic Fate of Nitric Oxide," *Int. Arch. Occup. Environ. Health,* 46:71–77 (1980).

Yoshida et al., "On the changes of Nitric Oxide in the airway; experiments with model airway and perfused rabbit lungs", Report of Environmental Science, Mie University No. 6, 1981, pp. 57–60. (including English translation).

Young et al., "Delivery and monitoring of inhaled nitric oxide." *Intensive Care Med.,* 22:77–86, 1996.

Zapol et al., "Nitric Oxide and the Lung." *Am. J. Respir. Crit. Care Med.,* 149:1375–1380, 1994.

Zellers and Vanhoutte, "Endothelium–Dependent Relaxations of Piglet Pulmonary Arteries Augment with Maturation." *Pediatric Research,* 30:176–180, 1991.

"Inventors of landmark treatment for pulmonary hypertension receive national Inventor of the Year award", Press release, Intellectual Property Owners Association, 2003. D60.

"Poison gas kills 100 in Cleveland clinic", New York Times, May 16, 1929. D51.

"Special gases and equipment from Air Products", Air Products Limited pre '82 catalogue, front and rear cover, pp. 3–5 (index pages), and p. 59. D18.

Barash, "Anesthesiology", Journal of Am. Med. Assn., 268:335–337 (1992). D10A.

Blomqvist et al, "Enhanced pneumonia resolution by inhalation of nitric oxide?", Acta Anest. Scand., 37: 110–114, 1993. D10A.

Blythe and Van Heerden, "The pulmonary circulation and selective pulmonary vasodilators", world wide web at anaesthesist.com, last update Feb. 22, 1999. W6.

Butt and Higenbottam, "New therapies for primary pulmonary hypertension", Chest, 105: 21S–25S, Feb. 1994. D7.

Clutton–Brock, John, "Two cases of poisoning by contamination of nitrous oxide with higher oxides of nitrogen during anaesthesia", Brit. Journal of Anaesthesia, 39: 388–392. 1967. D52.

Contractor et al, "Development and evaluation of an inhalation aerosol of nitroglycerin", Journal Pharm. Sc., 63(6): 907, Jun. 1974. D6.

Dinh Xuan and Higenbottam "Non–prostanoid Endothelium derived Vasoactive factors", Journal of Int. Medical Research, 17: 305–315, 1989. AL8A, PUB 3.

Dinh Xuan and Higenbottam, "Estudios clinicos y fisiopatologicos de la prostaciclina y de los factores vasoactivos no prostanoides derivados del endotelio en la enfermedad vascular pulmonar", Estratégias farmacologicas en el paciente grave, Net, Roglan, Benoto, 1991, pp. 408–416. AL8A (including English translation).

Dinh Xuan and Lockhart, "Facteurs non prostanoïdes derives de l'endothelium", Thérapie, 45: 111–118, 1990. AL 8A, PUB 8 (including English abstract from PUBMED, English translation of pp. 115 and 116, and Letter from Air Liquide, Oct. 1, 2002 providing summary of opponent's view).

Dupuy et al, "Bronchodilator action of inhaled nitric oxide in guinea pigs", J. Clin. Invest. 90: 421–428 (1992). D10A.

Fishman et al., "Diagnosis and assessment of PPH", 1998 World Symposium Primary Pulmonary Hypertension, Sep. 6–10, 1998. D8.

Fratacci et al., "Inhaled nitric oxide; A selective pulmonary vasodilator of heparin–protamine vasoconstriction in sheep", Anesthesiology, 75: 990–999 (1991). D10A.

Freeman, B., "Free radical chemistry of nitric oxide Looking at the Dark side", Chest., supplement, 105: 79S–84S, Mar. 1994. D57.

Frostell et al., "Inhaled Nitric Oxide; a selective pulmonary vasodilator reversing hypoxic pulmonary vasoconstriction", Circulation, 83: 2038–2047 (1991). PUB 1, D15, W9, D10A.

Girard et al., "Inhaled nitric oxide (NO) in pulmonary hypertension following mitral valve replacement" Poster of (alleged) presentation ASA Annual meeting Oct. 26–30, 1991, Anesthesiology, vol. 75, 3A, Sep. 1991. PUB 9.

Girard et al., "Inhaled nitric Oxide after mitral valve replacement in patients with chronic pulmonary artery hypertension", Anesthesiology, 77: 880–883, 1992. D50, D10A.

Glasson and Tuesday, "The atmospheric thermal oxidation of nitric oxide", p. 2901, Oct. 5, 1963. PUB 2.

Higenbottam et al., "Inhaled Endothelium derived relaxing factor (EDRF) in primary hypertension" Rev. Resp. Suppl. 137: 107 (1988). PUB 4, D2.

Holleman–Wiberg, "Lehrbuch der Anorganischen Chemie", XV. 1.1.1 (1985). D36 (including translation found on p. 26 of Letter from The General Hospital, Apr. 12, 2002).

Ignarro et al., "Endothelium–derived relaxing factor and nitric oxide possess identical pharmacologic properties as relaxants of bovine arterial and venous smooth muscle", The Journal of Pharmacology and Experimental Therapeutics, 246: 218–226 (1988). D1.

Invitation National Inventor of the Year Award, 2003, Zapol and Frostell, Intellectual Property Owners Association, Jun. 4, 2003. D59.

Johns, "EDRF / Nitric Oxide: the endogenous nitrovasodilator an a new cellular messenger", The Journal of Anesthesiology, 75(6):927–931, Dec. 1991. D10A, D12.

Kacmarek et al., "Nitric oxide as a bronchodilator in methacholine induced bronchospasm in mild asthmatics", Abstract form, 1993 ALA/ATS International Conference, May 16–19, 1993. D10A.

Kinsella et al., "Low–dose inhalational nitric oxide in persistent pulmonary hypertension of the newborn", The Lancet, 340: 819–820 (1992). D10A.

Leaflet 1988 Annual Meeting American Lung Association American Thoracic Society. AL 8A.

Lumb, A.B., "Nunn's applied respiratory physiology", 5th ed. Butterworth, Heinemann, 23–29 (2000). D42.

Meijer and Piiper, "Nitric Oxide (NO), a new test gas for study of alveolar–capillary diffusion", Eur. Resp. Journal, 2: 494–498 (1989). D22.

Messent and Griffiths, "Pharmacotherapy in lung injury", Thorax, 47: 651–656 (1992). D10A.

Moinard and Guenard, "Determination of lung capillary blood volume and membrane diffusing capacity in patients with COLD using the NO–CO method", Eur. Respir. Journal, 3: 318–322, 1990. D5.

Munakata et al., "Is Epithelium derived relaxing factor (EpDRF) also nitric oxide?", Am. Rev. Resp. Dis. Suppl. 1989; 139;A351. D41.

Murray, John F., "The normal lung; the basis for diagnosis and treatment of pulmonary disease", W.B. Saunders Comp., pp. 24–31, 1976. D43.

Norman et al., "Nitrogen Oxides in Tobacco Smoke", Nature, 205: 915–916 (1965). D4.

Pearl, "Inhaled Nitric Oxide; the past the present and the future", The Journal of Anesthesiology, 78: 413–416 (1993). D14, D10A.

Pepke–Zaba et al., "Inhaled nitric oxide as a cause of selective pulmonary vasodilatation in pulmonary hypertension" The Lancet, 338 (8776): 1173–1174, 1991. W8, PUB 7, D10A.

Pepke–Zaba et al., "Acute pulmonary vasodilator effects of inhaled nitric oxide (NO) in patients with primary pulmonary hypertension (PPH)" Eur. Resp. Journal, Joint Meeting SEP–SEPCR, Abstracts, vol. 13, Suppl. 10: 313S, Sep. 1990. PUB 5, D27, AL8A.

Pepke–Zaba et al., "Inhaled nitric oxide (NO), a selective pulmonary vasodilator", Thorax, 44: 313–334, 1989. D26.

Prys–Roberts, C., "Principles of treatment of poisoning by higher oxides of nitrogen", Brit. Journal of Anaesthesia, 39: 432–448, 1967. D54.

Rich, "Primary Pulmonary Hypertension", World Symposium—Primary Pulmonary Hypertension 1998, p. 3, D16.

Roberts et al., "Inhaled nitric oxide in persistent pulmonary hypertension of the newborn", The Lancet, 340: 818–819 (1992). D10A.

Rossaint et al., "Inhaled nitric oxide for the adult respiratory distress syndrome", New England J. of Med., 328: 399–405 (1993). D10A.

Salzburger Nachrichten, "Viagra Forschung profitierte", world wide web at salzburg.com, Jan. 1999. W5 (including English translation).

Shiel, O'M. F., "Morbid anatomical changes in the lungs of dogs after inhalation of higher oxides of nitrogen during anaesthesia", Brit. Journal of Anaesthesia, 39: 413–424 (1967). D53.

Swami and Keogh, The injured lung: conventional and novel respiratory therapy, Thorax, 1992, 47:555–562. D10A(h), D13.

US Dept. Health and Human Services, "NIOSH recommendations for occupational safety and health standards 1988", Morbidity and Mortality Weekly Report 37:S7 (1988). D9.

Vedernikov et al., "Heterogeneity of the response of venous smooth muscle to arterial endothelium–derived relaxing factor (EDRF) in respect of the role of nitric oxide", Basic Res. Cardiol., 83: 122–127 (1988). D23.

Volker, Kreye and Marquard, "Comparison of sodium nitroprusside and isoprenaline aerosols in histamine–induced bronchial asthma of the guinea pig", Schmiedeberg's Arch. Pharmacol. 306: 203–207 (1979). D47.

West, John B., "Pulmonary Pathophysiology—the essentials", 5th ed. Williams and Wilkins, p. 67 (1998). D44.

Chapter XIX Pulmonary vascular disease and Cor Pulmonale, Scientific Am. Med., p. 1 (1993). D10A.

Yoshida et al., "Metabolic fate of nitric oxide" Int. Arch. Occup. Env. Health 46, 71–77 (1980). D17.

Zapol et al., "Inhaled Nitric Oxide selectively reduces pulmonary hypertension in severe ARDS and improves gas exchanges as well as right heart ejection fraction. A case report" Am. Rev. Resp. Disease Suppl., Abstracts, 1991 International Conference, vol. 143(4): A248, Apr. 1991. PUB10.

Arnold et al., "Cigarette Smoke Activates Guanylate Cyclase and Increases Guanosine 3',5'–Monophosphate in Tissues," Science, 198(4320): 934–936 (1977).

Fanta and Ingram, "Asthma," Scientific American Medicine, vol. 2, Ch. 14–II, pp. 1–18, Scientific American, Inc.(1988).

Fukase, "The Effects of Gaseous Air Pollutants on Peroxidative Metabolism in Mouse Lungs," Japanese Journal of Hygiene, 34: 777–792 (1980).

Ignarro, "Biological Actions and Properties of Endothelium–Derived Nitric Oxide Formed and Released from Artery and Vein," Circ. Res., 65(1):1–21 (1989).

Jansen et al., "The Relaxant Properties in Guinea Pig Airways of S–Nitrosothiols," J. Pharmaol. Exp. Ther., 261(1):154–160 (1992).

Kagawa, "Respiratory Effects of 2–hr Exposure to 1.0 ppm Nitric Oxide in Normal Subjects," Environ. Res., 27:485–490 (1982).

Kolata, "Key Signal of Cells Found to be a Common Gas," The New York Times, Jul. 2, 1991, Retrieved Online at nytimes.com on May 14, 2008.

Mahon, "Drugs and the Respiratory System," Principles of Medical Pharmacology, Fifth Ed. Ch. 39, pp. 392–397 (1989).

Meier, "Using Asthma Inhalers, But Correctly," The New York Times, Aug. 10, 1991, Retrieved Online at nytimes.com on May 14, 2008.

Moncada et al., "Nitric oxide: physiology, pathophysiology, and pharmacology," Pharmacol. Rev., 42(2): 109–142 (1991).

Myers et al., "Vasorelaxant Properties of the Endothelium–derived Relaxing Factor More Closely Resemble S–Nitrosocysteine Than Nitric Oxide," Nature, 345(6271):161–163 (1990).

Oda et al., "Lifetime Exposure to 2.4 ppm Nitric Oxide in Mice," Environ. Res., 22: 254–263 (1980).

Oda et al., "Nitrosylhemoglobin and Carboxyhemoglobin in the Blood of Mice Simultaneously Exposed to Nitric Oxide and Carbon Monoxide," Bulletin of Environmental Contamination & Toxicology, 16:582–587 (1976).

Oda et al., "Reaction of Hemoglobin with Nitric Oxide and Nitrogen Dioxide in Mice," Journal of Toxicology and Environmental Health, 6:673–678 (1980).

Resnick and Yalla, "Evaluation and Medical Management of Urinary Incontinence," Campbell's Urology, Sixth Edition, (14):652–655 (1992).

Sharrock et al., "Blood Analysis of Rabbits Exposed to Nitrogen Monoxides," Chemosphere, 13:959–964 (1984).

Wagner, "Absorption of NO and $NO_2$ in TLV and MAC Concentrations on Inhalation," Staub–Reinhalt Luft, 30: 380–381 (1970). (including English translation).

Yoshida et al., "Metabolic Fate of Nitric Oxide," Int. Arch. Occup. Environ. Health, 46:71–77(1980).

Yoshida et al., "The Effects of Exposure to NO or $NO_2$ and an Antigen on the Breathing Curve Pattern in Guinea Pigs," Environ. Res., 21:458–466 (1980).

Zapol, W.M. et al., "Regional Blood Flow During Simulated Diving in the Conscious Weddell Seal," J. Appl. Physiol., 47(5):968–973 (1979).

Garg et al., "Nitric Oxide–Generating Vasodilators and 8–Bromo–Cyclic Guanosine Monophosphate Inhibit Vascular Smooth Muscle Cells," J. Clin. Invest., 83:1774–8458, 1989.

Barst, "Pharmacologically Induced Pulmonary Vasodilatation in Children and Young Adults with Primary Pulmonary Hypertension," Chest, 89(4): 497–503 (1986).

Dresdale et al., "Recent Studies in Primary Pulmonary Hypertension Including Pharmacodynamic Observations on Pulmonary Vascular Resistance," The Bulletin, pp. 195–207, presented before the Section on Medicine of the New York Academy of Medicine, Mar. 1954.

Graves et al., "Persistent Pulmonary Hypertension in the Neonate," Chest, 93: 638–641 (1988).

Lefrak et al., "Current Status of Prolonged Extracorporeal Membrane Oxygenation for Acute Respiratory Failure," Chest, 63:773–782 (1973).

Maycock, "Persistent Pulmonary Hypertension of the Newborn," Retrieved from Internet:URL:http://depts.washington.edu/nicuweb/NICU–WEB/pphn.stm on May 4, 2008.

Simonneau et al., "Clinical Classification of Pulmonary Hypertension," Journal of the American College of Cardiology, 43(12): 5S–12S (2004).

Yoshida et al., "Biotransformation of Nitric Oxide, Nitrite and Nitrate," Int. Arch. Occup. Environ. Health, 52: 103–115 (1983).

Beutler, "Methemoglobinemia and sulfhemoglobinemia", Hematology, McGraw Hill, New York, Chapter 54, pp. 491–494 (1977).

Clark et al., "Low–Dose Nitric Oxide Therapy for Persistent Pulmonary Hypertension Of The Newborn", New Engl. J. Med., 342:469–474 (2000).

American Lung Association, "Primary Pulmonary Hypertension (PPH) Fact Sheet", Nov. 2003. Downloaded from www.lungusa.org on Jun. 10, 2008.

Fleetham et al., "Methemoglobinemia and the Oxides of Nitrogen", New Engl. J. Med., 298 (1978).

Gosselin et al., Clinical Toxicology of Commercial Products, chapter III–31–III–36, $5^{th}$ ed., (1984).

Hackman et al. "Pharmacotherapy for Idiopathic Pulmonary Arterial Hypertension During the Past 25 Years", Reviews of Therapeutics, 26:68–94 (2006). Abstract.

Martin, "Nitric Oxide for Preemies—Not so Fast", New Engl. J. Med., 349: 2157–2159 (2003).

Nelson, Textbook of Pediatrics, Saunders Elsevier, $18^{th}$ edition, Item 101.8, pp. 744–746 (2007). Excerpt.

Palevsky et al., "Prostacyclin and Acetylcholine as Screening Agents for Acute Pulmonary Vasodilator Responsiveness in Primary Pulmonary Hypertension", Circulation 82:2018–2026 (1990).

Phelps et al., "Tecopherol Efficacy and Safety for Preventing Retinopathy of Prematurity: a Randomized, Controlled, Double–Masked Trial", Pediatrics 79(4):489–500 (1987).

Reid, "Constructive and Restrictive Pulmonary Hypertension in the Newborn and Infant", 1(2):287–299 (1987).

Steinhorn, "Persistent Pulmonary Hypertension of the Newborn", Apr. 19, 2007. Downloaded from www.emedicine.com on Jun. 10, 2008.

Oudiz, "Primary Pulmonary Hypertension", Aug. 29, 2007. Downloaded from emedicine.medscape.com/article/301450–print on Mar. 20, 2009.

The Family Practice Notebook website—Endotracheal Tube. Downloaded from www.fpnotebook.com/Lung/Procedure/EndtrchITb.htm on Mar. 20, 2009.

Priestley and Huh, "Respiratory Failure", Feb. 12, 2008. Downloaded from emedicine.medscape.com/article/908172–print on Mar. 20, 2009.

Anesthesia Equipment Resources: Non–Rebreathing Circuits. Downloaded from www.asevet.com/resources/circuits/nrb.htm on Mar. 20, 2009.

Gerlach et al., "Autoinhalation of Nitric Oxide After Endogenous Synthesis in Nasopharynx", Lancet 343:518–519, 1994.

Nootens et al., "The Prevalence and Significance of a Patent Foramen Ovale in Pulmonary Hypertension". Chest 104: 73–1675, 1993.

Beck et al., "Inhaled Nitric Oxide Improves Hemodynamics in Patients with Acute Pulmonary Hypertension After High–Risk Cardiac Surgery", Perfusion 14:37–42, 1999.

Argenziano et al., "Randomized, Double–Blind Trial of Inhaled Nitric Oxide in LVAD Recipients with Pulmonary Hypertension", Ann Thorac Surg. 65:340–345, 1998.

O'Brodovich et al., "Bronchopulmonary Dysplasia. Unresolved Neonatal Acute Lung Injury", Am Rev Respir Dis 132:694–709, 1985.

Baraldi and Fillippone, "Chronic Lung Disease After Premature Birth", New Eng J Med 357:1946–1955, 2007.

Rubin and Kerr, "Pulmonary Hypertension, in Critical Care Medicine: Principles of Diagnosis and Management in the Adult", pp. 900–909, 2d Ed., Parillo JE, Dellinger RP (eds.), Mosby, Inc. 2001.

Kinsella and Abman, "The Role of Inhaled Nitric Oxide in Persistent Pulmonary Hypertension of the Newborn, in Acute Respiratory Care of the Neonate: A Self–Study Course", pp. 369–378. 2d Ed., Askin DF (ed.), NICU Ink Book Publishers, 1997.

Catterall, "A New Mask For Delivering Oxygen or Other Gases", Br. Med. J., (5190): 1941–1942, 1960.

Williams et al., "A Comparison of Oxygen Therapy Devices Used in the Postoperative Recovery Period", Anaesthesia, 43: 131–135, 1988.

Young et al., "Artificial Ventilation: History, Equipment and Techniques," Thorax, 45: 753–75, 1990.

Barberá et al., "Worsening of pulmonary gas exchange with nitric oxide inhalation in chronic obstructive pulmonary disease", The Lancet, vol. 347, pp. 436–440 (1996).

Channick MD et al., "Inhaled Nitric Oxide Reverses Hypoxic Pulmonary Vasoconstriction in Dogs", Chest, vol. 105(4), pp. 1842–1847 (1994).

Clark, "Monitor and Control of Blood and Tissue Oxygen Tensions," Trans Amer Soc Artif Int Organs 2, pp. 41–48 (1956).

Jacob et al., "Hemodynamic effects and metabolic fate of inhaled nitric oxide in hypoxic piglets", Metabolic Fate of Inhaled NO, pp. 1794–1801 (1994).

Jones et al., "Treatment for primary pulmonary hypertension with intravenous epoprostenol (Prostacyclin)", Br Heart, vol. 57, pp. 270–278 (1987).

JP Szidon and AP Fishman, in "Pulmonary Diseases and Disorders," Second Edition, AP Fishman Editor, McGraw–Hill Book Co., pp. 313–366 (1988).

Klemm et al., "Effects of nitric oxide synthase inhibition combined with nitric oxide inhalation in a porcine model of endotoxin shock", British Journal of Pharmacology, vol. 114, pp. 363–368 (1995).

Kouyoumdjian et al., Continuous Inhalation of Nitric Oxide Protects against Development of Pulmonary Hypertension in Chronically Hypoxic Rats, J. Clin. Invest, pp. 578–584 (1992).

Meier–Stauss et al., Eur J Pediatr 149:851–855 (1990).

Myers et al., "Vasorelaxant Properties of the Endothelium–derived Relaxing Factor More Closely Resemble S–Nitrosocysteine Than Nitric Oxide," Nature, 345(6271):161–163 (1990).

Mills et al., "Nitric oxide and exercise in the horse", Journal of Physiology, vol. 495(3), pp. 863–874 (1996).

Rubin and Kerr, "Pulmonary Hypertension, in Critical Care Medicine: Principles of Diagnosis and Management in the Adult", pp. 900–909. 2d Ed., Parillo JE, Dellinger RP (eds.), Mosby, Inc. 2001.

Sustronck et al., "Effect of inhaled nitric oxide on the hypoxic pulmonary vasoconstrictor response in anaesthetized calves", Research of Veterinary Science, vol. 63, pp. 193–197 (1997).

Vermeersch MD et al., "Soluble Guanylate Cycloseal Deficiency Selectivity Inhibits the Pulmonary Vasodilator Response to Nitric Oxide and Increases the Pulmonary Vascular Remodeling Response to Chronic Hypoxia", sGC in Pulmonary Vascular Tone and Remodeling, pp. 936–943 (2007).

Zapol and Snider, "Pulmonary hypertension in severe acute respiratory failure," N Engl J Med. 296:, pp. 476–480 (1977).

Zayek MD et al., "Effect of nitric oxide on the survival rate and incidence of lung injury in newborn lambs with persistent pulmonary hypertension", The Journal of Pediatrics, pp. 947–952 (1993).

Written Submission by Air Products and Chemicals, Inc. et al, in European Patent No. 1516639, dated Sep. 24, 2009.

Frostell et al., "Inhaled Nitric Oxide Selectivity Reverses Human Hypoxic Pulmonary Vasoconstriction without Causing Systemic Vasodiliation", Anesthesiology, pp. 427–435 (1993).

Finer, "Nitric oxide for respiratory failure in infants born at or near term (Review)", The Cochrane Collaboration, pp. 1–42 (1993).

Roberts Jr. et al., "Inhaled Nitric Oxide in Neonatal Pulmonary Hypertension and Severe Respiratory Distress Syndrome: Experimental and Clinical Studies", Nitric Oxide and the Lung (edited by Warren M. Zapol and Kenneth D. Bloch), pp. 333–363 (1997).

The Cleveland Clinic Disaster, The Encyclopedia of Cleveland History, 1 page (1998).

Cleveland, OH Clinic Explosion and Fire, 5 pages, May 1929.

Annex I Summary of Product Characteristics, 22 pages.

Gerlach et al., "Low Levels of Inhaled Nitric Oxide in Acute Lung Injury", Nitric Oxide and the Lung, (edited by Warren M. Zapol and Kenneth D. Bloch), pp. 271–283 (1997).

Foubert et al., "Safety guidelines for use of nitric oxide", Lancet, vol. 339, pp. 1615–1616 (1992).

Radermacher M.D., "Comparison of Ketanserin and Sodium Nitroprusside in Patients with Severe ARDS", Clinical Reports, vol. 68(1), pp. 152–157 (1988).

Falbe and Regitz, Rompp Chemie Lexikon, 9th Edition, p. 2555, 1990. (see N1 for a summary of opponent's view of this non–English reference).

Proprietor's Observations to the Notices of Opposition in EP 0786264, Jun. 26, 2009 (Auxiliary Requests attached).

Except from Summary of Product Characteristics of INOmax™ (No date).

Printout from Drugs Pro (an online pharmacy) regarding "Nitromint". Downloaded from www.drug-pro.com/heart-disease/nitromint.html on Jun. 18, 2009.

Heigenbottam et al., "Inhaled Endothelium Derived–Relaxing Factor (EDRF) in Primary Pulmonary Hypertension (PPH)," Am. Respir Dis. [Suppl.], vol. 137, p. 107 (1988).

Pepke–Zaba et al., "Inhaled nitric oxide (NO), a selective pulmonary vasodilator," Thorax, vol. 44, p. 334P (1989).

Kugawa et al., "Respiratory Effects of 2–hr Exposure to 1.0 ppm Nitric Oxide in Normal Subjects," Environmental Research, vol.27, p. 485–490 (1982).

Greenberg et al., "Thromboxane A2 mediated brochoconstriction in the anesthetized guinea pig," Eur. J. Pharmacol., vol. 80(1), p. 19–27 (1982) (Abstract only).

Meyer and Piiper, "Nitric oxide (NO), a new test gas for study of alveolar–capillary diffusion," Eur. Respir. J., vol. 2, p. 494–496 (1989).

Abstract: Higenbottam et al. "Inhaled Endothelium Derived–Relaxing Factor (EDRF) in Primary Hypertension (PPH)" American Review of Respiratory Disease Supplement, vol.137, p. 107, 1988.

Abstract: Pepke–Zaba et al. "Acute pulmonary vasodilator effects of inhaled nitric oxide (NO) in patients with primary pulmonary hypertension (PPH)," Eur. Resp. Journal, Joint Meeting SEP–SEPCR, Abstracts, vol. 3, Suppl. 10:313S, Sep. 13, 1990.

Abstract: Pepke–Zaba et al., "Inhaled Nitric Oxide (NO), a Selective Pulmonary Vasodilator," Proceedings of the British Thoracic Society, Thorax 1989:44:334P.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-18 and 24-29 is confirmed.

Claims 19-23 and 30-39 were not reexamined.

\* \* \* \* \*